United States Patent [19]

Yamamoto et al.

[11] Patent Number: 5,681,954
[45] Date of Patent: Oct. 28, 1997

[54] PIPERAZINE DERIVATIVES

[75] Inventors: Kenjiro Yamamoto; Atsushi Hasegawa; Hideki Kubota, all of Tokyo; Masahiro Ando, deceased, late of Akita, by Hideo Ando, legal representative; Hitoshi Yamaguchi, Tokyo, all of Japan

[73] Assignee: Daiichi Pharmaceutical Co., Ltd., Tokyo, Japan

[21] Appl. No.: 416,311

[22] Filed: Apr. 4, 1995

Related U.S. Application Data

[63] Continuation-in-part of Ser. No. 242,842, May 16, 1994, abandoned.

[30] Foreign Application Priority Data

May 14, 1993 [JP] Japan .................................. 5-011277

[51] Int. Cl.$^6$ .................................................. C07D 413/00
[52] U.S. Cl. .............................. 544/114; 544/371; 544/364; 544/121; 544/368; 544/392; 544/394; 544/372; 544/393; 544/359; 544/373; 544/379; 544/360; 544/370; 544/114
[58] Field of Search .................................. 544/371, 364, 544/121, 368, 392, 394, 372, 393, 359, 373, 379, 360, 370, 114

[56] References Cited

U.S. PATENT DOCUMENTS

| | | | |
|---|---|---|---|
| 3,362,956 | 1/1968 | Archer | 260/268 |
| 4,179,505 | 12/1979 | Raeymaekers et al. | 424/250 |
| 4,302,589 | 11/1981 | Faushawe | 546/201 |
| 4,426,383 | 1/1984 | Sugimoto et al. | 424/253 |
| 4,954,503 | 9/1990 | Strupczewski et al. | 514/254 |
| 4,988,809 | 1/1991 | Seidel et al. | 544/121 |
| 5,182,280 | 1/1993 | Cuberes-Altisent et al. | 514/252 |

FOREIGN PATENT DOCUMENTS

| | | |
|---|---|---|
| 0046572A2 | 3/1982 | European Pat. Off. . |
| 0126480A1 | 11/1984 | European Pat. Off. . |
| 9407875 | 4/1994 | WIPO . |

*Primary Examiner*—Joseph McKane
*Assistant Examiner*—Richard S. Myers, Jr.
*Attorney, Agent, or Firm*—Sughrue,Mion,Zinn,Macpeak & Seas, PLLC

[57] ABSTRACT

A compound represented by formula (I):

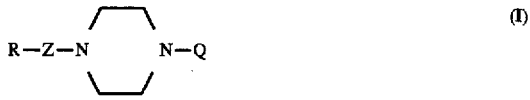

wherein Q represents an aryl group, a heterocyclic group, a diarylmethyl group, an aralkyl group composed of an aryl group and an alkylene group, an alkyl group or a cycloalkyl group, in which the aryl group, heterocyclic group, and the aryl moiety of the diarylmethyl group and aralkyl group may be substituted with one or more substituents; R represents a bicyclic, substituted, nitrogen-containing heterocyclic group or a substituted phenyl group, in which the nitrogen-containing heterocyclic group is composed of a 5-membered, substituted, aromatic or saturated ring containing one or two nitrogen atoms and a 6-membered ring; and Z represents an alkylene group, an alkenylene group, an alkylene group, a carbonyl group, an alkylene group containing a carbonyl group or an oxalyl group, or a salt thereof. The compound has calmodulin inhibitory activity and is useful as a treating agent for diseases in the circulatory organs or in the cerebral region which are caused by excessive activation of calmodulin.

14 Claims, No Drawings

PIPERAZINE DERIVATIVES

This application is a Continuation-In-Part (CIP) of U.S. application Ser. No. 08/242,842, filed May 16, 1994, and abandoned upon the filing of this CIP application.

FIELD OF THE INVENTION

This invention relates to a piperazine derivative or a salt thereof which is useful as a treating agent for diseases in circulatory organs and the cerebral region.

BACKGROUND OF THE INVENTION

Some piperazine derivatives exhibit activities toward the central nervous system, such as anti-anxiety activity and anti-convulsive activity, as disclosed in U.S. Pat. No. 3,362,956. It is also known that a certain kind of piperazine derivatives possess calmodulin inhibitory activity as reported in Arzneim.-Forsch., Vol. 37(4), pp. 498–502 (1987).

The piperazine derivatives represented by formula (I) according to the present invention are novel compounds whose physiological activity has not set been reported.

In recent years, diseases of circulatory organs or in the cerebral region, such as hypertension, cardiac insufficiency, angina pectoris, apoplexy, cerebral infarction, Alzheimer's disease, and Parkinson's disease, have been increasing, and various drugs for prevention and treatment of these diseases have been developed. On the other hand, compounds with calmodulin inhibitory activity have been discovered, and some of them have been revealed to have antihypertensive activity and vasodilatory activity.

SUMMARY OF THE INVENTION

An object of the present invention is to provide a compound useful as treating agent for various diseases of circulatory organs or the cerebral region, particularly those diseases caused by excessive activation of calmodulin.

As a result of extensive investigations, the present inventors have succeeded in preparing novel piperazine derivatives represented by formula (I) shown below and salts thereof and have ascertained that these compounds have calmodulin inhibitory activity, antihypoxia activity, inhibitory activity on delayed neuronal death in the hippocampus of merions (Meriones shawi), and improving activity on cerebral edema. That is, the inventors have elucidated that the compounds of formula (I) exhibit not only calmodulin inhibitory activity but strong cerebral protective activity.

The present invention relates to a compound represented by formula (I):

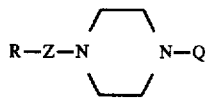

(I)

wherein
Q represents
an aryl group,
a heterocyclic group,
a diarylmethyl group,
an aralkyl group composed of an aryl group and an alkylene group having from 1 to 6 carbon atoms,
an alkyl group having from 1 to 8 carbon atoms, or a cycloalkyl group havihg from 3 to 8 carbon atoms, in which the aryl group, heterocyclic group, and the aryl moiety of the diarylmethyl group and aralkyl group may be substituted with one or more substituents selected from a group of an alkyl group having from 1 to 6 carbon atoms,
an alkoxyl group having from 1 to 6 carbon atoms,
a trifluoromethyl group,
a 2,2,2-trifluoroethyl group,
a trifluoromethoxyl group,
a 2,2,2-trifluoroethoxyl group,
an alkylthio group having from 1 to 6 carbon atoms,
an alkylsulfinyl group having from 1 to 6 carbon atoms,
an alkylsulfonyl group having from 1 to 6 carbon atoms,
an alkanoyl group composed of an alkyl group having from 1 to 6 carbon atoms and a carbonyl group,
an alkanoyloxy group having from 2 to 7 carbon atoms,
an alkanoylamino group having from 2 to 7 carbon atoms,
an amino group,
a monoalkylamino group having from 1 to 6 carbon atoms in the alkyl moiety thereof,
a dialkylamino group having from 1 to 6 carbon atoms in each alkyl moiety thereof,
a hydroxyl group,
a halogen atom,
a perfluoroalkyl group having from 2 to 6 carbon atoms,
a cyano group,
a nitro group,
a carboxyl group,
an alkoxycarbonyl group composed of an alkoxyl group having from 1 to 6 carbon atoms and a carbonyl group,
a tetrazolyl group,
a sulfamoyl group,
a methylenedioxy group,
an ethylenedioxy group,
a morpholinosulfonyl group,
a piperazinosulfonyl group,
a 4-alkylpiperazinosulfonyl group having from 1 to 6 carbon atoms,
a 4-dialkylaminopiperidino group having from 1 to 6 carbon atoms in each alkyl moiety thereof,
a 4-monoalkylaminopiperidino group having from 1 to 6 carbon atoms in the alkyl moiety thereof,
and a 4-aminopiperidino group;
R represents a bicyclic nitrogen-containing heterocyclic group having substituents $R^1$ and $R^2$, or a phenyl group having substituents $R^1$ and $R^2$, in which the nitrogen-containing heterocyclic group is composed of a 6-membered ring and a 5-membered ring, one or two nitrogen atoms are present on the 5-membered ring, the 5-membered nitrogen-containing ring may be an aromatic ring or a saturated ring, the nitrogen-containing saturated ring may contain a ketone moiety, and the phenyl group or the 5-membered ring of the bicyclic heterocyclic group is substituted by a substituent G selected from a group of
an alkyl group having from 1 to 6 carbon atoms,
a substituted or unsubstituted phenyl group,
a benzoyl group with the phenyl moiety thereof substituted or unsubstituted,
a benzylcarbonyl group with the phenyl moiety thereof substituted or unsubstituted,
a benzoylmethyl group with the phenyl moiety thereof substituted or unsubstituted,
an α-hydroxybenzyl group with the phenyl moiety thereof substituted or unsubstituted,
a substituted or unsubstituted 5-membered aromatic heterocyclic group containing a nitrogen atom, an oxygen atom or a sulfur atom as a hetero atom (wherein a nitrogen atom is present as the hetero atom, this has a hydrogen atom or an alkyl group having from 1 to 6 carbon atoms, or it is the site of bonding to the bicyclic nitrogen-containing heterocyclic group or the phenyl group),
a substituted or unsubstituted 5-membered aromatic heterocyclic group containing one nitrogen atom and, a nitrogen atom, an oxygen atom or a sulfur atom as the second hetero atom (wherein a nitrogen atom is present as the second hetero atom, this has a hydrogen atom or an alkyl group having from 1 to 6 carbon atoms, or it is the site of bonding to the bicyclic nitrogen-containing heterocyclic group or the phenyl group), a substituted or unsubstituted 5-membered aromatic heterocyclic group containing two nitrogen atoms and, a nitrogen atom, an oxygen atom or a sulfur atom as the third hetero atom (wherein a nitrogen atom is present as the third hetero atom, this has a hydrogen atom or an alkyl group having from 1 to 6 carbon atoms, or it is the site of bonding to the bicyclic nitrogen-containing heterocyclic group or the phenyl group), a substituted or unsubstituted 6-membered aromatic heterocyclic group containing one or two nitrogen atoms, a heterocyclic group substituted-alkyl group composed of a substituted or unsubstituted 5-membered aromatic heterocyclic group containing a nitrogen atom, an oxygen atom or a sulfur atom as a hetero atom (wherein a nitrogen atom is present as the hetero atom, this has a hydrogen atom or an alkyl group having from 1 to 6 carbon atoms) and an alkylene group of from 1 to 3 carbon atoms, a heterocyclic group substituted-alkyl group composed of a substituted or unsubstituted 5-membered aromatic heterocyclic group containing one nitrogen atom and, a nitrogen atom, an oxygen atom or a sulfur atom as the second hetero atom (wherein a nitrogen atom is present as the second hetero atom, this has a hydrogen atom or an alkyl group having from 1 to 6 carbon atoms or it is the site of bonding to the alkylene group) and an alkylene group of from 1 to 3 carbon atoms, a heterocyclic group substituted-alkyl group composed of a substituted or unsubstituted 5-membered aromatic heterocyclic group containing two nitrogen atoms and, a nitrogen atom, an oxygen atom or a sulfur atom as the third hetero atom (wherein a nitrogen atom is present as the third hetero atom, this has a hydrogen atom or an alkyl group having from 1 to 6 carbon atoms or it is the site of bonding to the alkylene group) and an alkylene group of from 1 to 3 carbon atoms, a heterocyclic group substituted-alkyl group composed of a substituted or unsubstituted 6-membered aromatic heterocyclic group containing one or two nitrogen atoms and an alkylene group of from 1 to 3 carbon atoms, a phenylhydroxyalkyl group composed of an alkylene group having one hydroxyl group and 2 to 3 carbon atoms and a substituted or unsubstituted phenyl group, a 2-phenylethenyl group wherein the phenyl group may be substituted, a tetrazolyl group, a morpholino group, an alkanoylamino group having from 2 to 7 carbon atoms, a tetrazolylalkyl group composed of a tetrazolyl group and an alkylene group having from 1 to 3 carbon atoms wherein the alkylene group is bonded to the carbon atom or nitrogen atom of the tetrazolyl group, a morpholinoalkyl group composed of a morpholino group and an alkylene group having from 1 to 3 carbon atoms, a 4-alkoxycarbonylcyclohexyl group having from 1 to 6 carbon atoms in the alkoxyl group thereof, an alkoxycarbonyl group having from 1 to 6 carbon atoms in the alkoxyl moiety thereof, an alkoxycarbonylalkyl group composed of an alkoxyl group having from 1 to 6 carbon atoms and an alkylene group having from 1 to 3 carbon atoms, a 1-alkylindol-2-yl group having from 1 to 6 carbon atoms in the alkyl moiety thereof wherein the indole moiety may further be substituted, a substituted or unsubstituted pyrrolidon-1-yl group, a 2-guanidinothiazolyl group, a (2-guanidinothiazolyl)alkyl group composed of a 2-guanidinothiazolyl group and an alkylene group having from 1 to 3 carbon atoms, a substituted or unsubstituted 1,4-dihydropyridyl group, a (4-alkylpiperazino)alkyl group composed of a 4-alkylpiperazino having an alkyl group of from 1 to 6 carbon atoms and an alkylene group of from 1 to 6 carbon atoms, a [4-(morpholinosulfonyl)phenyl]alkyl group composed of 4-(morpholinosulfonyl)phenyl group and an alkylene group of from 1 to 6 carbon atoms, a [4-(piperazinosulfonyl)phenyl]alkyl group composed of 4-(piperazinosulfonyl)phenyl group and an alkylene group of from 1 to 6 carbon atoms, a [4-(4-alkylpiperazinosulfonyl)phenyl]alkyl group composed of 4-(4-alkylpiperazinosulfonyl)phenyl group Wherein the alkyl group on piperazino group is that of from 1 to 6 carbon atoms, and an alkylene group of from 1 to 6 carbon atoms, an alkoxycarbonylalkyl group composed of an alkoxyl group of from 1 to 6 carbon atoms and a carbonyl group and.an alkylene group of from 1 to 6 carbon atoms, a carboxyalkyl group composed of a carboxyl group and an alkylene group of from 1 to 6 carbon atoms, a [4-(4-dialkylaminopiperidino)phenyl]alkyl group composed of a phenyl group having a 4-dialkylaminopiperidino group at 4-position, wherein each of the alkyl moiety of the dialkylamino group has from 1 to 6 carbon atoms independently, and an alkylene group of from 1 to 6 carbon atoms, a [4-(4-monoalkylaminopiperidino)phenyl]alkyl group composed of a phenyl group having a 4-monoalkylaminopiperidino group at 4-position, wherein the alkyl moiety of the monoalkylamino group has from 1 to 6 carbon atoms, and an alkylene group of from 1 to 6 carbon atoms, a [4-(4-aminopiperidino)phenyl]alkyl group composed of a phenyl group having a 4-aminopiperidino group at 4-position and an alkylene group of from 1 to 6 carbon atoms, a (4-dialkylaminopiperidino)alkyl group composed of a 4-dialkylaminopiperidino group, wherein each of the alkyl moiety of the dialkylamino group has from 1 to 6 carbon atoms independently, and an alkylene group of from 1 to 6 carbon atoms, a (4-alkylaminopiperidino)alkyl group composed of a 4-alkylaminopiperidino group, wherein the alkyl moiety of the alkylamino group has from 1 to 6 carbon atoms, and an alkylene group of from 1 to 6 carbon atoms, a (4-aminopiperidino)alkyl group composed of a 4-aminopiperidino group and an alkylene group of from 1 to 6 carbon atoms, a phenylalkyl group composed of a substituted or unsubstituted phenyl group and an alkylene group of from 1 to 6 carbon atoms, and a hydrogen atom, wherein in case the substituent G has a substituent(s), the substithent(s) is a member(s) selected from a group of an alkyl group having from 1 to 6 carbon atoms, an alkoxyl group having from 1 to 6 carbon atoms, a trifluoromethyl group, a 2,2,2-trifluoroethyl group, a trifluoromethoxyl group, a 2,2,2-trifluoroethoxyl group, an alkylthio group having from 1 to 6 carbon atoms, an alkylsulfinyl group having from 1 to 6 carbon atoms, an alkylsulfonyl group having from 1 to 6 carbon atoms, an alkanoyl group composed of an alkyl group having from 1 to 6 carbon atoms and a carbonyl group, an alkanoyloxy group having from 2 to 7 carbon atoms,
an alkanoylamino group having from 2 to 7 carbon atoms,
an amino group,
a monoalkylamino group having from 1 to 6 carbon atoms in the alkyl moiety thereof,
a dialkylamino group having from 1 to 6 carbon atoms in each alkyl moiety thereof,
a hydroxyl group,
a halogen atom,
a perfluoroalkyl group having from 2 to 6 carbon atoms,
a cyano group,
a nitro group,
a carboxyl group,
an alkoxycarbonyl group composed of an alkoxyl group having from 1 to 6 carbon atoms and a carbonyl group,
a tetrazolyl group,
a sulfamoyl group,
a methylenedioxy group,
an ethylenedioxy group,
a morpholinosulfonyl group,
a piperazinosulfonyl group,
a 4-alkylpiperazinosulfonyl group having from 1 to 6 carbon atoms,
a 4-dialkylaminopiperidino group having from 1 to 6 carbon atoms in each alkyl moiety thereof,
a 4-monoalkylaminopiperidino group having from 1 to 6 carbon atoms in the alkyl moiety thereof,
and a 4-aminopiperidino group;
$R^1$ and $R^2$ independently represent a member of the group consisting of:
an alkyl group having from 1 to 6 carbon atoms,
an alkoxyl group having from 1 to 6 carbon atoms,
a trifluoromethyl group,
a 2,2,2-trifluoroethyl group,
a trifluoromethoxyl group,
a 2,2,2-triflouroethoxyl group,
an alkylthio group having from 1 to 6 carbon atoms,
an alkylsulfinyl group having from 1 to 6 carbon atoms,
an alkylsulfonyl group having from 1 to 6 carbon atoms,
an alkanoyl group composed of an alkyl group having from 1 to 6 carbon atoms and a carbonyl group,
an alkanoyloxy group having from 2 to 7 carbon atoms,
an alkanoylamino group having from 2 to 7 carbon atoms,
an amino group,
a monoalkylamino group having from 1 to 6 carbon atoms in the alkyl moiety thereof,
a dialkylamino group having from 1 to 6 carbon atoms in each alkyl moiety thereof,
a hydroxyl group,
a halogen atom,
a perfluoroalkyl group having from 2 to 6 carbon atoms,
a cyano group,
a nitro group,
a carboxyl group,
an alkoxycarbonyl group composed of an alkoxyl group having from 1 to 6 carbon atoms and a carbonyl group,
a tetrazolyl group,
a sulfamoyl group,
a methylenedioxy group,
an ethylenedioxy group,
a morpholinosulfonyl group,
a piperazinosulfonyl group,
a 4-alkylpiperazinosulfonyl group having from 1 to 6 carbon atoms,
a 4-dialkylaminopiperidino group having from 1 to 6 carbon atoms in the alkyl moiety thereof,
a 4-monoalkylaminopiperidino group having from 1 to 6 carbon atoms in the alkyl moiety thereof,
and a 4-aminopiperidino group;
and z represents
an alkylene group having from 1 to 3 carbon atoms,
an alkenylene group having from 2 to 4 carbon atoms,
an alkylene group having one hydroxyl group and from 1 to 3 carbon atoms,
a carbonyl group,
an alkylene group containing a carbonyl group at one end or on the middle of the carbon chain thereof,
or an oxalyl group,
or a salt thereof.

This invention further relates to a compound of formula (I), wherein the substituent R has a structure represented by the following formula:

or wherein G is as defined before, and $R^1$ and $R^2$ independently represents
an alkyl group having from 1 to 6 carbon atoms,
an alkoxyl group having from 1 to 6 carbon atoms,
a trifluoromethyl group,
a 2,2,2-trifluoroethyl group,
a trifluoromethoxyl group,
a 2,2,2-trifluoroethoxyl group,
an alkylthio group having from 1 to 6 carbon atoms,
an alkylsulfinyl group having from 1 to 6 carbon at atoms,
an alkylsulfonyl group having from 1 to 6 carbon atoms,
an alkanoyl group composed of an alkyl group having from 1 to 6 carbon atoms and a carbonyl group,
an alkanoyloxy group having from 2 to 7 carbon atoms,
an alkanoylamino group having from 2 to 7 carbon atoms,
an amino group,
a monoalkylamino group having from 1 to 6 carbon atoms in the alkyl moiety thereof,
a dialkylamino group having from 1 to 6 carbon atoms in each alkyl moiety thereof,
a hydroxyl group,
a halogen atom,
a perfluoroalkyl group having from 2 to 6 carbon atoms,
a cyano group,
a nitro group,
a carboxyl group,
an alkoxycarbonyl group composed of an alkoxyl group having from 1 to 6 carbon atoms and a carbonyl group,
a tetrazolyl group,
a sulfamoyl group,
a methylenedioxy group,
an ethylenedioxy group,
a morpholinosulfonyl group,
a piperazinosulfonyl group,
a 4-alkylpiperazinosulfonyl group having from 1 to 6 carbon atoms,
a 4-dialkylaminopiperidino group having from 1 to 6 carbon atoms in each alkyl moiety thereof, a 4-monoalkylaminopiperidino group having from 1 to 6 carbon atoms in the alkyl moiety thereof, or a 4-aminopiperidino group.

This invention also relates to a compound of formula (I), wherein the substituent R has a structure represented by the following formula:

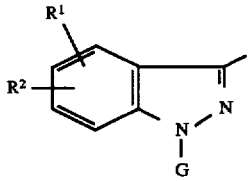

This invention further relates to a compound of formula (I), wherein the substituent R has a structure represented by the following formula:

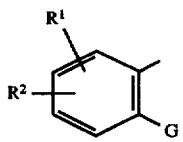

This invention also relates to a compound of formula (I), wherein the substituent Q is a phenyl group having at least one substituent at the meta-position of the connecting position of the phenyl group to the piperazine moiety.

This invention further relates to a compound of formula (I), wherein the meta-substituent of the phenyl group for the substituent Q is a halogen atom.

This invention also relates to a compound of formula (I), wherein Q is a 2-methyl-3-chlorophenyl group.

This invention further relates to a compound of formula (I), wherein Z is the alkylene group having 2 or 3 carbon atoms.

This invention also relates to a compound of formula (I), wherein Z is the alkylene group having 2 carbon atoms.

This invention further relates to a compound of formula (I), wherein the substituent R has a 5,6-dimethoxy-1H-indazole moiety.

This invention also relates to a compound of formula (2), wherein the substituent R has a 5,6-methylenedioxy-1H-indazole moiety.

This invention further relates to a compound of formula (I), wherein the substituent G on R is a member selected from a group of a 3,4-dimethoxybenzyl group, 4-imidazolylmethyl group, a 2-pyridylmethyl group, 3-pyridylmethyl group and a 4-pyridylmethyl group.

This invention also relates to a compound of formula (I), wherein the substituent R has 2-substituted-4,5-dimethoxyphenyl moiety.

This invention further relates to a compound of formula (I), wherein the substituent R has 2-substituted-4,5-methylenedioxyphenyl moiety.

The present invention also relates to a treating agent for a circulatory disease or a disease in the cerebral region which contains the novel piperazine derivative represented by formula (I) or a salt thereof and exhibits calmodulin inhibitory activity.

DETAILED DESCRIPTION OF THE INVENTION

The salts of the compound of formula (I) typically include acid addition salts. Acids for preparing the acid addition salts of the compound of formula (I) may be organic or inorganic and include hydrochloric acid, sulfuric acid, nitric acid, phosphoric acid, carboxylic acids (e.g., acetic acid, propionic acid, lactic acid, maleic acid, and fumaric acid), and sulfonic acids (e.g., methanesulfonic acid, benzenesulfonic acid, and toluenesulfonic acid). As a matter of course, the compound of formula (I) can be administered to humans in the form of an acid addition salt as far as the salt-forming acid is harmless to humans.

In case when a compound of the present invention of formula (I) have an acidic substituent, such a compound may be converted to a salt with, an organic or an inorganic bases. And the compound of the present invention or the salts thereof may form as hydrate(s).

The compound according to the present invention consists of a piperazine ring with a partial structure represented by Q bonded to one nitrogen atom thereof and a partial structure represented by R Bonded to the other nitrogen atom via a connecting group represented by Z.

Partial structure Q is a substituent selected from (1) an aryl group, (2) a heterocyclic group, (3) a diarylmethyl group, (4) an aralkyl group having from 1 to 6 carbon atoms in the alkyl moiety thereof, (5) an alkyl group having from 1 to 8 carbon atoms, and (6) a cycloalkyl group having from 3 to 8 carbon atoms.

The aryl group (1) is a substituent derived from an aromatic compound, such as a phenyl group or a naphthyl group. While the term "aromatic compound" as noted above includes heterocyclic aromatic compounds, the substituent derived from aromatic hydrocarbon compounds are especially preferable aryl groups for the present invention.

The heterocyclic group (2) is a substituent derived from a heterocyclic compound, preferably a nitrogen-containing heterocyclic compound. While the term "nitrogen-containing heterocyclic compound" as noted above includes aromatic ones, partially saturated ones, saturated ones, the heterocyclic group as Q is preferably the one derived from an aromatic nitrogen-containing heterocyclic compound, such as pyrrole, imidazole, pyrazole, pyridine, pyridazine, pyrimidine, pyrazine, indole, quinoline, isoquinoline, cinnoline, phthalazine, quinazoline, quinoxaline, naphthylidene, pyridopyridines, carbazole, carboline, phenanthridine, and acridine. Preferred of these nitrogen-containing aromatic heterocyclic groups are pyridyl, pyrimidyl and isoquinolyl groups.

Besides the nitrogen-containing heterocyclic group, the heterocyclic group (2) includes those containing an oxygen atom or a sulfur atom, which may be saturated, partially saturated or aromatic. Examples are thienyl, benzothienyl, furyl, furanyl, benzofuranyl, and chromenyl groups, with a benzofuranyl group and a dihydrobenzofuranyl group being preferred.

Additionally, the heterocyclic group (2) may be a heterocyclic group containing two or more different hetero atoms, such as an isothiazolyl group, an isoxazolyl group or an oxazinyl group.

The diarylmethyl group (3) is a substituent in which two hydrogen atoms of a methyl group are each replaced by an aryl group. The aryl group is selected from those enumerated above. The most typical diarylmethyl group is a diphenylmethyl group.

The aralkyl group (4) is a substituent in which an alkylene group having from 1 to 6 carbon atoms is bonded at one end thereof to the above-mentioned aryl group, typically including a benzyl group and a phenethyl group.

The alkyl group (5), which contains from 1 to 8 carbon atoms, may have a straight chain structure or a branched structure.

The cycloalkyl group (6), which contains from 3 to 8 carbon atoms, includes a cyclopropyl group, a cyclobutyl group, a cyclopentyl group, a cyclohexyl group, and a cyclooctyl group.

Each of the substituents (1) to (6) mentioned above as Q, particularly the aryl group, heterocyclic group, and the aryl moiety of the diarylmethyl group, may be substituted with one or more substituents selected from the following groups.

1. An alkyl group having from 1 to 6 carbon atoms, which may be straight or branched, or cyclic.

2. An alkoxyl group having from 1 to 6 carbon atoms, the alkyl moiety of which may be straight, branched or cyclic.

3. A trifluoromethyl group and a 2,2,2-trifluoroethyl group.

4. A trifluoromethoxyl group and a 2,2,2-trifluoroethoxyl group.

5. An alkylthio group composed of an alkyl group having from 1 to 6 carbon atoms and a sulfur atom as represented by a structural formula:

alkyl—S—, the alkyl group of which may be straight, branched or cyclic.

6. An alkylsulfinyl group derived from the above-mentioned alkylthio group by oxidizing the sulfur atom with one oxygen atom as represented by a structural formula:

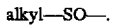
alkyl—SO—.

7. An alkylsulfonyl group derived from the above-mentioned alkylthio group by oxidizing the sulfur atom with two oxygen atoms as represented by a structural formula:

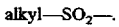
alkyl—SO$_2$—.

8. An alkanoyl group derived from an aliphatic carboxylic acid by removing the hydroxyl group from the carboxyl group thereof, as represented by a structural formula:

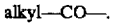
alkyl—CO—.

9. An alkanoyloxy group derived from oxygen and the above-mentioned alkanoyl group or by hydrogen removal from the carboxyl group of an aliphatic carboxylic acid, as represented by a structural formula:

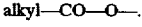
alkyl—CO—O—.

10. An alkanoylamino group derived by replacing one of the two hydrogen atoms of an amino group with an alkanoyl group, as represented by a structural formula:

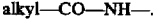
alkyl—CO—NH—.

11. An amino group.

12. A monoalkylamino group derived by replacing one of the two hydrogen atoms of an amino group with an alkyl group.

13. A dialkylamino group derived by replacing each of the two hydrogen atoms of an amino group with an alkyl group.

14. A hydroxyl group.

15. A halogen atom.

16. A perfluoroalkyl group composed of a straight chain, branched or cyclic alkyl group with all the hydrogen atoms replaced with fluorine atoms.

17. A cyano group.

18. A nitro group.

19. A carboxyl group.

20. An alkoxycarbonyl group composed of a straight chain, branched or cyclic alkyl group and a carbonyl group, connected via an oxygen atom, as represented by a structural formula:

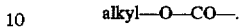
alkyl—O—CO—.

21. A tetrazolyl group, a 5-membered heterocyclic group.
22. A sulfamoyl group.
23. A methylenedioxy group, an ethylenedioxy group, and a propylenedioxy group, represented by a structural formula:

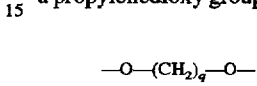
—O—(CH$_2$)$_q$—O— wherein q is 1, 2 to 3, and the carbon atoms (where q is 2 or 3) to which the two oxygen atoms are each bonded are adjacent to each other.

24. A morpholinosulfonyl group, represented by a structural formula:

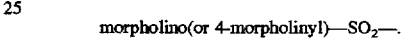
morpholino(or 4-morpholinyl)—SO$_2$—.

25. A piperazinosulfonyl group, represented by a structural formula:

(1-piperazinyl)—SO$_2$—.

26. A 4-alkylpiperazinosulfonyl group composed of 4-alkyl-piperazinyl group and sulfonyl group wherein the alkyl group at 4-position has from 1 to 6 carbon atoms, represented by a structural formula:

(4-alkyl-piperazin-1-yl)—SO$_2$—.

27. A 4-dialkylaminopiperidino group; a piperidine group having a dialkylamino group at 4-position thereof, wherein each of the alkyl moiety of the dialkylamino group has from 1 to 6 carbon atoms independently.

28. A 4-monoalkylaminopiperidino group; a piperidine group having an alkylamino group at 4-position thereof, wherein the alkyl moiety of the alkylamino group has from 1 to 6 carbon atoms.

29. A 4-aminopiperidino group; a piperidine group having an amino group at 4-position thereof.

Where the group Q has two or more substituents, the plural substituents may be the same or different.

These substituents may be on the alkyl group (or moiety) or cycloalkyl group (or moiety) of Q.

To the other nitrogen atom of the piperazine moiety is bonded a partial structure R (i.e., (1) a bicyclic nitrogen-containing heterocyclic group or (2) a phenyl group) via a connecting group Z (i.e., (1) an alkylene group having from 1 to 3 carbon atoms, (2) an alkenylene group having from 2 to 4 carbon atoms, (3) an alkylene group having from 1 to 3 carbon atoms and one hydroxyl group, (4) a carbonyl group, (5) an alkylene group having one or two carbon atoms and containing one carbonyl group at the end or middle of the carbon chain thereof, or (6) an oxalyl group).

The alkylene group (1) as Z is represented by a structural formula:

—(CH$_2$)$_r$—, wherein r is 1, 2, or 3.

The alkenylene group (2) as Z has one carbon-carbon double bond either at the terminal or in the middle of the carbon chain.

The alkylene group (3) having one hydroxyl group and from 1 to 3 carbon atoms has its hydroxyl group bonded to either the terminal or the middle of the carbon chain.

The carbonyl group (4) has a structural formula:

—CO—.

The alkylene group (5) having one carbonyl group at the end or in the middle of the carbon chain has a structural formula:

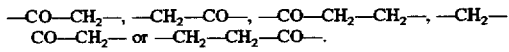

—CO—CH$_2$—, —CH$_2$—CO—, —CO—CH$_2$—CH$_2$—, —CH$_2$—CO—CH$_2$— or —CH$_2$—CH$_2$—CO—.

The oxalyl group (6) has a structural formula:

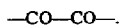

—CO—CO—.

The partial structure as R is (1) a bicyclic nitrogen-containing heterocyclic group having substituents $R^1$ and $R^2$ as defined herein or (2) a phenyl group.

The bicyclic heterocyclic group having substituents $R^1$ and $R^2$ as defined herein (1) as R is structurally characterized in that: (i) a 6-membered ring and a 5-membered ring are fused, (ii) there are one or two nitrogen atoms, which is/are on the 5-membered ring, (iii) the nitrogen-containing ring may be an aromatic ring or a saturated ring, and (iv) where the ring containing the nitrogen atom(s) is saturated, that ring may contain a ketone moiety.

The bicyclic heterocyclic group having such structural characteristics (i) to (iv) includes those derived from indole, isoindole, indazole, and benz[d]imidazole. Those having a nitrogen atom between two condensed rings, such as those derived from indolizine, benzo[a]pyrazole, benzo[e]pyrazole, benz[a]imidazole and benz[e]imidazole, are also included. The bicyclic nitrogen-containing heterocyclic group (1) is bonded to the connecting group, Z, at the nitrogen atom or carbon atom of the 5-membered ring thereof.

Specific examples of the bicyclic heterocyclic group (1) as R are indol-1-yl, indol-2-yl, indol-3-yl, 2,3-dihydroindol-1-yl, 2,3-dihydroindol-2-yl, 2,3-dihydroindol-3-yl, 3H-indol-2-yl, 3H-indol-3-yl, 2-oxoindol-1-yl, 2-oxoindol-3-yl, indazol-1-yl, indazol-3-yl, 2,3-dihydroindazol-1-yl, 2,3-dihydroindazol-2-yl, 2,3-dihydroindazol-3-yl, 3H-indazol-3-yl, 2,3-dihydro-3-oxoindazol-1-yl, 2,3-dihydro-3-oxoindazol-2-yl, isoindol-1-yl, isoindol-2-yl, isoindol-3-yl, 1,3-dihydroisoindol-1-yl, 1,3-dihydroisoindol-2-yl, 1,3-dihydroisoindol-3-yl, 1,3-dihydro-3-oxoisoindol-1-yl, 1,3-dihydro-3-oxoisoindol-2-yl, 1,3-dihydro-1-oxoisoindol-2-yl, 1,3-dihydro-1-oxoisoindol-3-yl, benz[d]imidazol-1-yl, benz[d]imidazol-2-yl, 2,3-dihydrobenz[d]imidazol-1-yl, 2,3-dihydrobenz[d]imidazol-2-yl, and 2,3-dihydro-2-oxobenz[d]imidazol-1-yl groups.

The bicyclic nitrogen-containing heterocyclic group (1) or phenyl group (2) as R is substituted with one or more substituents selected from the following groups. The two or more substituents may be the same or different. The. substituent of the phenyl group (2) is preferably on the carbon atom adjacent to the carbon atom bonded to Z. The substituent of the bicyclic nitrogen-containing heterocyclic group (1) is preferably on the nitrogen atom or carbon atom of the nitrogen-containing 5-membered ring.

1. A straight chain, branched or cyclic alkyl group having from 1 to 6 carbon atoms.
2. A substituted or unsubstituted phenyl group.
3. A benzoyl group the phenyl moiety of which may be substituted.
4. A benzylcarbonyl group the phenyl moiety of which may be substituted.
5. A benzoylmethyl group the phenyl moiety of which may be substituted.
6. An α-hydroxybenzyl group the phenyl moiety of which may be substituted.
7. A substituted or unsubstituted 5-membered aromatic heterocyclic group containing a nitrogen atom, an oxygen atom or a sulfur atom as a hetero atom (wherein a nitrogen atom is present as a hetero atom, this has a hydrogen atom or an alkyl group having from 1 to 6 carbon atoms, or it is the site for bonding to the bicyclic nitrogen-containing heterocyclic group (1) or phenyl group (2)), such as a pyrrolyl group, a furyl group or a thienyl group. This substituent may be bonded to the bicyclic nitrogen-containing heterocyclic group (1) or phenyl group (2) at any of possible sites thereof.
8. A substituted or unsubstituted 5-membered aromatic heterocyclic group containing one nitrogen atom and, as a second hetero atom, a nitrogen atom, an oxygen atom or a sulfur atom (wherein a nitrogen atom is present as the second hetero atom, this has a hydrogen atom or an alkyl group having from 1 to 6 carbon atoms, or it is the site of bonding to the bicyclic nitrogen-containing heterocyclic group (1) or phenyl group (2)), such as a pyrazolyl group, an imidazolyl group, a thiazolyl group, an isothiazolyl group, an oxazolyl group, or an isoxazolyl group. This substituent may be bonded to the bicyclic nitrogen-containing heterocyclic group (1) or phenyl group (2) at any of possible sites thereof.
9. A substituted or unsubstituted 5-membered aromatic heterocyclic group containing two nitrogen atoms and, as a third hetero atom, a nitrogen atom, an oxygen atom or a sulfur atom (wherein a nitrogen atom is present as the third hetero atom, this has a hydrogen atom or an alkyl group having from 1 to 6 carbon atoms, or it is the site of bonding to the bicyclic nitrogen-containing heterocyclic group (2) or phenyl group (2)), such as a 1,2,3-triazolyl group, a 1,2,4-triazolyl group, a 1,2,3-thiadiazyl group, a 1,2,4-thiadiazyl group, a 1,2,5-thiadiazyl group, a 1,3,4-thiadiazyl group, a 1,2,3-oxadiazyl group, a 1,2,4-oxadiazyl group, a 1,2,5-oxadiazyl group, or a 1,3,4-oxadiazyl group. This substituent may be bonded to the bicyclic nitrogen-containing heterocyclic group (1) or phenyl group (2) at any of possible sites thereof.
10. A substituted or unsubstituted 6-membered aromatic heterocyclic ring containing one or two nitrogen atoms, such as a pyridyl group, a pyridazinyl group, a pyrimidyl group, or a pyrazinyl group. This substituent may be bonded to the bicyclic nitrogen-containing heterocyclic group (1) or phenyl group (2) at any of possible sites thereof.
11. A heterocyclic group-substituted alkyl group composed of a substituted or unsubstituted 5-membered aromatic heterocyclic group containing a nitrogen atom, an oxygen atom or a sulfur atom as a hetero atom and an alkylene group having from 1 to 3 carbon atoms (wherein a nitrogen atom is present as a hetero atom, this has a hydrogen atom or an alkyl group having from 1 to 6 carbon atoms), such as a pyrrolyl-substituted methyl, ethyl or propyl group, a thienyl-substituted methyl, ethyl or propyl group, or a furyl-substituted methyl, ethyl or propyl group. The alkylene group may be bonded to any of possible sites of the heterocyclic ring.

12. A heterocyclic group-substituted alkyl group composed of a substituted or unsubstituted 5-membered aromatic heterocyclic ring containing one nitrogen atom as a first hetero atom and, as a second hetero atom, a nitrogen atom, an oxygen atom or a sulfur atom and an alkylene group having from 1 to 3 carbon atoms (wherein a nitrogen atom is present as the second hetero atom, this has a hydrogen atom or an alkyl group having from 1 to 6 carbon atoms or is bonded to the alkylene group), such as a pyrazolyl-substituted methyl, ethyl or propyl group, an imidazolyl-substituted methyl, ethyl or propyl group, a thiazolyl-substituted methyl, ethyl or propyl group, or an oxazolyl-substituted methyl, ethyl or propyl group. The alkylene group may be bonded to any of possible sites of the heterocyclic ring.

13. A heterocyclic group-substituted alkyl group composed of a substituted or unsubstituted 5-membered aromatic heterocyclic ring containing two nitrogen atoms as first and second hetero atoms and, as a third hetero atom, a nitrogen atom, an oxygen atom or a sulfur atom and an alkylene group having from 1 to 3 carbon atoms (wherein a nitrogen atom is present as the third hetero atom, this has a hydrogen atom or an alkyl group having from 1 to 6 carbon atoms or is bonded to the alkylene group), such as a 1,2,3-triazolyl-substituted methyl, ethyl or propyl group, a 1,2,4-triazolyl-substituted methyl, ethyl or propyl group, a 1,2,3-thiadiazyl-substituted methyl, ethyl or propyl group, a 1,2,4-thiadiazyl-substituted methyl, ethyl or propyl group, a 1,2,5-thiadiazyl-substituted methyl, ethyl or propyl group, a 1,3,4-thiadiazyl-substituted methyl, ethyl or propyl group, a 1,2,3-oxadiazyl-substituted methyl, ethyl or propyl group, a 1,2,4-oxadiazyl-substituted methyl, ethyl or propyl group, a 1,2,5-oxadiazyl-substituted methyl, ethyl or propyl group, or a 1,3,4-oxadiazyl-substituted methyl, ethyl or propyl group. The alkylene group may be bonded to any of possible sites of the heterocyclic ring.

14. A heterocyclic group-substituted alkyl group composed of a substituted or unsubstituted 6-membered aromatic heterocyclic ring containing one or two nitrogen atoms and an alkylene group having from 1 to 3 carbon atoms, such as a pyridyl-substituted methyl, ethyl or propyl group, a pyridazinyl-substituted methyl, ethyl or propyl group, a pyrimidyl-substituted methyl, ethyl or propyl group, or a pyrazinyl-substituted methyl, ethyl or propyl group. The alkylene group may be bonded to any of possible sites of the heterocyclic ring.

15. A phenylhydroxyalkyl group composed of an alkylene group having one hydroxyl group and 2 to 3 carbon atoms and a substituted or unsubstituted phenyl group, such as a 1-hydroxy-2-phenylethyl group, a 2-hydroxy-2-phenylethyl group, a 1-hydroxy-3-phenylpropyl group, a 2-hydroxy-3-phenylpropyl group or a 3-hydroxy-3-phenylpropyl group.

16. A 2-phenylethynyl group wherein the phenyl group may be substituted.

17. A tetrazolyl group.

18. A morpholino group.

19. An alkanoylamino group having from 2 to 7 carbon atoms.

20. A tetrazolylalkyl group composed of a tetrazolyl group and an alkylene group having from 1 to 3 carbon atoms, wherein the alkylene group is bonded to the carbon atom or nitrogen atom of the tetrazolyl group, such as a tetrazolylmethyl group, a tetrazolylethyi group or a tetrazolylpropyl group.

21. A morpholinoalkyl group composed of a morpholino group and an alkylene group having from 1 to 3 carbon atoms, such as a morpholinomethyl group, a morpholinoethyl group or a morpholinopropyl group.

22. A 4-alkoxycarbonylcyclohexyl group having from 1 to 6 carbon atoms in the alkoxy moiety thereof, wherein the alkoxycarbonyl moiety and the bond at the 1-position may have a trans-structure or a cis-structure or may be in axial or equatorial positions.

23. An alkoxycarbonyl group having from 1 to 6 carbon atoms in the alkoxy moiety thereof.

24. An alkoxycarbonylalkyl group composed of an alkoxycarbonyl group having from 1 to 6 carbon atoms in the alkoxy moiety thereof and an alkylene group having from 1 to 3 carbon atoms, such as an alkoxycarbonylmethyl group, an alkoxycarbonylethyl group or an alkoxycarbonylpropyl group.

25. A 1-alkylindol-2-yl group wherein the alkyl moiety has from 1 to 6 carbon atoms and the indole ring may further be substituted.

26. A substituted or unsubstituted pyrrolidone-1-yl group wherein the oxo moiety is at the 2- or 3-position, and the pyrrolidine moiety may be substituted, especially by alkyl group(s).

27. A 2-guanidinothiazolyl group.

28. A (2-guanidinothiazolyl)-alkyl group composed of a 2-guanidinothiazolyl group and an alkylene group having from 1 to 3 carbon atoms.

29. A substituted or unsubstituted 1,4-dihydropyridyl group wherein the substituent includes an alkyl group and a carboxyl group, such as a 2,6-bis(methoxycarbonyl)-3,5-dimethyl-1,4-dihydropyridyl group.

30. A 4-alkyl-piperazino-alkyl group composed of a 4-alkyl-piperazine having an alkyl group of from 1 to6 carbon atom and an alkylene group of from 1 to 6 carbon atoms. The examples are; a 4-methylpiperazinomethyl group, a 4-ethylpiperazinomethyl group, a 4-propylpiperazinomethyl group, a 2-(4-methylpiperazino) ethyl group, a 2-(4-ethylpiperazino)ethyl group and a 2-(4-propylpiperazino)-ethyl group, and the like.

31. A 4-(morpholinosulfonyl)phenylalkyl group composed of 4-(morpholinosulfonyl)phenyl group and an alkylene group of from 1 to 6 carbon atoms. The examples are; a 4-(morpholinosulfonyl)phenylmethyl group, a 2-[4-(morpholinosulfonyl)phenyl]ethyl group, a 3-[4-(morpholinosulfonyl)phenyl]propyl group, and the like.

32. A 4-(piperazinosulfonyl)phenylalkyl group composed of 4-(piperazinosulfonyl)phenyl group and an alkylene group of from 1 to 6 carbon atoms. The examples are; a 4-(piperazinosulfonyl)phenylmethyl group, a 2-[4-(piperazinosulfonyl)phenyl]ethyl group, a 3-[4-(piperazinosulfonyl)phenyl]propyl group, and the like.

33. A 4-(4-alkylpiperazinosulfonyl)phenylalkyl group composed of 4-(4-alkylpiperazinosulfonyl)phenyl group, wherein the alkyl group on piperazino group is that of from 1 to 6 carbon atoms, and an alkylene group of from 1 to 6 carbon atoms. The examples are; a 4-(4-methylpiperazinosulfonyl)phenylmethyl group, a 2-[4-(4-methylpiperazinosulfonyl)phenyl]ethyl group, a 3-[4-(4-methylpiperazinosulfonyl)phenyl]propyl group, and the like.

34. An alkoxycarbonylalkyl group composed of an alkoxy group of from 1 to 6 carbon atoms and a carbonyl group and an alkylene group of from 1 to 6 carbon atoms. The examples are; a methoxycarbonylmethyl group, an ethoxycarbonyl-methyl group, a propoxycarbonylmethyl group, a 2-(methoxycarbonyl)ethyl group, a 2-(ethoxycarbonyl)ethyl group, a 2-(propoxycarbonyl)ethyl group, and the like.

35. A carboxyalkyl group composed of a carboxyl group and an alkylene group of from 1 to 6 carbon atoms. The examples are; a carboxymethyl group, a 2-carboxyethyethyl group, 3-carboxypropyl group, 4-carboxybutyl group, 5-carboxy-pentyl group and 6-carboxyhexyl group.

36. A 4-[(4-dialkylaminopiperidino)]phenylalkyl group composed of a phenyl group having a 4-dialkylamino-piperidino group, wherein the alkyl groups of dialkyl-amino group are those of from 1 to 6 carbon atoms independently, at 4-position and an alkylene group of from 1 to 6 carbon atoms. The examples are; a [4-(4-dimethylaminopiperidino) phenyl]methyl group, a 2-[4-(4-dimethylaminopiperidino) phenyl]ethyl group, a 3-[4-(4-dimethylaminopiperidino) phenyl]propyl group, a [4-[4-(N-methyl-N-ethylamino) piperidino]phenyl]methyl group, a [4-(4-diethylaminopiperidino)phenyl]methyl group, and the like.

37. A 4-[(4-monoalkylaminopiperidino)]phenylalkyl group composed of a phenyl group having a 4-monoalkylamino-piperidino group, wherein the alkyl group of monomethylamino group is that of from 1 to 6 carbon atoms, at 4-position and an alkylene group of from 1 to 6 carbon atoms. The examples are; a [4-(4-methylamino-piperidino)phenyl]methyl group, a 2-[4-(4-methylamino-piperidino)phenyl]ethyl group, a 3-[4-(4-methylamino-piperidino)phenyl]propyl group, a [4-(4-ethylamino-piperidino)phenyl]methyl group, a 2-[4-(4-ethylamino-piperidino)phenyl]ethyl group, a 3-[4-(4-ethylamino-piperidino)phenyl]propyl group, and the like.

38. A 4-[(4-aminopiperidino)]phenylalkyl group composed of a phenyl group having a 4-aminopiperidino group at 4-position and an alkylene group of from 1 to 6 carbon atoms. The examples are; a [4-(4-aminopiperidino)-phenyl] methyl group, a 2-[4-(4-aminopiperidino)phenyl]-ethyl group, a 3-[4-(4-aminopiperidino)phenyl]propyl group, and the like.

39. A (4-dialkylaminopiperidino)alkyl group composed of a 4-dialkylaminopiperidino group, wherein the alkyl groups of dialkylamino group are those of from 1 to 6 carbon atoms independently, and an alkylene group of from 1 to 6 carbon atoms. The examples are; a (4-dimethylamino-piperidino) methyl group, a 2-(4-dimethylaminopiperidino)-ethyl group, a 3-(4-dimethylaminopiperidino)propyl group, a 4-[(N-methyl-N-ethylamino)piperidino]methyl group, a (4-diethylaminopiperidino)methyl group, and the like.

40. A (4-alkylaminopiperidino)alkyl group composed of a 4-alkylaminopiperidino group, wherein the alkyl group of monomethylamino group is that of from 1 to 6 carbon atoms, and an alkylene group of from 1 to 6 carbon atoms. The examples are; a (4-methylaminopiperidino)methyl group, a 2-(4-methylaminopiperidino)ethyl group, a 3-(4-methylaminopiperidino)propyl group, a (4-ethylaminopiperidino)methyl group, a 2-(4-ethylaminopiperidino)-ethyl group, a 3-(4-ethylaminopiperidino)propyl group, and the like.

41. A (4-aminopiperidino)alkyl group composed of a 4-aminopiperidino group (4-aminopiperidin-1-yl group) and an alkylene group of from 1 to 6 carbon atoms. The examples are; a (4-aminopiperidino)methyl group, a 2-(4-aminopiperidino)ethyl group, a 3-(4-aminopiperidino)-propyl group, and the like.

42. A hydrogen atom.

Where the above-mentioned substituents 1 to 42 are substituted, they are substituted with one or more of the following groups which may be the same or different.

1. An alkyl group having from 1 to 6 carbon atoms.

2. An alkoxyl group having from 1 to 6 carbon atoms.

3. A trifluoromethyl group anna 2,2,2-trifluoroethyl group.

4. A trifluoromethoxyl group and a 2,2,2-trifluoroethoxyl group.

5. An alkylthio group having from 1 to 6 carbon atoms.

6. An alkylsulfinyl group having from 1 to 6 carbon atoms.

7. An alkylsulfonyl group having from 1 to 6 carbon atoms.

8. An alkanoyl group composed of an alkyl group having from 1 to 6 carbon atoms and a carbonyl group.

9. An alkanoyloxy group having from 2 to 7 carbon atoms.

10. An alkanoylamino group having from 2 to 7 carbon atoms.

11. An amino group.

12. A monoalkylamino group having from 1 to 6 carbon atoms.

13. A dialkylamino group having from 1 to 6 carbon atoms in each alkyl moiety thereof.

14. A hydroxyl group.

15. A halogen atom.

16. A perfluoroalkyl group having from 2 to 6 carbon atoms.

17. A cyano group.

18. A nitro group.

19. A carboxyl group.

20. An alkoxycarbonyl group composed of an alkoxyl group having from 1 to 6 carbon atoms and a carbonyl group.

21. A tetrazolyl group.

22. A sulfamoyl group.

23. A methylenedioxy group, an ethylenedioxy group, and a propylenedioxy group.

24. A morpholinosulfonyl group.

25. A piperazinosulfonyl group.

26. A 4-alkylpiperazinosulfonyl group having from 1 to 6 carbon atoms.

27. A 4-dialkylaminopiperidino group having from 1 to 6 carbon atoms in each alkyl moiety thereof.

28. A 4-monoalkylaminopiperidino group having from 1 to 6 carbon atoms in the alkyl moiety thereof.

29. A 4-aminopiperidino group.

A partial structure abbreviated as R for the compound of the present invention, a nitrogen-containing heterocyclic group is exemplified by the following formula:

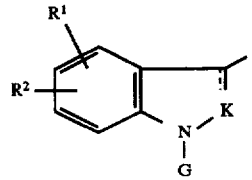

wherein $R^1$, $R^2$ and G are as defined before. K represents N, C or C=O, although, the substituent G may present at the 2-position of the indazole;

and a phenyl group is exemplified by the formula:

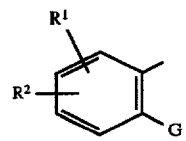

wherein $R^1$, $R^2$ and G are as defined before.

Among the nitrogen-containing heterocyclic group, indazole group of the following formula:

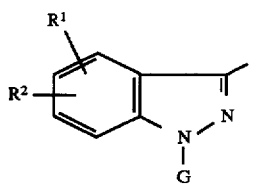

is a preferable one. The indazole group and the phenyl group is the favorable group as R, and the indazole group is more favorable between the two.

As for the substituent G, a substituent on the R, the preferable substituent G for the indazole group within those previously mentioned are:

an alkyl group having from 1 to 6 carbon atoms, a substituted or unsubstituted phenyl group, a benzoyl group with the phenyl moiety thereof substituted or unsubstituted, a benzylcarbonyl group with the phenyl moiety thereof substituted or unsubstituted, a benzolmethyl group with the phenyl moiety thereof substituted or unsubstituted, an α-hydroxybenzyl group with the phenyl moiety thereof substituted or unsubstituted, a substituted or unsubstituted 6-membered aromatic heterocyclic group containing one or two nitrogen atoms, a heterocyclic group substituted-alkyl group composed of a substituted or unsubstituted 5-membered aromatic heterocyclic group containing a nitrogen atom, an oxygen atom or a sulfur atom as a hetero atom and an alkylene group of from 1 to 3 carbon atoms, a heterocyclic group substituted-alkyl group composed of a substituted or unsubstituted 5-membered aromatic heterodyclic group containing one nitrogen atom and, a nitrogen atom, an oxygen atom or a sulfur atom as the second hetero atom and an alkylene group of from 1 to 3 carbon atoms, a heterocyclic group substituted-alkyl group composed of a substituted or unsubstituted 5-membered aromatic heterocyclic group containing two nitrogen atoms and, a nitrogen atom, an oxygen atom or a sulfur atom as thethird hetero atom and an alkylene group of from 1 to 3 carbon atoms, a heterocyclic group substituted-alkyl group composed of a substituted or unsubstituted 6-membered aromatic heterocyclic group containing one or two nitrogen atoms and an alkylene group of from 1 to 3 carbon atoms, a phenylhydroxyalkyl group composed of an alkylene group having one hydroxyl group and 2 to 3 carbon atoms and a substituted or unsubstituted phenyl group, a 2-phenylethenyl group wherein the phenyl group may be substituted, an alkanoylamino group having from 2 to 7 carbon atoms, a tetrazolylalkyl group composed of a tetrazolyl group and an alkylene group having from 1 to 3 carbon atoms wherein the alkylene group is bonded to the carbon atom or nitrogen atom of the tetrazolyl group, a morpholinoalkyl group composed of a morpholino group and an alkylene group having from 1 to 3 carbon atoms, an alkoxycarbonylalkyl group composed of from 1 to 6 carbon atoms in the alkyl moiety thereof and an alkylene group having from 1 to 3 carbon atoms, a substituted or unsubstituted pyrrolidon-1-yl group, a (2-guanidinothiazolyl)alkyl group composed of a 2-guanidinothiazolyl group and an alkylene group having from 1 to 3 carbon atoms, a substituted or unsubstituted 1,4-dihydropyridyl group, a (4-alkylpiperazino)alkyl group composed of a 4-alkylpiperazine having an alkyl group of from 1 to 6 carbon atoms and an alkylene group of from 1 to 6 carbon atoms, a [4-(morpholinosulfonyl)phenyl]alkyl group composed of 4-(morpholinosulfonyl)phenyl group and an alkylene group of from 1 to 6 carbon atoms, a [4-(piperazinosulfonyl)phenyl]alkyl group composed of 4-(piperazinosulfonyl)phenyl group and an alkylene group of from 1 to 6 carbon atoms, a [4-(4-alkylpiperazinosulfonyl)phenyl]alkyl group composed of 4-(4-alkylpiperazinosulfonyl)phenyl group wherein the alkyl group on piperazino group is that of from 1 to 6 carbon atoms, and an alkylene group oF from 1 to 6 carbon atoms, an alkoxycarbonylalkyl group composed of an alkoxyl group of from 1 to 6 carbon atoms and a carbonyl group and an alkylene group of from 1 to 6 carbon atoms, a carboxyalkyl group composed of a carboxyl group and an alkylene group of from 1 to 6 carbon atoms, a [4-(4-dialkylaminopiperidino)phenyl]alkyl group composed of a phenyl group having a 4-dialkylaminopiperidino group at-4-position, wherein each of the alkyl moiety of the dialkylamino group has from 1 to 6 carbon atoms independently, and an alkylene group of from 1 to 6 carbon atoms, a [4-(4-monoalkylaminopiperidino)phenyl]alkyl group composed of a phenyl group having a 4-monoalkylaminopiperidino group at 4-position, wherein the alkyl moiety of the monoalkylamino group has from 1 to 6 carbon atoms, and an alkylene group of from 1 to 6 carbon atoms, a [4-(4-aminopiperidino)phenyl]alkyl group composed of a phenyl group having a 4-aminopiperidino group at 4-position and an alkylene group of from 1 to 6 carbon atoms, a (4-dialkylaminopiperidino)alkyl group composed of a 4-dialkylaminopiperidino group, wherein each of the alkyl moiety of the dialkylamino group has from 1 to 6 carbon atoms independently, and an alkylene group of from 1 to 6 carbon atoms, a (4-alkylaminopiperidino)alkyl group composed of a 4-alkylaminopiperidino group, wherein the alkyl moiety of the monoalkylamino group has from 1 to 6 carbon atoms, and an alkylene group of from 1 to 6 carbon atoms, a (4-aminopiperidino)alkyl group composed of a 4-aminopiperidino group and an alkylene group of from 1 to 6 carbon atoms, a phenylalkyl group composed of a substituted or unsubstituted phenyl group and an alkylene group of from 1 to 6 carbon atoms, and a hydrogen atoms.

And further, the more preferable substituent G for indazole within those are:

a heterocyclic group substituted-alkyl group composed of a substituted or unsubstituted 5-membered aromatic heterocyclic group containing a nitrogen atom, an oxygen atom or a sulfur atom as a hetero atom and an alkylene group of from 1 to 3 carbon atoms, a heterocyclic group substituted-alkyl group composed of a substituted or unsubstituted 5-membered aromatic heterocyclic group containing one nitrogen atom and, a nitrogen atom, an oxygen atom or a sulfur atom as the second hetero atom and an alkylene group of from 1 to 3 carbon atoms, a heterocyclic group substituted-alkyl group composed of a substituted or unsubstituted 5-membered aromatic heterocyclic group containing two nitrogen atoms and, a nitrogen atom, an oxygen atom or a sulfur atom as the third hetero atom and an alkylene group of from 1 to 3 carbon atoms, a heterocyclic group substituted-alkyl group composed of a substituted or unsubstituted 6-membered aromatic heterocyclic group containing one or two nitrogen atoms and an alkylene group of from 1 to 3 carbon atoms, a tetrazolylalkyl group, a (2-guanidinothiazolyl)alkyl group, a [4-(morpholinosulfonyl)phenyl]alkyl group, a [4-(piperazinosulfonyl)phenyl]alkyl group, a [4-(4-alkylpiperazinosulfonyl)phenyl]alkyl group, an alkoxycarbonylalkyl group, a carboxyalkyl group, a [4-(4-dialkylaminopiperidino)phenyl]alkyl group, a [4-(4-monoalkylaminopiperidino)phenyl]alkyl group, a [4-(4-aminopiperidino)phenyl]alkyl group, a (4-dialkylaminopiperidino)alkyl group, a (4-alkylaminopiperidino)alkyl group, a (4-aminopiperidino)alkyl group, a phenylalkyl group, and a hydrogen atom.

Further, the especially preferable substituent G for indazole is a heterocyclic group substituted-alkyl group or a phenylalkyl group.

One of the preferable substituent G for indazole is an aralkyl group composed of an aryl group and an alkylene group of from 1 to 6 carbon atoms. As for the aryl group of the aralkyl group, not only those derived from the aromatic hydrocarbon, but the aromatic heterocyclic group are included. The examples of the aralkyl group are: an α-hydroxybenzyl group; a heterocyclic group substituted-alkyl group composed of a 5-membered aromatic heterocyclic group containing a nitrogen atom, an oxygen atom or a sulfur atom as a hetero atom and an alkylene group; a heterocyclic group substituted-alkyl group composed of a 5-membered aromatic heterocyclic group containing one nitrogen atom and, a nitrogen atom, an oxygen atom or a sulfur atom as the second hetero atom and an alkylene group; a heterocyclic group substituted-alkyl group composed of a 5-membered aromatic heterocyclic group containing two nitrogen atoms and, a nitrogen atom, an oxygen atom or a sulfur atom as the third hetero atom and an alkylene group; a heterocyclic group substituted-alkyl group composed of a 6-membered aromatic heterocyclic group containing one or two nitrogen atoms and an alkylene group; a phenylhydroxyalkyl group composed of an alkylene group having one hydroxyl group and 2 to 3 carbon atoms and a phenyl group; a 2-phenylethenyl group; a tetrazolylalkyl group composed of a tetrazolyl group and an alkylene group; a (2-guanidinothiazolyl)alkyl group composed of a 2-guanidinothiazolyl group and an alkylene group; a [4-(morpholinosulfonyl)phenyl]alkyl group composed of 4-(morpholinosulfonyl)phenyl group and an alkylene group; a [4-(piperazinosulfonyl)phenyl]alkyl group composed of 4-(piperazinosulfonyl)phenyl group and an alkylene group; a [4-(4-alkylpiperazinosulfonyl)phenyl]alkyl group composed of 4-(4-alkylpiperazinosulfonyl)phenyl group and an alkylene group; a [4-(4-dialkylaminopiperidino)phenyl] alkyl group composed of a 4-(4-dialkylaminopiperidino) phenyl group and an alkylene group; a [4-(4-monoalkylaminopiperidino)phenyl]alkyl group composed of a 4-(4-monoalkylaminopiperidino)phenyl group and an alkylene group; a [4-(4-aminopiperidino)-phenyl]alkyl group composed of a 4-(aminopiperidino)phenyl group and an alkylene group; a phenylalkyl group composed of a phenyl group and an alkylene group.

Among the aralkyl group, these having one or two alkylene chain are more preferable. And further, those having one carbon chain, i.e., the arylmethyl group, are more preferable within the two. As for the arylmethyl group, both heteroarylmethyl group and arylmethyl group are favorable.

A preferable substituent for indazole such as $R^1$ and $R^2$ within those previously mentioned is:

an alkoxyl group of from 1 to 6 carbon atoms; a trifluoromethoxyl group; a 2,2,2-trifluoroethoxyl group; an alkylthio group having from 1 to 6 carbon atoms; an alkylsulfinyl group having from 1 to 6 carbon atoms; an alkylsulfonyl group having from 1 to 6 carbon atoms; an alkanoyl group composed of an alkyl group having from 1 to 6 carbon atoms and a carbonyl group; an alkanoylamino group having from 2 to 7 carbon atoms; a monoalkylamino group having from 1 to 6 carbon atoms in the alkyl moiety thereof; a dialkylamino group having from 1 to 6 carbon atoms in each alkyl moiety thereof; a hydroxyl group; a halogen atom; a carboxyl group; an alkoxycarbonyl group composed of an alkoxy group having from 1 to 6 carbon atoms and a carbonyl group; a tetrazolyl group; a sulfamoyl group; a methylenedioxy group; an ethylenedioxy group; a morpholinosulfonyl group; a piperazinosulfonyl group; a 4-alkylpiperazinosulfonyl group having from 1 to 6 carbon atoms; a 4-dialkylaminopiperidino group having from 1 to 6 carbon atoms in each alkyl moiety thereof; a 4-monoalkylaminopiperidino group having from 1 to 6 carbon atoms in the alkyl moiety thereof; and a 4-aminopiperidino group.

Within those, the more preferable substituent for indazole is:

an alkoxyl group of from 1 to 6 carbon atoms; a trifluoromethoxyl group; a 2,2,2-trifluoroethoxyl group; a hydroxyl group; a halogen atom, especially a fluorine atom; a tetrazolyl group; a sulfamoyl group; a methylenedioxy group; an ethylenedioxy group; a morpholinosulfonyl group; a piperazinosulfonyl group; a 4-alkylpiperazinosulfonyl group having from 1 to 6 carbon atoms; a 4-dialkylaminopiperidino group having from 1 to 6 carbon atoms in each alkyl moiety thereof; a 4-monoalkylaminopiperidino group having from 1 to 6 carbon atoms in the alkyl moiety thereof; and a 4-aminopiperidino group.

The especially preferable substituent for indazole is: an alkoxyl group of from 1 to 6 carbon atoms; a halogen atom, especially a fluorine atom; a tetrazolyl group; a sulfamoyl group; a methylenedioxy group; and an ethylenedioxy group.

As for the substituent G on the phenyl group, the preferable ones within the previously mentioned substituents are:

a substituted or unsubstituted phenyl group, a substituted of unsubstituted 5-membered aromatic heterocyclic group containing a nitrogen atoms, an oxygen atom or a sulfur atom as a hetero atom, a substituted or unsubstituted 5-membered aromatic heterocyclic group containing one nitrogen atom and, a nitrogen atom, an oxygen atom or a sulfur atom as the second hetero atom, a substituted or unsubstituted 5-membered aromatic heterocyclic group containing two nitrogen atoms and, a nitrogen atom, an oxygen atom or a sulfur atom as the third hetero atom, a substituted or unsubstituted 6-membered aromatic heterocyclic group containing one or two nitrogen atoms, a tetrazolyl group, a 1-alkylindol-2-yl group having from 1 to 6 carbon atoms in the alkyl moiety thereof wherein the indole moiety may further be substituted, a 2-guanidinothiazolyl group, and a substituted or unsubstituted 1,4-dihydropyridyl group.

In case when the substituent R is a phenyl group, an aryl group is preferable for the substituent G. And this case, again, not only those derived from the aromatic hydrocarbon, but the aromatic heterocyclic group are preferable for G.

In case when the substituent R is a phenyl group, the preferable substituent for the phenyl group such as $R^1$ and $R^2$ is the same as those previously explained for indazole.

An example of the most preferable substituent R is 1H-indazole group having two methoxy groups or a methylenedioxy group, or a phenyl group having two methoxy groups or a methylenedioxy group.

As for the substituent Q, the aryl group is preferable among the previously mentioned substituents. Within the aryl group, a phenyl group is preferable. And further, the phenyl group having at least one substituent at the meta-position of the connecting position of the phenyl group to the piperazine moiety is preferable. A halogen atom, especially a chlorine atom, and a trifluoromethyl group are the suitable substituents for the meta-substituent. In case when the meta-substituent is halogen atom, an alkyl group is preferable for the second substituent on the phenyl group. And for the trifluoromethyl group, an alkoxyl group is a preferable one.

The present inventors consider an electron attractive substituent is suitable for the meta-substituent, and an electron donative substituent is suitable for the second substituent.

As for the connecting group Z, an alkylene group is preferable among the previously mentioned groups. And those having two or three carbon atoms are more preferable.

The examples of the preferable compounds are:

3-[2-[4-(3-chloro-2-methylphenyl)-1-piperazinyl]ethyl]-5,6-dimethoxy-1-(3,4-dimethoxybenzyl)-1H-indazole or a salt thereof;

3-[2-[4-(3-chloro-2-methylphenyl)-1-piperazinyl]ethyl]-5,6-methylenedioxy-1-(3,4-dimethoxybenzyl)-1H-indazole or a salt thereof;

3-[2-[4-(3-chloro-2-methylphenyl)-1-piperazinyl]ethyl]-5,6-dimethoxy-1-(4-imidazolylmethyl)-1H-indazole or a salt thereof;

3-[2-[4-(3-chloro-2-methylphenyl)-1-piperazinyl]ethyl]-5,6-methylenedioxy-1-(4-imidazolylmethyl)-1H-indazole or a salt thereof;

3-[2-[4-(3-chloro-2-methylphenyl)-1-piperazinyl]ethyl]-5,6-dimethoxy-1-(2-pyridylmethyl)-1H-indazole or a salt thereof;

3-[2-[4-(3-chloro-2-methylphenyl)-1-piperazinyl]ethyl]-5,6-methylenedioxy-1-(2-pyridylmethyl)1H-indazole or a salt thereof;

3-[2-[4-(3-chloro-2-methylphenyl)-1-piperazinyl]ethyl]-5,6-dimethoxy-1-(3-pyridylmethyl)-1H-indazole or a salt thereof;

3-[2-[4-(3-chloro-2-methylphenyl)-1-piperazinyl]ethyl]-5,6-methylenedioxy-1-(3-pyridylmethyl)-1H-indazole or a salt thereof;

3-[2-[4-(3-chloro-2-methylphenyl)-1-piperazinyl]ethyl]-5,6-dimethoxy-1-(4-pyridylmethyl)-1H-indazole or a salt thereof;

3-[2-[4-(3-chloro-2-methylphenyl)-1-piperazinyl]ethyl]-5,6-methylenedioxy-1-(4-pyridylmethyl)-1H-indazole or a salt thereof;

3-[2-[4-(3-chloro-6-methoxyphenyl)-1-piperazinyl]ethyl]-5,6-dimethoxy-1,3,4-dimethoxybenzyl)-1H-indazole or a salt thereof;

3-[2-[4-(3-chloro-6-methoxyphenyl)-1-piperazinyl]ethyl]-5,6-methylenedioxy-1-(3,4-dimethoxybenzyl)-1H-indazole or a salt thereof;

3-[2-[4-(3-trifluoromethylphenyl)-1-piperazinyl]ethyl]-5,6-dimethoxy-1-(3,4-dimethoxybenzyl)-1H-indazole or a salt thereof;

3-[2-[4-(3-trifluoromethylphenyl)-1-piperazinyl]ethyl]-5,6-methylenedioxy-1-(3,4-dimethoxybenzyl)-1H-indazole or a salt thereof;

5,6-dimethoxy-2-[[4,5-dimethoxy-2-[4-(2-methoxyphenyl)-1-piperazinyl]ethyl]phenyl]-1-methylindole or a salt thereof;

5,6-dimethoxy-2-[[4,5-methylenedioxy-2-[4-(2-methoxyphenyl)-1-piperazinyl]ethyl]phenyl]-1-methylindole or a salt thereof;

1-(3-chloro-2-methylphenyl)-4-[2-[[4,5-dimethoxy-2-(3,4-dimethoxyphenyl)]phenyl]ethyl]piperazine or a salt thereof;

1-(3-chloro-2-methylphenyl)-4-[2-[[4,5-methylenedioxy-2-(3,4-dimethoxyphenyl)]phenyl]ethyl]piperazine or a salt thereof;

3-[2-[4-(3-chloro-2-methylphenyl)-1-piperazinyl]propyl]-5,6-dimethoxy-1-(3,4-dimethoxybenzyl)-1H-indazole or a salt thereof;

3-[2-[4-(3-chloro-2-methylphenyl)-1-piperazinyl]propyl]-5,6-methylenedioxy-1-(3,4-dimethoxybenzyl)-1H-indazole or a salt thereof;

3-[2-[4-(3-chloro-2-methylphenyl)-1-piperazinyl]propyl]-5,6-dimethoxy-1-(4-imidazolylmethyl)-1H-indazole or a salt thereof;

3-[2-[4-(3-chloro-2-methylphenyl)-1-piperazinyl]propyl]-5,6-methylenedioxy-1-(4-imidazolylmethyl)-1H-indazole or a salt thereof;

3-[2-[4-(3-chloro-2-methylphenyl)-1-piperazinyl]propyl]-5,6-dimethoxy-1-(2-pyridylmethyl)-1H-indazole or a salt thereof;

3-[2-[4-(3-chloro-2-methylphenyl)-1-piperazinyl]propyl]-5,6-methylenedioxy-1-(2-pyridylmethyl)-1H-indazole or a salt thereof;

3-[2-[4-(3-chloro-2-methylphenyl)-1-piperazinyl]propyl]-5,6-dimethoxy-1-(3-pyridylmethyl)-1H-indazole or a salt thereof;

3-[2-[4-(3-chloro-2-methylphenyl)-1-piperazinyl]propyl]-5,6-methylenedioxy-1-(3-pyridylmethyl)-1H-indazole or a salt thereof;

3-[2-[4-(3-chloro-2-methylphenyl)-1-piperazinyl]propyl]-5,6-dimethoxy-1-(4-pyridylmethyl)-1H-indazole or a salt thereof;

3-[2-[4-(3-chloro-2-methylphenyl)-1-piperazinyl]propyl]-5,6-methylenedioxy-1-(4-pyridylmethyl)-1H-indazole or a salt thereof;

3-[2-[4-(3-chloro-6-methoxyphenyl)-1-piperazinyl]propyl]-5,6-dimethoxy-1-(3,4-dimethoxybenzyl)-1H-indazole or a salt thereof;

3-[2-[4-(3-chloro-6-methoxyphenyl)-1-piperazinyl]propyl]-5,6-methylenedioxy-1-(3,4-dimethoxybenzyl)-1H-indazole or a salt thereof;

3-[2-[4-(3-trifluoromethylphenyl)1-piperazinyl]propyl]-5,6-dimethoxy-1-(3,4-dimethoxybenzyl)-1H-indazole or a salt thereof;

3-[2-[4-(3-trifluoromethylphenyl)-1-piperazinyl]propyl]-5,6-methylenedioxy-1-(3,4-dimethoxybenzyl)-1H-indazole or a salt thereof;

5,6-dimethoxy-2-[[4,5-dimethoxy-2-[4-(2-methoxyphenyl)-1-piperazinyl]propyl]phenyl]-1-methylindole or a salt thereof;

5,6-dimethoxy-2-[[4,5-methylenedioxy-2-[4-(2-methoxyphenyl)-1-piperazinyl]propyl]phenyl]-1-methylindole or a salt thereof;

1-(3-chloro-2-methylphenyl)-4-[2-[[4,5-dimethoxy-2-(3,4-dimethoxyphenyl)]phenyl]propyl]piperazine or a salt thereof; and 1-(3-chloro-2-methylphenyl)-4-[2-[[4,5-methylenedioxy-2-(3,4-dimethoxyphenyl)]phenyl]propyl]-piperazine or a salt thereof.

The compounds of formula (I) according to the present invention can be prepared, for example, by the following processes A to E:

[Process A]

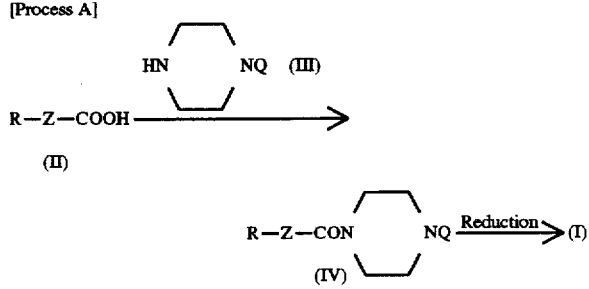

[Process B]

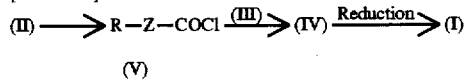

[Process C]

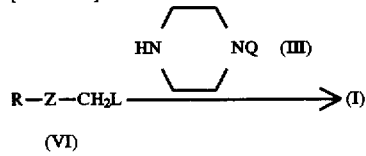

[Process D]

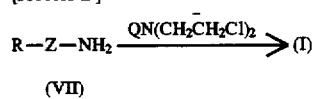

[Process E]

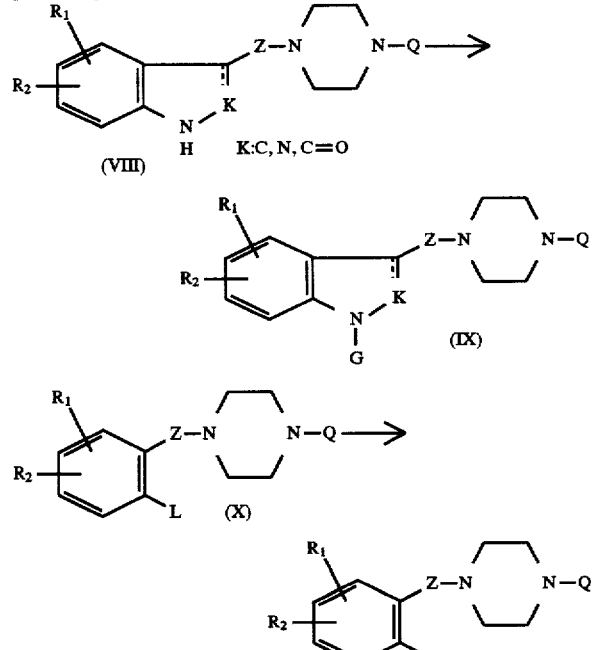

Processes A to E will be explained below in detail.

[Process A]

Carboxylic acid derivative (II), which is prepared according to a known process as hereinafter described, and piperazine derivative (III) are condensed to yield amide compound (IV). The condensation reaction is carried out in the presence of a condensing agent, such as dicyclohexylcarbodiimide, carbodiimidazole, pyridyl disulfide-triphenylphosphine, etc. Amide compound (IV) is then reduced to yield compound (I). The reduction reaction is usually carried out by using a metal hydride compound, such as lithium aluminum hydride, sodium bis(2-methoxyethoxy) aluminum hydride, sodium borohydride-lithium bromide, borane or a borane-tetrahydrofuran complex, in an inert solvent, such as an ether (e.g., diethyl ether, tetrahydrofuran, dioxane or 1,2-dimethoxyethane) or an aromatic hydrocarbon (e.g., benzene), at room temperature or, if necessary, at a temperature of from −20° C. up to the boiling point of the solvent used.

[Process B]

Carboxylic acid (II) is converted to acid chloride (V), and acid chloride (V) is reacted with piperazine derivative (III) to yield amide compound (IV), which is then reduced to compound (I).

The reaction for obtaining acid chloride (V) is effected by using thionyl chloride or oxalyl chloride with or without an inert solvent, such as a halogenoalkane (e.g., dichloromethane or dichloroethane) or an aromatic hydro-carbon, at a temperature of from −20° C. up to the boiling point of the solvent used.

The reaction between acid chloride (V) and piperazine derivative (III) is conducted in an inert solvent, such as a halogenoalkane (e.g., dichloromethane or dichloroethane), an ether (e.g., diethyl ether, tetrahydrofuran, dioxane or 1,2-dimethoxyethane), an amide (e.g., acetamide, dimethylform-amide or N-methyl-2-pyrrolidone), acetonitrile or an aromatic hydrocarbon, at a temperature of from −20° C. up to the refluxing temperature of the solvent used. Reduction of amide compound (IV) is performed in the same manner as in Process A.

[Process C]

Compound (VI) [wherein L represents a leaving group selected from a halogen atom and a substituted sulfonyl group, such as an alkylsulfonyl group (e.g., a mesyloxy group) or an arylsulfonyl group (e.g., a tosyloxy group), the alkyl moiety or aryl moiety of which may be substituted with a halogen atom, an alkyl group, etc.], which is synthesized according to a known process as hereinafter described, is reacted with piperazine derivative (III).

The reaction is preferably carried out in the presence of an organic or inorganic base. Suitable inorganic bases include a carbonate, hydrogencarbonate, etc. of an alkali metal, such as potassium carbonate, sodium carbonate, lithium carbonate, potassium hydrogencarbonate, sodium hydrogencarbonate or lithium hydrogencarbonate. Suitable organic bases include tertiary amines, such as trialkylamines (e.g., triethylamine, tributylamine, and diethylisopropyl-amine); aromatic amines, such as dialkylanilines (e.g., N,N-dimethylaniline and N,N-diethylaniline); and heterocyclic compounds, such as saturated or aromatic heterocyclic compounds (e.g., an N-alkylpiperazine, an N-alkylmorpholine, pyridine, and 4-dimethylaminopyridine).

Instead of using a base, the reaction may be carried out by using piperazine derivative (III) in excess, i.e., 2 or more molar equivalents to compound (VI).

The reaction between compound (VI) and piperazine derivative (III) is usually conducted in an inert solvent, such as a halogenoalkane (e.g., dichloromethane or dichloroethane), an amide (e.g., acetamide, dimethylformamide or N-methyl-2-pyrrolidone), a dialkylketone (e.g., acetone or methyl ethyl ketone), acetonitrile or an aromatic hydro-carbon, at a temperature of from -20° C. up to the boiling point of the solvent used.

[Process D]

Amino derivative (VII), which is obtained by a known process as hereinafter described, is reacted with a bis(2-chloroethyl)amino derivative.

The reaction is performed in a basic condition, for example in the presence of an organic or inorganic base as described in process C or by using compound (VII) in excess.

The reaction is effected in an inert solvent, preferably in the presence of NaI, etc. at a temperature of from -20° C. up to the boiling point of the solvent used. Suitable solvents include halogenoalkanes, e.g., dichloro-methane and dichloroethane; amides, e.g., acetamide, dimethylformamide and N-methyl-2-pyrrolidone; dialkylketones, e.g., acetone and methyl ethyl ketone; acetonitrile; aromatic hydrocarbons; and halogenobenzene, e.g., chlorobenzene.

[Process E]

The compound of formula (I) can also be synthesized by once preparing compound (VIII) or (X) and afterward introducing a desired substituent as represented by G.

Compound (VIII) is reacted with G-L [wherein L represents a leaving group selected from a halogen atom or a substituted sulfonyl group, such as an alkylsulfonyl group (e.g. a mesyloxy group) or an arylsulfonyl group (e.g., a tosyloxy group), the alkyl or aryl moiety of which may be substituted with a halogen atom, an alkyl group, etc.] in the presence of an appropriate base, such as sodium hydride, sodium methoxide, potassium carbonate, sodium hydroxide, lithium methoxide, butyl lithium or potassium hydride, to provide compound (IX).

The reaction may be conducted in the presence of an inert solvent, such as an amide (e.g., acetamide, dimethylformamide or N-methyl-2-pyrrolidone), a dialkyl ketone (e.g., acetone or methyl ethyl ketone), an ether (e.g., diethyl ether, tetrahydrofuran, dioxane or 1,2-dimethoxyethane), acetonitrile or dimethyl sulfoxide. The reaction temperature is from -20° C. up to the refluxing temperature of the solvent used.

Where G is a residue of a substituted benzene derivative, compound (IX) can be obtained by applying the method of M. A. Khan, et al. described in *Chemical & Pharmaceutical Bulletin*, Vol. 25, No. 11, pp. 3110–3114 (1977). That is, compound (VIII) is reacted with a halogenated benzene derivative, such as a bromobenzene or iodobenzene derivative, in the presence of an appropriate copper compound, such as a copper salt (e.g., copper bromide or copper chloride) or copper oxide. The reaction is carried out in the presence or absence of potassium carbonate, with or without a solvent, such as an amide (e.g., acetamide, dimethylformamide or N-methyl-2-pyrrolidone), dimethyl sulfoxide, hexamethylphosphoramide, pyridine or quinoline, at a temperature of from room temperature up to the boiling point of the solvent used.

When starting with compound (X) in which the releasable group L is a halogen atom (e.g., bromine or iodine), a substituted phenyl group and substituted phenol group can be introduced as G by Ullmann type reaction using copper powder or an appropriate copper compound, such as a copper salt.

Introduction of an acetylene side chain can be achieved by using copper acetylide synthesized by the process of J. R. Carson et al. described in *J. Med. Chem.*, Vol. 31, pp. 630–636 (1988). The reaction is carried out with or without a solvent, such as pyridine, quinoline, dimethyl-formamide, dimethyl sulfoxide or hexamethylphosphoramide, at a temperature of from room temperature up to the refluxing temperature of the solvent used.

Wherethe leaving group L is a halogen atom (e.g., bromine, iodine or chlorine), the halogenated benzene derivative is reacted with a metallic lithium derivative, such as butyl lithium or LDA, in an appropriate solvent, such as tetrahydrofuran or diethyl ether, at a temperature of from -100° C. up to the refluxing temperature of the solvent used, reacting the product with an aldehyde derivative G-CHO, and further treating the product by a combination of general syntheses.

Where L in compound (X) is a proton, introduction of an acyl type substituent can be carried out in an appropriate solvent, such as dichloromethane, dichloroethane or nitrobenzene, in the presence of a Lewis acid, such as aluminum chloride, zinc chloride, stannic chloride or boron trifluoride, or a protonic acid, such as sulfuric acid or polyphosphoric acid, at a temperature of from -20° C. up to the refluxing temperature of the solvent used.

While compounds (VIII) to (XI) shown above with respect to process E have two substituents ($R^1$ and $R^2$) on the indazole or phenyl nucleus for the sake of illustration, this is not meant to limit the number of substituents to two.

The partial structure R in the compounds of formula (I) can be prepared by various processes. Typical processes will be described below.

[Process 1]

Compounds (I) having an indazole skeleton in R can be synthesized as follows. A 1-substituted indazole-3-carboxylic acid is synthesized in accordance with the process of G. Corsi, et al. described in *Journal of Medicinal Chemistry*, Vol. 19, pp. 778–783 (1976). This compound, either as produced or after adding one or two carbon atoms to the carboxylic acid moiety by known chemical means, can be led to compound (I) by any of processes A to E or a combination thereof.

3-Chloromethyl-1H-indazole obtained by the process described in *Synthetic Communication*, Vol. 18, pp. 259–264 (1988) can also be led to compound (I) by any of processes A to E or a combination thereof.

A piperazine derivative having an indazole skeleton can also be obtained by the process described in JP-B-41-9779 (the term "JP-B" as used herein means an "examined published Japanese patent application"). Further, a desired substituent G may be introduced thereinto according to process E.

[Process 2]

Compounds having an indole skeleton in R can be synthesized by applying the process of M. E. Speeter, et al. described in *Journal of American Chemical Society*, Vol. 76, pp 6208–6210 (1954) to an indole derivative synthesized by a known process, reacting the resulting indole derivative with oxalyl chloride and piperazine derivative (III) in a solvent, such as diethyl ether or tetrahydrofuran, at a temperature of from -100° C. up to the refluxing temperature of the solvent used to synthesize a diketone compound, and reducing the diketone compound by using lithium aluminum hydride, etc. in a solvent, such as diethyl ether or tetrahydrofuran, at a temperature of from -20° C. up to the refluxing temperature of the solvent used.

The resulting indole derivative may further be subjected to process E to yield compound (I).

[Process 3]

Compounds having an indolone skeleton in R can be synthesized by applying the process described in JP-A-2-

73062 (the term "JP-A" as used herein means an "unexamined published Japanese patent application"). Compounds having an alkoxyl group at the 5- and 6-positions of an indolone skeleton can be obtained by, for example, reacting 3,4-dimethoxyphenylacetonitrile with ethylene oxide in the presence of sodium amide to synthesize 1-hydroxy-3-(3,4-dimethoxy)butyronitrile, subjecting the 1-hydroxy-3-(3,4-dimethoxy)butyronitrile to acid hydrolysis and lactonization, introducing a nitro group into the lactone, followed by catalytic hydrogenation (in the presence of platinum oxide, etc.) and cyclization to synthesize 5,6-dimethoxy-3-hydroxy-2-oxoindole, and leading the 5,6-dimethoxy-3-hydroxy-2-oxoindole to compound (I) by any of processes A to E or a combination thereof.

[Process 4]

Compounds having a bisaryl skeleton in R can be synthesized by applying the process described in *Tetrahedron Letters*, Vol. 13, pp. 1665–1668 (1990), that is, cross-coupling of an aryl group having an alkylboronic acid radical using a palladium catalyst.

Further, an orthomethoxyphenyloxazoline derivative, described in *Journal of Organic Chemistry*, Vol. 43, pp. 1372–1379 (1978), is reacted with an aryl Grignard reagent to synthesize a bisaryl derivative, which is further treated by a combination of known chemical means.

[Process 5]

Of compounds having the partial structure R shown in compound (X), those having a deoxybenzoin type substituent as Z can be synthesized by introducing a deoxybenzoin type substituent into an ethyl phenylacetate derivative in the presence of a Lewis acid, such as aluminum chloride, with or without a solvent, such as dichloromethane or dichloroethane, according to a Friedel-Crafts reaction and, if necessary protecting the carboxyl group, leading the resulting compound to compound (I) by a combination of known chemical means and any of processes A to E.

In the preparation of the compound of formula (I), where a starting compound contains a carboxyl group, an amino group, an N—H group, a hydroxyl group, a thiol group or a like functional substituent, it is recommended in some cases that such a functional group is once protected with an appropriate protective group and, after completion of the necessary reaction(s), the protective group is removed. These functional groups do not need to be protected unless they are inactive to the reaction.

The piperazine derivatives of formula (I) thus synthesized and their salts and/or hydrates have excellent calmodulin inhibitory activity. The piperazine derivatives (I) manifest their effect when given either orally or non-orally so that they can be administered through oral or non-oral routes.

The dose of the compound is decided appropriately in accordance with the symptoms, age, and body weight of a patient. An oral dose generally ranges from 1 to 1000 mg, preferably from 10 to 500 mg, per day for an adult in a single or several divided doses. Oral dose forms include tablets, capsules, powders, and granules. These dose forms are prepared using general additives, such as vehicles, lubricants and binders, in a known manner. For non-oral administration, the compound is given by subcutaneous injection, intravenous injection or intravenous infusion at a dose generally ranging from 1 to 2000 mg, preferably from 10 to 500 mg, per day for an adult.

When combined with other drugs, the piperazine derivative of formula (I) is expected to produce an additive effect or a synergistic effect in prevention and treatment of various diseases. Suitable drugs with which the compound of the present invention can be combined include drugs for cerebral circulation improvement (e.g., Cinepazide maleate), drugs for cerebral metabolism improvement (e.g., Idebenone, Indeloxazine), psychotropic drugs (e.g., Timiperone, Imipramine, and Diazepam), intracranial antihypertensive agents (e.g., Glyceol), antihypertensive agents, vasodilators (e.g., Trapidil), antipyretic, analgesic, antiinflammatory agents, antiinflammatory steroids, anti-blood platelet drugs (e.g., Ticlopidine), anticoagulants (e.g., Heparin), drugs for inducing fibrinolysis (e.g., tissue plasminogen activator), diuretics, antihyperlipemic agents (e.g., Probucol), treating agents for digestive ulcers, blood substitutes, drugs for hepatic diseases, and anti-malignancy agents.

The compounds of the present invention and the pharmacologically acceptable salts thereof exhibit excellent calmodulin inhibitory activity and excellent antihypoxia activity as well. Additionally, the compounds showed excellent efficacy on various disease models at dose levels causing no significant central inhibitory action through oral or non-oral administration (for example, inhibitory action on delayed neuronal death of the hippocampus in merions and anti-edema action).

Accordingly, the compounds of the present invention and their pharmacologically acceptable salts are of high utility as drugs for inhibiting intracellular calcium physiological activities in which calmodulin takes part in. That is, they are useful as a preventing and treating agent for various diseases induced by excessive activation of calmodulin, especially hypertension, ischemic diseases in the brain, the heart, the kidney, etc. (e.g., cerebral infarction, cerebral embolism, transient cerebral ischemic attack, cerebral thrombosis, cardiac infarction, angina pectoris, cardiac insufficiency, acute renal insufficiency, and nephritis), diseases in the brain region (e.g., Alzheimer's disease, Parkinson's disease, and dementia of Binswanger), chemical poisoning, gas poisoning, traumatic cerebral diseases and symptoms based on these diseases (e.g., reduction of spontaneity, depression, and dysmnesia).

The present invention will now be illustrated in greater detail with reference to Reference Examples, Examples, and Test Examples, but the present invention should not be construed as being limited thereto. In Examples, all the mixing ratios in mixed solvents, such as a developing solvent for chromatography, are by volume unless otherwise indicated.

TEST EXAMPLE 1

Calmodulin (CaM) inhibitory activity

The calmodulin inhibitory activity of a compound was evaluated by using its effect of inhibiting calmodulin-depending cyclic nucleotide phosphodiesterase (PDE) as an index. The assay for PDE inhibitory activity was carried out by the following procedure described by Thompson (*Advances in Cyclic Nucleotide Research*, 10, 69, 1979) with a modification. The first-stage incubation was carried out at 30° C. for 10 minutes with the following reaction mixture: 50 mM Tris-HCl buffer (pH 7.5), 5 mM $MgCl_2$, 1 mg/ml bovine serum albumin, CaM from bovine brain, [$^3$H]-cGMP, 1 mM $CaCl_2$ or 1 mM EGTA, PDE from bovine brain, and a test compound in a total volume of 0.5 ml. After the incubation, the mixture was heated on a boiling water bath for 1 minute. Then, 50 µl of snake venom (1 mg/ml) was added to the reaction mixture and the whole mixture was incubated at 30° C. for 10 minutes. After the incubation, 0.5 ml of AG1-X2 resin (1:1 slurry in water) was added to the mixture and centrifuged at 3000Xrpm for 20 min. The radioactivity of the supernatant solution was measured by a liquid scintillation counter. The $IC_{50}$ value was determined as the concentration showing 50% inhibition of PDE activity potentiated by CaM. The results obtained are shown in Table 1 below.

TABLE 1

Inhibitory Activity on Ca/Calmodulin-Dependent PDE Activity

| Test Compound | $IC_{50}$ |
|---|---|
| Compound of Example 17 | 3.1 |
| Compound of Example 23 | 5.5 |
| Compound of Example 81 | 9.4 |
| Comparative Compound (W-7) | 33.5 |

TEST EXAMPLE 2

Activity on Nitrogen-induced Hypoxia Model in Mouse

Nine to ten mice per group were each orally given 30 mg of a test compound. After 60 minutes from the administration, each mouse was put in a 500 ml-volume transparent container having a vent hole; and nitrogen gas was introduced into the container at a rate of 5000 ml/min. The time from the start of nitrogen introduction to respiratory standstill was measured, and a rate of increase of the time over that of a control group (100%) was obtained. The results obtained are shown in Table 2 below.

TABLE 2

Activity on Nitrogen-induced Hypoxia Model in Mouse

| Test Compound | Rate of Increase of Survival Time (%, 30 mg/kg, p.o.) |
|---|---|
| Compound of Example 17 | 19.2 |
| Compound of Example 23 | 15.1 |

EXAMPLE 1

5,6-Dimethoxy-1-(3,4-dimethoxyphenyl)-3-[2-[4-(2-methoxyphenyl)-1-piperazinyl]ethyl]indole A solution of 1.0 g of 5,6-dimethoxyindole in 120 ml of anhydrous ethyl ether was added dropwise to 0.49 ml of oxalyl chloride at 0° C., followed by stirring for 20 minutes. To the mixture was added 1.08 g of 2-methoxyphenylpiperazine, and the mixture was further Stirred at that temperature for 30 minutes. After completion of the reaction, water was added thereto, and the mixture was extracted with ethyl acetate. The extract was dried over anhydrous sodium sulfate, and the solvent was evaporated to yield 1.5 g of a crude amide compound crystal.

The crystal was dried and then added to a suspension of 260 mg of lithium aluminum hydride in 50 ml of tetrahydrofuran while heating under reflux. After completion of the reaction, 0.26 ml of water, 0.26 ml of a 10% sodium hydroxide aqueous solution, and 0.78 ml of water were successively added to the reaction mixture. The insoluble material was removed by filtration using Celite and dried over anhydrous sodium sulfate. The solvent was evaporated, and the residue was purified by silica gel column chromatography. From the fraction eluted with ethyl acetate was recovered 820 mg of a piperazine derivative.

The resulting piperazine derivative (820 mg) was added to a suspension of 124 mg of 60% sodium hydride in dimethylformamide. After stirring at room temperature for 30 minutes, 960 mg of 3,4-dimethoxybenzyl chloride was added thereto, followed by stirring at room temperature for 1 hour. After the reaction, water was added to the reaction mixture, followed by extraction with ethyl acetate. The extract was washed successively with water and a saturated sodium chloride aqueous solution, dried over anhydrous sodium sulfate, and the solvent was evaporated. The residue was purified by silica gel column chromatography. From the fraction eluted with ethyl acetate was obtained 600 mg of the title compound as a yellow oily substance.

IR (KBr) $v_{max}$ ($cm^{-1}$): 1503, 1464, 1242, 1137, 1026

$^1$H-NMR (CDCl$_3$) δ ppm:

2.7–3.0 (6H, m), 3.9–3.3 (4H, m), 3.78 (3H, s), 3.84 (3H, s), 3.86 (3H, s), 3.93 (3H, s), 3.7–4.0 (2H, m), 5.14 (2H, s), 6.6–7.1 (10H, m)

REFERENCE EXAMPLE 1

4,5-Dimethoxy-2-amino-α-chloroacetophenone

In 40 ml of 1,1,2,2-tetrachloroethane was dissolved 4.0 g of 3,4-dimethoxyaniline, and to the solution was added 28 mmol of boron trichloride in an argon atmosphere while cooling with ice. To the reaction mixture was further added 2.3 g of chloroacetonitrile, followed by heating under reflux for 1.5 hours.

After cooling, 20 ml of 2N hydrochloric acid was added to the reaction mixture.. After stirring at 80° C. for 30 minutes, the supernatant liquor was removed by decantation. The residue was extracted with dichloromethane. The residue was collected, neutralized with a sodium hydroxide aqueous solution, filtered using Celite, and again extracted with dichloromethane. The organic layer was dried over anhydrous sodium sulfate and the solvent was evaporated. The residue was purified by silica gel column chromatography (hexane:ethyl acetate=3:1) to yield 809 mg of the title compound.

$^1$H-NMR (CDCl$_3$) δ ppm:

3.82 (3H, s), 3.87 (3H, s), 4.70 (2H, S), 6.12 (1H, s), 7.03 (1H, s)

EXAMPLE 2

5,6-Dimethoxy-3-[[4-(2-methoxyphenyl)-1-piperazinyl]methyl]-1H-indazole

In 20 ml of concentrated hydrochloric acid was dissolved 800 mg of 4,5-dimethoxy-2-amino-α-chloroacetophenone, and a solution of 264 mg (3.8 mmol) of sodium nitrite in 4.0 ml of water was added thereto at −10° C., followed by stirring for 1 hour. Three equivalents of stannous chloride and 110 ml of concentrated hydrochloric acid were further added thereto, followed by stirring for 1 hour. The precipitate thus formed was collected by filtration, washed once with water, and air-dried. The solid was dissolved in dimethyl sulfoxide, and 700 mg of N-(2-methoxyphenyl) piperazine and 3.0 g of potassium carbonate were added to the solution. Thirty minutes later, ethyl acetate was added, and the solution was washed three times with water and once with a saturated sodium chloride aqueous solution. The organic layer was dried, and the solvent was evaporated. Purification of the residue by silica gel column chromatography (ethyl acetate:ethanol=6:1) gave 594 mg of the title compound.

Melting point: 192° C.

IR (KBr) $v_{max}$ (cm$^{-1}$): 3376, 1503, 1488, 1317, 1242, 1209

$^1$H-NMR (CDCl$_3$) δ ppm:
2.6–2.8 (4H, m), 2.9–3.2 (5H, m), 3.84 (3H, m), 3.93 (6H, br. s), 6.8–7.0 (5H, m), 7.26 (1H, s)

EXAMPLE 3

5,6-Dimethoxy-1-(3,4-dimethoxyphenyl)methyl-3-[[4-(2-methoxyphenyl)-1-piperazinyl]methyl]-1H-indazole In dimethylformamide was suspended 61.6 mg of sodium hydride at 0° C., and 590 mg of 5,6-dimethoxy-3-[[4-(2-methoxyphenyl)-1-piperazinyl]methyl]indazole was added thereto, followed by stirring for 30 minutes. To the mixture was added 290 mg of 3,4-dimethoxyphenylmethyl chloride. After 1.5 hours, 2.0 ml of water was added to the reaction mixture, followed by evaporation of the solvent. The residue was purified by silica gel column chromatography (chloroform:ethanol=20:1) and recrystallized from ethanol to yield 654 mg of the title compound.

Melting point: 149°–150° C.

IR (cm$^{-1}$): 1506, 1473, 1257, 1158, 1140, 1029 $^1$H-NMR (CDCl$_3$) δ ppm:
7.26 (s, 1H), 7.0–6.5 (m, 8H), 5.45 (s, 2H), 3.95 (s, 2H), 3.92 (s, 3H), 3.86 (s, 3H), 3.84 (s, 6H), 3.76 (s, 3H), 3.2–3.0 (m, 4H), 2.8–2.6 (m, 4H)

REFERENCE EXAMPLE 2

N-(3,4-Dimethoxyphenethyl)-2-(4,5-dimethoxyphenyl)acetamide

A dry dichloromethane solution (1000 ml) of 3,4-dimethoxyphenylacetyl chloride prepared from 325 g of 3,4-dimethoxyphenylacetic acid and 300 ml of thionyl chloride was slowly added to a two-phase solvent consisting of 300 g of 3,4-dimethoxyphenethylamine, 850 ml of 2N sodium hydroxide, and 2000 ml of dichloromethane while stirring under ice-cooling. Chloroform was added to the mixture to dissolve the precipitated solid. The aqueous layer was removed, and the organic layer was washed with a saturated sodium hydrogencarbonate aqueous solution, dried, and the solvent was evaporated. To the residue was added methanol, the mixture was heated and allowed to cool, and the thus precipitated crystal was collected by filtration to yield 570 g of the title compound.

REFERENCE EXAMPLE 3

1-(3,4-Dimethoxybenzyl)-3,4-dihydro-6,7-dimethoxyisoquinoline Hydrochloride

A solution of 570 g of N-(3,4-dimethoxyphenethyl)-2-(4,5-dimethoxyphenyl)acetamide and 500 ml of phosphorus oxychloride in 3500 ml of acetonitrile was heated under reflux for 0.5 hour. The solvent was evaporated, and ethanol was added to the residue, followed by allowing to stand. The thus precipitated crystal was collected by filtration to yield 590 g of the titled compound.

$^1$H-NMR (d$_6$-DMSO) δ:
7.63 (s, 1H), 7.26 (s, 1H), 7.11 (s, 1H), 7.0–6.8 (m, 2H), 4.58 (s, 2H), 3.88 (s, 3H), 3.83 (s, 3H),. 3.74 (s, 3H), 3.70 (s, 3H), 4.0–3.8 (m, 2H), 3.1–2.9 (broad t, J=7 Hz, 2H)

REFERENCE EXAMPLE 4

Trans-2-acetyl-6,7-dimethoxy-1-(4,5-dimethoxybenzylidene)-1,2,3,4-tetrahydroisoquinoline To 600 g of 1-(4,5-dimethoxybenzyl)-3,4-dihydro-6,7-dimethoxyisoquinoline hydrochloride was added 2000 ml of acetic anhydride, and the mixture was refluxed for 6 hours, followed by allowing to cool overnight. The thus precipitated crystal was collected by filtration and recrystallized from ethanol to give 500 g of the title compound.

IR (cm$^{-1}$): 1632, 1518, 1263, 1245

$^1$H-NMR (CDCl$_3$) δ ppm:
7.13 (s, 1H), 7.05 (s, 1H), 6.90 (s, 1H), 6.71 (s, 1H), 6.62 (s, 1H), 5.05 (d, J=9 Hz, 1H), 3.97 (s, 3H), 3.89 (s, 9H), 3.8–2.5 (m, 4H), 1.81 (s, 3H)

REFERENCE EXAMPLE 5

2-(2-Acetamidoethyl)-4,4', 5,5'-tetramethoxydeoxybenzoin

To 500 g of trans-2-acetyl-6,7-dimethoxy-1-(4,5-dimethoxybenzylidene)-1,2,3,4-tetrahydroisoquinoline were added 1000 ml of 10% hydrochloric acid and 500 ml of methanol, and the mixture was refluxed. The reaction mixture was poured into a sodium carbonate aqueous solution and extracted with methylene chloride. The solvent was removed from the extract under reduced pressure. Recrystallization of the residue from ethanol gave 270 g of the title compound.

IR (cm$^{-1}$): 1680, 1638, 1515, 1128

$^1$H-NMR (CDCl$_3$) δ ppm:
7.26 (s, 1H), 6.9–6.75 (m, 4H), 6.7–6.5 (br, 1H), 4.15 (s, 2H), 3.91 (s, 3H), 3.89 (s, 3H), 3.86 (s, 3H), 3.85 (s, 3H), 3.6–3.4 (m, 2H), 2.92 (t, J=7.2 Hz, 2H), 1.89 (s, 3H)

REFERENCE EXAMPLE 6

2-(2-Acetamidoethyl)-2'-nitro-4,4', 5,5'-tetramethoxydeoxybenzoin

To a solution of 200 g of 2-(2-acetamidoethyl)-4,4', 5,5'-tetramethoxydeoxybenzoin in 2000 ml of acetic acid was slowly added 60 ml of 70% nitric acid at 0° C. Immediately after the addition, the mixture was poured into water and extracted with methylene chloride. The extract was neutralized with a sodium hydrogencarbonate aqueous solution and washed with a saturated sodium chloride aqueous solution. The solvent was removed under reduced pressure, and the residue was recrystallized from ethanol to yield 196 g of the title compound.

Melting point: 142°–144° C.

IR (cm$^{-1}$): 1524, 1272, 1128

$^1$H-NMR (CDCl$_3$) δ ppm:
7.79 (s, 1H), 7.36 (s, 1H), 6.80 (s, 1H), 6.76 (s, 1H), 6.4 (br, 1H), 4.60 (s, 2H), 4.0 (br, 12H), 3.45 (q, J=7.2 Hz, 2H), 2.94 (t, J=7.2 Hz, 2H), 1.85 (s, 3H)

REFERENCE EXAMPLE 7

2-[2-(2-Acetamidoethyl)-4,5-dimethoxyphenyl]-5,6-dimethoxyindole

To a 80% acetic acid solution of 4.60 g of 2-(2-acetamidoethyl)-2'-nitro-4,4', 5,5'-tetramethoxydeoxybenzoin was slowly added 4.7 g of zinc at 85° C. The reaction mixture was filtered, washed with ethanol, and the solvent was evaporated. To the residue was added an ammonium hydroxide aqueous solution, and the mixture was extracted with ethyl acetate. The solvent was evaporated, and the residue was purified by silica gel column chromatography (ethyl acetate) to yield 1.84 g of the title compound.

$^1$H-NMR (CDCl$_3$) δ ppm:

8.10 (s, 2H), 8.08 (s, 1H), 8.06 (s, 1H), 7.72 (s, 1H), 7.44 (s, 1H), 6.80 (br, 1H), 3.92 (s, 6H), 3.88 (s, 6H), 3.5–3.3 (m, 2H), 3.0–2.8 (m, 2H), 1.92 (s, 3H)

REFERENCE EXAMPLE 8

2-[2-(2-Acetamidoethyl)-4,5-dimethoxyphenyl]-5,6-dimethoxy-1-methylindole

In dimethyl sulfoxide was slowly suspended 480 mg of 35% potassium hydride, and 1.37 g of 2-[2-(2-acetamidoethyl)-4,5-dimethoxyphenyl]-5,6-dimethoxyindole was added to the suspension, followed by stirring for 10 minutes. To the mixture was further added 700 mg of dimethylsulfate, followed by stirring for 30 minutes. The reaction mixture was poured into water and extracted with methylene chloride. The extract was washed successively with water and a saturated sodium chloride aqueous solution, and the solvent was removed under reduced pressure. Recrystallization of the residue from ethanol yielded 1.20 g of the title compound.

IR (cm$^{-1}$): 3376, 1168, 1486, 1222

$^1$H-NMR (CDCl$_3$) δ ppm:

7.11 (s, 1H), 6.87 (s, 2H), 6.81 (s, 1H), 6.34 (s, 1H), 5.4 (br, 1H), 3.97 (s, 3H), 3.93 (s, 6H), 3.84 (s, 3H), 3.48 (s, 3H), 3.4–3.0 (m, 2H), 2.65 (t, J=7.2 Hz, 2H), 1.84 (s, 3H)

REFERENCE EXAMPLE 9

2-[2-(2-Aminoethyl)-4,5-dimethoxyphenyl]-5,6-dimethoxy-1-methylindole Hydrochloride A 2N hydrochloric acid solution of 53.0 g of 2-[2-(2-acetamidoethyl)-4,5-dimethoxyphenyl]-5,6-dimethoxy-1-methylindole was heated under reflux for 17 hours. The reaction mixture was azeotropically distilled under reduced pressure with ethanol and benzene, and the residue was recrystallized from ethanol to yield 48 g of the title compound.

IR (cm$^{-1}$): 3272, 2832, 1504, 1454, 1244, 1010

$^1$H-NMR (CDCl$_3$) δ ppm:

6.98 (br, 3H), 7.06 (s, 1H), 7.00 (s, 1H), 6.9–6.7 (m, 2H), 6.35 (s, 1H), 3.94 (s, 3H), 3.90 (s, 3H), 3.87 (s, 3H), 3.80 (s, 3H), 3.45 (s, 3H), 3.0–2.7 (br, 4H)

EXAMPLE 4

5,6-Dimethoxy-2-[[4,5-dimethoxy-2-[4-(2-methoxyphenyl)-1-piperazinyl]ethyl]phenyl]-1-methylindole A solution of 47 g of 2-[2-(2-aminoethyl)-4,5-dimethoxyphenyl]-5,6-dimethoxy-1-methylindole hydrochloride, 30.7 g of o-bis(2-chloroethyl)aminoanisole, 37.2 g of sodium iodide, and 34.0 g of potassium carbonate in 200 ml of dimethylformamide was heated at 80° C. for 1 hour. To the solution was added 17 g of potassium carbonate and, 3 hours later, 17 g of potassium carbonate was further added, followed by heating for 15 hours. The solvent was removed under reduced pressure, and the residue was dissolved in water and extracted with methylene chloride. The extract was purified by silica gel column chromatography (ethyl acetate) and recrystallized from ethanol to give 32 g (51%) of the title compound.

Melting point: 171°–173° C.

IR (cm$^{-1}$): 1500, 1486, 1236, 1212

$^1$H-NMR (CDCl$_3$) δ ppm:

7.10 (s, 1H), 7.0–6.8 (m, 7H), 3.98 (s, 3H), 3.94 (s, 3H), 3.84 (s, 3H), 3.82 (s, 3H), 2.94 (s, 3H), 3.1–2.9 (m, 4H), 2.8–2.4 (m, 8H)

REFERENCE EXAMPLE 10

4,5-Dimethoxy-2-(1-pyrrolyl)benzenemethanol

In 100 ml of tetrahydrofuran was dissolved 14.5 g of methyl 4,5-dimethoxy-2-(1-ipyrrolyl)benzenecarboxylate, and 24.5 ml (3.4 M) of sodium bis(2-methoxyethoxy) aluminum hydride was added thereto dropwise with stirring while cooling with ice. After the addition, the mixture was warmed to room temperature and heated for 6 hours. After completion of the reaction, 0.63 ml of a saturated sodium hydrogen-carbonate aqueous solution and 1.55 ml of water were added to the reaction mixture in this order, and the precipitate was removed by filtration. The filtrate was evaporated, and the residue was subjected to column chromatography on silica gel. From the fraction eluted with chloroform was recovered, 10.3 g of a brown oily substance. Recrystallization from ethyl ether gave the title compound as a colorless crystal.

Melting point: 92°–93° C.

IR (KBr, cm$^{-1}$): 3530, 2960, 2930, 1610, 1520

$^1$H-NMR (CDCl$_3$) δ ppm:

3.86 (3H, s), 3.95 (3H, s), 4.45 (2H, d, J=5.3 Hz), 6.30 (2H, t, J=2.1 Hz), 6.84 (2H, t, J=2.1 Hz), 7.04 (1H, s)

REFERENCE EXAMPLE 11

Diethyl (2-(4,5-Dimethoxy-2-(1-pyrrolyl)phenyl) ethyl)malonate

In 15 ml of ethyl ether was dissolved 3.0 g of 4,5-dimethoxy-2-(1-pyrrolyl)benzenemethanol, and 15 ml of concentrated hydrochloric acid was added thereto, followed by stirring at room temperature for 1 hour. To the reaction mixture was added 50 ml of water, and the mixture was neutralized with a saturated sodium carbonate aqueous solution and extracted with chloroform. The extract was dried over anhydrous sodium sulfate, and the solvent was removed under reduced pressure to yield a brown oily substance. Separately, 460 mg of metallic sodium was dissolved in 25 ml of ethanol, and 6.18 g of ethyl malonate was added thereto to prepare a solution. To this solution was added a tetrahydrofuran solution (25 ml) of the above-prepared brown oily substance. After stirring at room temperature for 3 hours, the solvent was removed under reduced pressure. Water was added to the residue, and the mixture was made acidic with concentrated hydrochloric acid and then extracted with chloroform. The organic layer was dried over anhydrous sodium sulfate, and the solvent was removed under reduced pressure. Purification of the residue by silica gel column chromatography (chloroform) gave 3.10 g of the title compound as a brown oily substance.

$^1$H-NMR (CDCl$_3$) δ ppm:

1.16 (6H, t, J=7.0 Hz), 3.00–3.25 (2H, m), 3.70–3.90 (1H, m), 3.83, 3.88 (3H, s), 4.08 (4H, q, J=7.0 Hz), 6.30 (2H, t, J=2.0 Hz), 6.77 (2H, .s)

REFERENCE EXAMPLE 12

Ethyl 3-(4,5-Dimethoxy-2-(1-pyrrolyl)phenyl) propionate

In 50 ml of ethanol was dissolved 3.1 g of diethyl (2-(4,5-dimethoxy-2-(1-pyrrolyl)phenyl)ethyl)malonate, and 5.0 ml of 35% sodium hydroxide was added to the solution, followed by heating under reflux for 3 hours. The solvent was removed under reduced pressure, and water was added to the residue. The residue was made acidic with concentrated hydrochloric acid and extracted with chloroform. The extract was dried over anhydrous sodium sulfate, and the solvent was removed under reduced pressure to yield pale brown powder. The powder was heated at 150° C. for 10 minutes, allowed to cool, and purified by silica gel column chromatography (chloroform-methanol) to obtain 2.1 g of pale brown powder. Recrystallization from chloroform-ethyl ether gave the title compound as a colorless crystal.

Melting point: 170°–173° C.

$^1$H-NMR (CDCl$_3$) δ ppm:

2.83 (2H, t, J=7.8 Hz), 2.77 (2H, t, J=7.8 Hz), 3.84, 3.90 (3H, s), 6.30, 6.74 (2H, t, J=2.0 Hz), 6.78 (2H, s)

EXAMPLE 5

1-(3-(4,5-Dimethoxy-2-(1-pyrrolyl)phenyl)-1-oxopropyl)-4-(2-methoxyphenyl)piperazine In 20 ml of tetrahydrofuran was dissolved 1.20 g of N,N-carbonyldiimidazole, and a solution of 2.0 g of ethyl 3-(4,5-dimethoxy-2-(1-pyrrolyl)phenyl)propionate in 40 ml of tetrahydrofuran was added to the solution at room temperature while stirring. The stirring was continued at that temperature for additional 1 hour, 2.98 g of 1-(2-methoxyphenyl)piperazine was added thereto, followed by stirring at 40° to 60° C. for 6 hours. The solvent was removed under reduced pressure, and the residue was purified by silica gel column chromatography (chloroform-methanol) to yield 1.9 g of a colorless oily substance. Recrystallization from ethanol gave the title compound as a colorless crystal.

Melting point: 141°–142° C.

IR (KBr, cm$^{-1}$): 2940, 2840, 1630, 1590, 1520

$^1$H-NMR (CDCl$_3$) δ ppm:

1.15–1.45 (2H, m), 2.70–3.15 (6H, m), 3.15–3.90 (4H, m), 3.83, 3.84, 3.91 (each 3H, s), 6.27 (2H, t, J=2.2 Hz), 6.60–7.05 (8H, m)

Elementary analysis for C$_{26}$H$_{31}$N$_3$O$_4$:

Calcd. (%): C 69.47; H 6.95; N 9.35

Found (%): C 69.37; H 6.88; N 9.14

EXAMPLE 6

1-(3-(4,5-Dimethoxy-2-(1-pyrrolyl)phenyl)propyl)-4-(2-methoxyphenyl)piperazine Dihydrochloride Hemihydrate To 100 ml of tetrahydrofuran were added 18 ml of 1.0M borane-tetrahydrofuran complex and 1.14 g of 1-(3-(4,5-dimethoxy-2-(1-pyrrolyl)phenyl)-1-oxopropyl)-4-(2-methoxyphenyl)piperazine at room temperature, and the mixture was heated under reflux for 27 hours. Since it was found that the reaction had not completed, 10 ml of the borane-tetrahydrofuran complex was further added, and the refluxing was continued for additional 9 hours. After cooling to room temperature, 10 ml of water was added to the reaction mixture, and the solvent was removed under reduced pressure. To the residue was added 35 ml of 5% hydrochloric acid, followed by heating at 50° to 60° C. for 2 hours. The reaction mixture was dried over anhydrous sodium sulfate and the solvent was evaporated. The residue was purified by silica gel column chromatography (chloroform) to yield 780 mg of a pale yellow oily substance, which was dissolved in 15 ml of ethanol, 1.0 ml of concentrated hydrochloric acid was added thereto, and the solvent was removed under reduced pressure. Recrystallization of the residue from ethanol-ethyl ether yielded 500 mg of the title compound as a colorless prism crystal.

Melting point: 210°–212° C.

IR (KBr, cm$^{-1}$): 2950, 2750–2000, 1600, 1510

$^1$H-NMR (CDCl$_3$) δ ppm: 1.65–2.10 (2H, m), 2.50–3.15 (4H, m), 3.15–3.80 (4H, m), 3.86, 3.94, 4.08 (3H, s), 4.00–4.60 (2H, m), 4.90–5.40 (2H, m), 6.28 (2H, t, J=2.0 Hz), 6.78 (4H, s), 7.00–7.80 (3H, m), 8.25 (1H, d, J=7.8 Hz);

Elementary analysis for C$_{26}$H$_{33}$N$_3$O$_3$.2HCl.½H$_2$O: Calcd. (%): C 60.35; H 7.01; N 8.12; Found (%): C 60.61; H 6.95; N 8.02.

REFERENCE EXAMPLE 13 m-Meconine

A mixture of 250 g of veratric acid, 275 ml of formaldehyde (40%), and 1000 ml of concentrated hydrochloric acid was heated at 60° to 70° C. for 12 hours while stirring. An equal volume of ice-water was added to the reaction mixture, and the mixture was vigorously stirred on an ice bath. The insoluble material was removed by filtration, and the filtrate was allowed to stand at 5° C. to room temperature for 24 hours, whereupon crude crystals were precipitated, which were collected by filtration, washed with a sodium sulfate aqueous solution, and recrystallized from ethanol to yield 50 g of m-meconine.

Melting point: 155° C.; $^1$H-NMR (CDCl$_3$) δ ppm: 3.98, 3.94 (each 3H, s), 6.90, 7.31 (each 1H), 5.23 (2H).

REFERENCE EXAMPLE 14 m-Hemipinic Acid

A mixture of 7.8 g of m-meconine, 80 ml of water and 1N sodium hydroxide was stirred at 50° to 70° C. for about 1 hour in a water bath for hydrolysis. After cooling on an ice bath, 3.36 g of sodium hydrogencarbonate was added thereto with stirring, and 160 ml of ⅓M potassium permanganate was then added thereto over 5 minutes. Ten minutes later, the ice bath was removed. After 30 minutes, heat generation subsided, and the reaction completed. The reaction mixture was filtered, and the filtrate was rendered acidic with concentrated hydrochloric acid, followed by concentration under reduced pressure to yield 5.3 g of m-hemipinic acid crystals having a melting point of 180° C.

REFERENCE EXAMPLE 15 m-Hemipinic Anhydride

Two grams of m-hemipinic acid were dehydrated and sublimated at 180° to 200° C. in a sublimation purifying apparatus to obtain 1.6 g of m-hemipinic anhydride having a melting point of 174°–176° C.

IR (KBr, cm$^{-1}$): 1764.

EXAMPLE 7

5,6-Dimethoxy-1,3-dioxo-N-2-(4-(2-methoxyphenyl)-1-piperazinyl)ethyl-isoindole A mixture of 1-(2-Amino)ethyl-4-(2-methoxyphenyl) piperazine (640 mg) and 723 mg of m-hemipinic anhydride in 10 ml of toluene was refluxed for 5 hours, followed by allowing to stand at room temperature, whereupon crystals precipitated, which were collected by filtration. The mother liquor was purified by silica gel column chromatography and recrystallization from toluene to yield colorless crystals. The total yield was 700 mg.

Melting point: 206° C.; $^1$H-NMR (CDCl$_3$) δ ppm: 4.00 (6H, s), 3.85 (3H, s), 7.31 (2H, s), 6.8–7.0 m).

A hydrochloride of the compound was prepared.

Melting point: 237°–242° C.; Elementary analysis for C$_{23}$H$_{27}$N$_3$O$_5$.2HCl.½H$_2$O: Calcd. (%): C 54.44; H 5.98; N 8.28; Found (%): C 54.83; H 5.94; N 8.64.

EXAMPLE 8

5,6-Dimethoxy-1-oxo-N-2-(4-(2-methoxyphenyl)-1-piperazinyl)ethyl-isoindole 5,6-Dimethoxy-1,3-dioxo-2-(4-(2-methoxyphenyl)-1-piperazinyl)ethyl-isoindole (900 mg) was refluxed in 34 ml of acetic acid in the presence of 1.8 g of zinc for 200 minutes. The reaction mixture was filtered, concentrated under reduced pressure, and purified by silica gel column chromatography (dichloromethane-methanol=30:1) to yield 600 mg of an amorphous compound. The resulting compound was dissolved in a small amount of ethanol, and 3% hydrogen chloride in ethanol was added thereto in excess to yield a hydrochloride of the title compound.

Melting point: 267°–269° C.; Elementary analysis for C$_{23}$H$_{29}$N$_3$O$_4$.2HCl.H$_2$O: Calcd. (%): C 54.98; H 6.62; N 8.36; Found (%): C 54.48; H 6.78; N 8.18.

REFERENCE EXAMPLE 16

5,6-Dimethoxy-3-benzylidenephthalide

In a 25 ml flask were charged 4.0 g of m-hemipinic anhydride, 4.54 g of homoveratric acid, and sodium acetate, and the flask was buried in a sand bath at 235° to 240° C. to allow the mixture to react for 6 hours. The reaction mixture was purified by silica gel column chromatography (dichloromethane) to yield the title compound as a colorless amorphous compound.

$^1$H-NMR (CDCl$_3$) δ ppm: 3.9–4.0 (each 3H×4), 6.24 (H, s), 6.89 (1H, d, J=9.0 Hz), 7.09, 7.29 (1H×2, s×2), 7.32 (1H, dd, J=1.8, 9.0 Hz), 7.50 (1H, d, J=1.8 Hz).

REFERENCE EXAMPLE 17

4,5-Dimethoxy-2-(3,4-dimethoxyphenyl)acetyl-N-2-(4-(2-methoxyphenyl)-1-piperazinyl)ethyl-benzamide A mixture of 5,6-Dimethoxy-3-benzylidenephthalide (3.0 g) and 3.0 g of 1-(2-amino)ethyl-4-(2-methoxyphenyl)piperazine in ethanol-toluene was refluxed for 5 hours. After completion of the reaction, the solvent was concentrated, and the residue was purified by silica gel column chromatography (dichloromethane:methanol=40:1) to yield 5.2 g of the title compound as an amorphous compound.

EXAMPLE 9

5,6-Dimethoxy-1-(3,4-dimethoxy)benzylidene-3-oxo-2-(4-(2-methoxyphenyl)-1-piperazinyl)ethyl-isoindole Dihydrochloride Sesquihydrate A mixture of 1.06 g of 4,5-dimethoxy-2-(3,4-dimethoxyphenyl)acetyl-N-2-(4-(2-methoxyphenyl)-1-piperazinyl)ethyl-benzamide in acetic anhydride was refluxed for 1 hour. Acetic anhydride was removed under reduced pressure, and the residue was purified by silica gel column chromatography (dichloromethane:methanol=40:1). Recrystallization from methanol gave 850 mg of a colorless crystal.

Melting point: 127°–128° C.; $^1$H-NMR (CDCl$_3$) δ ppm: 6.55 (1H, bs), 4.05 (2H, m), 2.8 (2H, bs), 2.9 (4H, bs), 3.2 (4H, bs).

The resulting crystal was dissolved in a small amount of ethanol, and 3% hydrogen chloride in ethanol was added thereto in excess. Recrystallization from ethanol gave 800 mg of the title compound as a colorless crystal.

Melting point: 240°–241° C.; Elementary analysis for C$_{32}$H$_{37}$N$_3$N$_6$.2HCl.3/2H$_2$O: Calcd. (%): C 58.27; H 6.42; N 6.37; Found (%): C 58.47; H 6.45; N 6.25.

EXAMPLE 10

5,6-Dimethoxy-1-(3,4-dimethoxy)benzyl-3-oxo-2-(4-(2-methoxyphenyl)-1-piperazinyl)ethyl-isoindole Dihydrochloride Hemihydrate 5,6-Dimethoxy-1-(3,4-dimethoxy)benzylidene-3-oxo-2-(4-(2-methoxyphenyl)-1-piperazinyl)ethyl-isoindole was catalytically reduced in ethanol in the presence of 5% palladium-on-carbon. The catalyst was removed by filtration, 3% hydrogen chloride in ethanol was added to the filtrate, the solvent was removed under reduced pressure, and acetone was added to the residue, and the hydrochloride was collected by filtration.

Melting point: 159°–165° C. (with decomposition); Elementary analysis for C$_{32}$H$_{39}$N$_3$O$_6$.2HCl.½H$_2$O: Calcd. (%): C 59.72; H 6.58; N 6.53; Found (%): C 59.67; H 6.67; N 6.62.

REFERENCE EXAMPLE 18

3,4-Dimethoxyphenylcopper Acetylide

In 15 ml of aqueous ammonia was dissolved 0.39 g of copper iodide, and the solution was added to a solution of 0.33 g of 3,4-dimethoxyphenylacetylene in 20 ml of ethanol at room temperature. The mixture was stirred for 1 hour, filtered, washed five times with water, once with ethanol, and once with ethyl ether, and dried under reduced pressure at 40° C. to yield 110 mg of the title compound.

EXAMPLE 11

1-(2-(2-(3,4-Dimethoxyphenyl)ethynyl)-4,5-dimethoxyphenyl)ethyl-4-(2-methoxyphenyl)piperazine Dihydrochloride Monohydrate In 50 ml of pyridine was dissolved 1.58 g of 1-(2-iodo-4,5-dimethoxyphenyl)ethyl-4-(2-methoxyphenyl)piperazine, and 0.80 g of 3,4-dimethoxyphenylcopper acetylide was added thereto. The mixture was heated to 120° C. in a nitrogen atmosphere for 24 hours. The reaction mixture was poured into water and extracted with ethyl acetate. The two-phase (organic and aqueous) liquid was filtered using celite and then again separated into two phases. The organic layer was washed with a saturated sodium chloride aqueous solution, dried over sodium sulfate, filtered, and evaporated to yield 3.75 g of an oily residue. Purification of the residue by silica gel column chromatography gave 0.75 g of amorphous 1-2-(2-(3,4-dimethoxyphenyl)ethynyl)-4,5-dimethoxyphenyl)ethyl-4-

(2-methoxyphenyl)piperazine, which was then converted to a hydrochloride and recrystallized from ethanol gave 0.70 g of the title compound as a colorless crystal.

Melting point: 164°–167° C.; IR (cm$^{-1}$): 2210; Mass Spectrum (EI): 516 (M$^+$, 5.28); $^1$H-NMR (CDCl$_3$) δ ppm: 2.96 (4H, m), 3.36 (6H, m), 3.80–3.96 (2H, m), 3.84 (3H, s), 3.89 (3H, s), 3.91 (6H, s), 3.92 (6H, s), 6.86–7.20 (4H, m), 7.35 (3H, m), 7.53 (2H, m); Elementary analysis for C$_{31}$N$_{36}$N$_2$O$_5$.2HCl.H$_2$O: Calcd. (%): C 61.28; N 6.64; N 4.61; Found (%): C 61.37; H 6.78; N 4.55.

EXAMPLE 12

1-[2-[4,5-Dimethoxy-2-[(3,4-dimethoxyphenyl)hydroxymethyl]]phenyl]ethyl-4-(2-methoxyphenyl)piperazine To a tetrahydrofuran solution of 1.80 g of 1-[2-[2-bromo-4,5-dimethoxyphenyl]ethyl]-4-(2-methoxyphenyl)piperazine was added a 15% hexane solution of 5.0 mmol of butyl lithium at –78° C. After stirring for a while, 830 mg of veratric aldehyde was added thereto, and the mixture was heated to 0° C. Water was added to the reaction mixture, followed by extraction with ethyl acetate. The solvent was removed from the extract by evaporation, and the residue was purified by silica gel column chromatography to yield 1.62 g of the title compound.

$^1$H-NMR (CDCl$_3$) δ ppm: 7.05–6.8 (m, 7H), 6.70 (s, 1H), 6.60 (s, 1H), 5.93 (br, 1H), 3.89 (s, 6H), 3.85 (s, 6H), 3.71 (s, 3H), 3.4–2.4 (m, 13H).

EXAMPLE 13

1-[2-[4,5-dimethoxy-2-(3,4-dimethoxyphenyl)methyl]phenyl]ethyl-4-(2-methoxyphenyl)piperazine An acetic acid solution of 1.62 g of 1-[2-[4,5-dimethoxy-2-[(3,4-dimethoxyphenyl)hydroxymethyl]]phenyl]-ethyl-4-(2-methoxyphenyl)piperazine was subjected to hydrogenation in the presence of a palladium-on-carbon catalyst. After the reaction, the catalyst was removed by filtration, and the solvent was azeotropically removed with benzene to yield 1.60 g of the title compound.

$^1$H-NMR (CDCl$_3$) δ ppm: 7.1–6.6 (m, 9H), 3.93 (s, 2H), 3.89 (s, 3H), 3.86 (s, 3H), 3.85 (s, 3H), 3.82 (s, 3H), 3.81 (s, 3H), 3.3–2.7 (m, 14H).

EXAMPLE 14

1-[2-[4,5-Dimethoxy-2-[(3,4-dimethoxyphenyl)acetyl]phenyl]ethyl-4-(2-methoxyphenyl)piperazine To a tetrahydrofuran solution of 5.80 g of 1-[2-[2-bromo-4,5-dimethoxyphenyl]ethyl]-4-(2-methoxyphenyl)piperazine was added 9.44 ml of a 15% hexane solution of butyl lithium at –78° C. After stirring for a while, the temperature was raised under reduced pressure for degassing. To the solution was added 1.92 g of pivaloyl chloride at –78° C.

Separately, 10.2 ml of a 15% hexane solution of butyl lithium and 2.98 g of ethyl 3,4-dimethoxyphenylacetate were added to a tetrahydrofuran solution of 1.6 g of diisopropylamine at –78° C., followed by stirring for 30 minutes. The resulting solution was added dropwise to the above-prepared solution. The temperature was elevated up to 0° C., at which the mixture was stirred for 2 hours. Water was added thereto, and the mixture was extracted with ethyl acetate. The extract was washed with a saturated sodium chloride aqueous solution, dried over anhydrous sodium sulfate and the solvent was evaporated. The residue was primarily purified by silica gel column chromatography. 4N Hydrochloric acid was added thereto, followed by heating at 100° C. for 15 minutes, to provide a clear solution. The solution was cooled, neutralized with a saturated sodium hydrogencarbonate aqueous solution, and extracted with methylene chloride. The extract was purified by silica gel column chromatography (hexane, ethyl acetate) to yield 490 mg of the title compound as an amorphous powder.

$^1$H-NMR (CDCl$_3$) δ ppm: 7.1–6.7 (m, 9H), 4.13 (s, 2H), 3.92 (s, 3H), 3.87 (s, 6H), 3.86 (s, 3H), 3.85 (s, 3H), 3.3–2.6 (m, 12H).

REFERENCE EXAMPLE 19

1-[(2-Amino-4,5-dimethoxy)phenyl]acetyl-4-(2-methoxyphenyl)piperazine

A methylene chloride solution containing 15 g of (4,5-dimethoxy-2-nitro)phenylacetic acid, 12 g of 2-methoxyphenylpiperazine, and 13 g of dicyclohexylcarbodiimide was stirred at room temperature for 3 hours. A precipitate was removed by filtration, and the solvent was evaporated. The residue was washed with ethyl acetate, followed by filtration to yield 19.7 g of a solid. To the solid were added 400 ml of ethyl acetate and 1.0 g of platinum oxide, and hydrogenation was performed overnight. The reaction mixture was filtered, the solvent was evaporated, and the residue was crystallized from ethyl acetate to yield 7.5 g of the title compound.

Melting point: 113°–116° C.; IR (cm$^{-1}$): 3348, 1606, 1520, 1500, 1462, 1240, 1212, 1038; $^1$H-NMR (CDCl$_3$) δ ppm: 7.1–6.8 (m, 4H), 6.96 (s, 1H), 6.91 (s, 1H), 3.87 (s, 3H), 3.82 (s, 3H), 3.79 (s, 3H), 3.62 (s, 2H), 3.3–2.7 (m, 8H).

REFERENCE EXAMPLE 20

1-[[2-(4-Chlorobutyrylamino)-5,6-dimethoxy]phenyl]ethyl-4-(2-methoxyphenyl)piperazine To a tetrahydrofuran suspension of 300 mg of lithium aluminum hydride under refluxing was added 1.5 g of 1-[(2-amino-4,5-dimethoxy)phenyl]acetyl-4-(2-methoxyphenyl)piperazine. A saturated sodium sulfate aqueous solution was added thereto, and the mixture was extracted with ethyl acetate. The solvent was azeotropically removed with benzene, and to the residue were immediately added 50 ml of methylene chloride, 1.0 ml of triethylamine, and 5.50 g of 4-chlorobutyryl chloride. A sodium hydrogencarbonate aqueous solution was added thereto, and the mixture was extracted with methylene chloride. The solvent was evaporated, and the residue was purified by silica gel column chromatography (ethyl acetate) to yield 700 mg of the title compound.

$^1$H-NMR (CDCl$_3$) δ ppm: 7.57 (s, 1H), 7.25 (s, 1H), 7.1–6.8 (m, 4H), 6.62 (s, 1H), 3.85 (s, 9H), 3.66 (t, 2H, J=7 Hz), 3.2–3.0 (m, 4H), 2.8–2.0 (m, 10H), 2.0–1.5 (m, 2H).

EXAMPLE 15

N-[2-[2-[4-(2-Methoxyphenyl)piperazinyl]ethyl]-4,5-dimethoxy]phenyl]pyrrolidone To a dimethylformamide solution of 110 mg of sodium hydride was added 660 mg of 1-[[2-(4-chlorobutyrylamino)-5,6-dimethoxy]phenyl]ethyl-4-(2-methoxyphenyl)piperazine, and the mixture was heated at 80° C. After completion of the reaction, the reaction mixture was extracted with methylene chloride, and the solvent was azeotropically removed with water and benzene under reduced pressure. Purification by silica gel column chromatography (3% ethanol/chloroform) yielded 463 mg of the title compound.

$^1$H-NMR (CDCl$_3$) δ ppm: 7.24 (s, 1H), 7.0–6.8 (m, 4H), 6.61 (s, 1H), 3.88 (s, 3H), 3.87 (s, 3H), 3.84 (s, 3H), 3.8–3.6 (m, 2H), 3.2–3.0 (m, 4H), 2.8–2.5 (m, 10H), 2.3–2.2 (m, 2H), 1.3–1.1 (m, 2H).

REFERENCE EXAMPLE 21

Ethyl 5,6-Dimethoxy-1-(3,4-dimethoxybenzyl)-1H-indazole-3-carboxylate

In 5000 ml of dimethyl sulfoxide, having been dried over Molecular Sieve 4A, was suspended 250.2 g of ethyl 5,6-dimethoxy-1H-indazole-3-carboxylate, and 38.0 g of lithium methoxide was added thereto. After stirring at room temperature for 1 hour, 185.6 g of 3,4-dimethoxybenzyl chloride (prepared from 336.4 g of 3,4-dimethoxybenzyl alcohol, 300 ml of concentrated hydrochloric acid, and 500 ml of ethyl ether) was added thereto dropwise at room temperature over 10 minutes. After stirring at room temperature for 1 hour, 55.6 g of 3,4-dimethoxybenzyl chloride was added, followed by stirring at room temperature for 1 hour. To the mixture was further added 55.6 g of 3,4-dimethoxybenzyl chloride, followed by stirring at room temperature for 1 hour. The reaction mixture was poured into 30000 ml of ice-water while stirring. The supernatant liquor was discarded by decantation, and 15000 ml of water was added to the residue, followed by stirring at room temperature overnight. The supernatant liquor was removed by decantation, and the residue was dissolved in 10000 ml of chloroform. The solution was dried over sodium sulfate and filtered, and the solvent was removed under reduced pressure. The residue weighing 497.0 g was purified by column chromatography on silica gel (2 kg×9) using chloroform:carbon tetrachloride:ethyl acetate=5:5:1 and then on silica gel (2 kg×4) using ethyl acetate:hexane=2:1. The resulting eluate was recrystallized from ethyl acetate to yield 205.0 g of the title compound as a colorless prism crystal.

Melting point: 138°–141° C.; IR (KBr) cm$^{-1}$: 1728, 1496, 1266, 1216, 1204, 1138, 1022; $^1$H-NMR (CDCl$_3$) δ ppm: 1.49 (3H, t, J=6.8 Hz), 3.78 (3H, s), 3.85 (6H, s), 3.95 (3H, s), 4.53 (2H, q, J=6.8 Hz), 5.58 (2H, s), 6.63 (1H, s), 6.76 (1H, s), 6.80 (2H, s), 7.56 (1H, s); Elementary analysis for C$_{21}$H$_{24}$N$_2$O$_6$: Calcd. (%): C 62.99; H 6.04; N 7.00; Found (%): C 62.83; H 5.99; N 6.93.

REFERENCE EXAMPLE 22

5,6-Dimethoxy-1-(3,4-dimethoxybenzyl)-1H-indazole-3-Methanol

In 1500 ml of tetrahydrofuran was suspended 205.0 g of ethyl 5,6-dimethoxy-1-(3,4-dimethoxybenzyl)-1H-indazole-3-carboxylate, having been ground to powder in a mortar, at room temperature, and 96.8 g of sodium borohydride was added thereto, followed by stirring at room temperature. To the mixture was added dropwise 300 ml of methanol over 30 minutes. After the addition, the reaction mixture was warmed to 50° C. and stirred for 5 hours. To the mixture were further added 19.4 g of sodium borohydride and 60 ml of methanol. The reaction mixture was slowly poured into a mixture of 200 ml of concentrated hydrochloric acid, 5000 ml of water, and 1 kg of ice while stirring. A saturated sodium hydrogencarbonate aqueous solution was added to the aqueous layer at room temperature while stirring until the pH became about 8, whereupon a colorless solid began to precipitate. The solid was collected by filtration, washed with two 500 ml portions of water, dissolved in 10000 ml of chloroform, dried over sodium sulfate, filtered, and evaporation of the solvent gave 185.2 g of a colorless solid. This solid was used in the subsequent reaction without further purification.

Separately, a small aliquot of the solid above obtained was recrystallized from ethanol to yield a colorless prism crystal having a melting point of 187° to 188° C.

IR (KBr) cm$^{-1}$: 3272, 1520, 1470, 1438, 1418, 1318, 1284, 1256, 1210, 1166, 1140, 1062, 1026, 870, 834; $^1$H-NMR (CDCl$_3$) δ ppm: 3.77 (3H, s), 3.82 (3H, s), 3.87 (3H, s), 3.92 (3H, s), 4.97 (2H, s), 5.40 (2H, s), 6.62 (1H, s), 6.69 (1H, m), 6.75 (2H, m), 7.13 (1H, s).

REFERENCE EXAMPLE 23

3-Chloromethyl-5,6-dimethoxy-1-(3,4-dimethoxybenzyl)-1H-indazole

In 1500 ml of dichloromethane was dissolved 184.0 g of 5,6-dimethoxy-1-(3,4-dimethoxybenzyl)-3-hydroxymethyl-1H-indazole at room temperature, followed by stirring under cooling with ice. To the solution was added dropwise 75.4 ml of thionyl chloride over 20 minutes. One minute later, the spot of the starting material on a thin layer chromatogram (ethyl acetate:hexane=2:1) disappeared. The reaction mixture was warmed to room temperature, and 3500 ml of dichloromethane was added thereto. The mixture was washed with 1000 ml of a saturated sodium Hydrogencarbonate aqueous solution, dried over sodium sulfate, filtered, and the evaporation of the solvent gave 189.7 g of a colorless solid. This solid was used in the subsequent reaction without further purification.

$^1$H-NMR (CDCl$_3$) δ ppm: 3.78 (3H, s), 3.84 (3H, s), 3.88 (3H, s), 3.95 (3H, s), 4.95 (2H, s), 5.44 (2H, s), 6.65 (1H, s), 6.71 (3H, m), 7.10 (1H, s).

REFERENCE EXAMPLE 24

5,6-Dimethoxy-1-(3,4-dimethoxybenzyl)-1H-indazole-3-acetonitrile

In 1000 ml of dimethyl sulfoxide was dissolved 187.0 g of 3-chloromethyl-5,6-dimethoxy-1-(3,4-dimethoxybenzyl)-1H-indazole, followed by stirring at room temperature. To the solution was added 134.0 g of potassium cyanide, having been ground to powder in a mortar, followed by stirring at 50° C. for 2 hours. The reaction mixture was cooled to room temperature, poured into 15000 ml of water, and stirred for 1 hour. A precipitated solid was collected, washed with three 1000 ml portions of water, dissolved in 5000 ml of chloroform, dried over sodium sulfate, filtered, and the solvent was evaporated. The residue was purified by silica gel column chromatography using 2 kg of silica gel and chloroform:ethanol=50:1 and then 2 kg of silica gel and ethyl acetate:hexane=3:1, to yield 111.0 g of a pale brown solid. This solid was used in the subsequent reaction without further purification.

$^1$H-NMR (CDCl$_3$) δ ppm: 3.80 (3H, s), 3.84 (3H, s), 3.89 (3H, s), 3.94 (3H, s), 4.02 (2H, s), 5.43 (2H, s), 6.66 (1H, s), 6.72 (2H, m), 6.69 (1H, m), 7.06 (1H, m).

REFERENCE EXAMPLE 25

5,6-Dimethoxy-1-(3,4-dimethoxybenzyl)-1H-indazole-3-acetic Acid

In 1000 ml of ethanol was suspended 111.0 g of 5,6-dimethoxy-1-(3,4-dimethoxybenzyl)-1H-indazole-3- acetonitrile at room temperature and stirred. A 10N sodium hydroxide aqueous solution was added to the suspension, followed by heating under reflux for 2 hours. The reaction mixture was cooled to room temperature and evaporated to remove ethanol. To the residue was added 2000 ml of water, followed by stirring at room temperature overnight. Any insoluble material was removed by filtration, and 500 ml of ethyl ether was added to the filtrate. The organic solvent-soluble material was removed, and the aqueous layer was adjusted to pH 4 to 5 with concentrated hydrochloric acid. A precipitate was collected and fractionally recrystallized from ethanol to yield 41.0 g of the title compound. This compound was used in the subsequent reaction without further recrystallization.

$^1$H-NMR (CDCl$_3$) δ ppm: 3.77 (3H, s), 3.84 (3H, s), 3.88 (3H, s), 3.91 (3H, s), 4.03 (2H, s), 5.44 (2H, s), 6.64 (1H, s), 6.72 (2H, m), 6.77 (1H, m), 6.96 (1H, s).

EXAMPLE 16

1-((5,6-Dimethoxy-1-(3,4-dimethoxybenzyl)-1H-indazol-3-yl)acetyl)-4-(3-chloro-2-methylphenyl) piperazine In 500 ml of dichloromethane was suspended 41.0 g of 5,6-dimethoxy-1-(3,4-dimethoxybenzyl)-1H-indazole-3-acetic acid, and 24.5 g of 2,2-dipyridyl disulfide and 30.0 g of triphenylphosphine were added to the mixture, followed by stirring at room temperature. To the mixture was added dropwise a solution of 23.5 g of (3-chloro-2-methylphenyl) piperazine in 200 ml of dichloromethane over 5 minutes, followed by stirring at room temperature for 30 minutes. After confirming disappearance of the spot of the starting material on a thin layer chromatogram (ethyl acetate:hexane=2:1), 1000 ml of dichloromethane was added to the reaction mixture, and the reaction mixture was washed with water. The organic layer was dried over sodium sulfate, filtered, and the solvent was evaporated. The residue was purified by silica gel column chromatography (ethyl acetate:hexane=2:1; silica gel: 2 kg) to yield 61.5 g of a colorless solid, which was used in the following reaction without further purification. A small aliquot of the solid was recrystallized from ethanol to give a colorless prism crystal having a melting point of 165° to 169° C.

IR (KBr) cm$^{-1}$: 1652, 1516, 1264, 1236; $^1$H-NMR (CDCl$_3$) δ ppm: 1.24 (1.5H, t, J=7.3 Hz, Me of EtOH), 1.65 (4H, s), 2.55 (2H, m), 2.75 (2H, m), 3.72 (1H, m, CH$_2$ of EtOH), 3.76 (3H, s), 3.78 (3H, s), 3.89 (3H, s), 3.94 (3H, s), 4.09 (2H, s), 5.41 (2H, s), 6.65 (1H, s), 6.69 (2H, m), 6.73 (1H, s), 7.03 (1H, t, J=7.8 Hz), 7.09 (1H, d, J=6.8 Hz), 7.19 (1H, s).

EXAMPLE 17

3-(2-(4-(3-Chloro-2-methylphenyl)-1-piperazinyl) ethyl)-5,6-dimethoxy-1-(3,4-dimethoxybenzyl)-1H-indazole In 1000 ml of tetrahydrofuran was suspended 60.5 g of 1-((5,6-dimethoxy-1-(3,4-dimethoxybenzyl)-1H-indazol-3-yl)acetyl)-4-(3-chloro-2-methylphenyl)piperazine, and 500 ml of a tetrahydrofuran solution containing 1.0 mol of a borane-tetrahydrofuran complex was added thereto, followed by refluxing for 2 hours. The reaction mixture was cooled to room temperature, and 30 ml of water was added thereto to decompose the excess reagent. Tetrahydrofuran was removed under reduced pressure, and 300 ml of concentrated hydrochloric acid was added to the residue, followed by stirring at 50° C. for 1 hour. The aqueous layer was cooled to room temperature, made alkaline with potassium carbonate, and extracted with 3000 ml of chloroform. The organic layer was dried over sodium sulfate, filtered, and the solvent was removed under reduced pressure. The residue was purified by silica gel column chromatography (chloroform:ethanol=40:1) to yield 50.0 g of a colorless solid. Recrystallization from ethanol gave 46.3 g of a colorless prism crystal.

Melting point: 148°–150° C.; IR (KBr) cm$^{-1}$: 1518, 1466, 1454, 1260, 1236, 1140, 1022, 1004; $^1$H-NMR (CDCl$_3$) δ ppm: 2.35 (3H, s), 2.85 (2H, m), 3.02 (4H, m), 3.26 (2H, m), 3.78 (3H, s), 3.83 (3H, s), 3.87 (3H, s), 3.94 (3H, s), 5.43 (2H, s), 6.62 (1H, s), 6.72 (2H, s), 6.78 (1H, m), 6.96 (1H, m), 7.11 (3H, m). Elementary analysis for C$_{31}$H$_{37}$N$_4$O$_4$Cl: Calcd. (%): C 65.89; H 6.60; N 9.91; Cl: 6.27; Found (%): C 65.65; H 6.59; N 9.58; Cl: 6.36.

EXAMPLE 18

5,6-Dimethoxy-1-(3,4-dimethoxyphenylmethyl)-3-(2-(4-(2-methoxyphenyl)-1-piperazinyl)ethyl)-1H-indazole Dihydrochloride Monohydrate In 100 ml of dichloromethane was dissolved 2.2 g of 5,6-dimethoxy-1-(3,4-dimethoxyphenylmethyl)-1H-indazole-3-acetic acid, and to the solution were added 1.5 g of triphenylphosphine, 1.26 g of 2,2-dipyridyl disulfide, and 1.1 g of 2-methoxyphenylpiperazine, followed by stirring at room temperature for 1 hour. The reaction mixture was poured into water and extracted with dichloromethane. The organic layer was dried over sodium sulfate, and the solvent was removed under reduced pressure. The residue was purified by silica gel column chromatography (ethyl acetate:hexane) to yield 2.6 g of a colorless oil. The oil (2.6 g) was dissolved in 40 ml of tetrahydrofuran, and 40 ml of a 1.0N borane-tetrahydrofuran complex solution was added thereto, followed by stirring at room temperature for 8 hours. To the solution was added 5.0 ml of water under ice-cooling, and the mixture was stirred and then the solvent was evaporated. To the residue was added 20 ml of concentrated hydrochloric acid, followed by stirring at 60° C. for 30 minutes. The solution was poured into a saturated sodium carbonate aqueous solution to be rendered basic and extracted with chloroform. The organic layer was dried over sodium sulfate, and the solvent was removed under reduced pressure. The residue was purified by silica gel column chromatography (dichloromethane:ethanol=20:1) to yield 2.4 g of a colorless oil. The oil was dissolved in ethanol, and 10 ml of 1N hydrochloric acid was added to the solution, followed by stirring. The solvent was removed under reduced pressure. Recrystallization of the residue from ethyl acetate/ethanol gave 2.7 g of the title compound as a colorless crystal.

Melting point: 190°–193° C.; IR (KBr) cm$^{-1}$: 3348, 2940, 2836, 1632, 1516, 1466, 1262, 1160, 1024, 862, 752; $^1$H-NMR (CDCl$_3$) δ ppm: 8.05 (1H, m), 7.42 (1H, t), 7.25 (1H, s), 7.04 (2H, m), 6.84 (2H, m), 6.76 (1H, m), 6.65 (1H, s), 5.45 (2H, m), 4.85 (2H, m), 4.27 (2H, m), 4.06, 3.98, 3.90, 3.84, 3.83 (each 3H, s), 3.70 (2H, s), 3.88–3.56 (4H, m); Elementary analysis for C$_{31}$N$_{38}$N$_4$O$_5$Cl$_2$: Calcd. (%): C 58.40; H 6.64; N 8.79; Cl 11.12; Found (%): C 58.55; H 6.50; N 8.64; Cl 11.40.

REFERENCE EXAMPLE 26

1-Hydroxy-3-(3,4-dimethoxyphenyl)butyronitrile

To a dry benzene solution containing 46 g of sodium amide was slowly added 177 g of 3,4- dimethoxyphenylacetonitrile under cooling with ice. The mixture was heated under reflux for 30 minutes, followed by cooling to room temperature. Into the reaction mixture was slowly blown 50 ml of ethylene oxide, followed by stirring overnight. Water was added thereto, and the mixture was made acidic with 10% hydrochloric acid. The extracted benzene layer was purified by silica gel column chromatography (hexane: acetone=2:1 to 1:1) to yield 48 g of the title compound.

$^1$H-NMR (CDCl$_3$) δ ppm: 7.0–6.8 (m, 3H), 4.05 (t, 1H, J=7.3 Hz), 3.90 (s, 3H), 3.89 (s, 3H), 3.9–3.7 (m, 2H), 2.3–2.0 (m, 2H).

REFERENCE EXAMPLE 27

α-(3,4-Dimethoxyphenyl)-butyrolactone

A solution (100 ml) of 35 g of 1-hydroxy-3-(3,4-dimethoxyphenyl)butyronitrile in a 1:1 mixture of isopropyl alcohol and concentrated hydrochloric acid was heated under reflux overnight. The reaction mixture was extracted three times with methylene chloride. The organic layer was washed successively with a sodium hydrogencarbonate aqueous solution and a saturated sodium chloride aqueous solution, dried over sodium sulfate, and the solvent was evaporated. The residue was purified by silica gel column chromatography (hexane:acetone=2:1 to 1:1) to yield 28.3 g of the title compound.

$^1$H-NMR (CDCl$_3$) δ ppm: 6.9–6.8 (m, 3H), 4.5–4.4 (m, 1H), 4.4–4.3 (m, 1H), 3.89 (s, 3H), 3.87 (s, 3H), 3.77 (dd, 1H, J=8.8, 10.2 Hz), 2.8–2.6 (m, 1H), 2.5–2.3 (s, 1H).

REFERENCE EXAMPLE 28

α-(2-Nitro-4,5-dimethoxyphenyl)-butyrolactone

Concentrated hydrochloric acid (3.0 ml) was added to a solution of 4.0 g of α-(3,4-dimethoxyphenyl)-butyrolactone in 30 ml of a 2:1 mixture of acetic acid and acetic anhydride. The reaction mixture was poured into a sodium hydrogencarbonate aqueous solution and extracted three times with methylene chloride. The organic layer was washed with a saturated sodium chloride aqueous solution and dried over sodium sulfate. The solvent was evaporated, and the residue was crystallized from ethanol to yield 3.36 g of the title compound.

Melting point: 144°–147° C.; $^1$H-NMR (CDCl$_3$) δ ppm: 7.70 (s, 1H), 6.76 (s, 1H), 4.6–4.4 (m, 2H), 3.97 (s, 3H), 3.96 (s, 3H), 2.95–2.8 (m, 1H), 2.5–2.3 (m, 1H).

REFERENCE EXAMPLE 29

5,6-Dimethoxy-3-hydroxyethyl-1,3-dihydro-2(2H)-indolone

An ethyl acetate solution containing 2.0 g of α-(2-nitro-4,5-dimethoxyphenyl)-butyrolactone and 500 mg of platinum oxide was stirred in a 2.0 atm. hydrogen gas atmosphere. Ethanol was added to the reaction mixture, followed by filtration. The solvent was evaporated to yield 1.76 g of the title compound.

$^1$H-NMR (CDCl$_3$) δ ppm: 9.1–9.0 (br 1H), 6.83 (s, 1H), 6.54 (s, 1H), 4.75–4.4 (m, 1H), 3.87 (s, 3H), 3.86 (s, 3H), 3.9–3.5 (m, 2H), 2.3–2.0 (m, 2H).

REFERENCE EXAMPLE 30

5,6-Dimethoxy-3-methylthio-3-hydroxyethyl-1,3-dihydro-2(2H)-indolone

To 50 ml of dimethylformamide was added 360 mg of sodium hydride, and 1.76 g of 5,6-dimethoxy-3-hydroxyethyl-1,3-dihydro-2(2H)-indolone and 706 mg of dimethyl disulfide were added thereto. To the reaction mixture was added a sodium hydrogencarbonate aqueous solution, and the solvent was evaporated. The residue was extracted three times with methylene chloride, and the organic layer was dried over sodium sulfate. The solvent was evaporated, and the residue was purified by silica gel column chromatography (ethyl acetate) to yield 1.21 g of the title compound.

$^1$H-NMR (CDCl$_3$) δ ppm: 9.1–9.0 (br 1H), 6.85 (s, 1H), 6.55 (s, 1H), 3.88 (s, 6H), 3.8–3.5 (m, 2H), 2.5–2.0 (m, 2H), 1.85 (s, 3H).

REFERENCE EXAMPLE 31

5,6-Dimethoxy-3-[2-[4-(2-methoxyphenyl)-1-piperazinyl]ethyl]-3-methylthio-1,3-dihydro-2(2H)-indolone To a methylene chloride solution of 330 mg of 5,6-dimethoxy-3-methylthio-3-hydroxyethyl-1,3-dihydro-2(2H)-indolone and 0.5 ml of triethylamine was added 2.2 equivalents of mesyl chloride under cooling with ice. A sodium hydrogencarbonate aqueous solution was added to the reaction mixture, and the mixture was extracted three times with ethyl acetate. The organic layer was washed with a saturated sodium chloride aqueous solution and dried over sodium sulfate. The solvent was evaporated, and the residue was purified by silica gel column chromatography (ethyl acetate). The product was dissolved in dimethylformamide, and to the solution were added 300 mg of (2-methoxyphenyl)piperazine, 200 mg of potassium carbonate, and 200 mg of sodium iodide, followed by stirring overnight. A sodium hydrogencarbonate aqueous solution was added thereto, and the reaction mixture was extracted three times with methylene chloride. The organic layer was washed with a saturated sodium chloride aqueous solution, dried over sodium sulfate, and the solvent was evaporated. The residue was purified by silica gel column chromatography (ethyl acetate) to yield 140 mg of the title compound.

$^1$H-NMR (CDCl$_3$) δ ppm: 9.5–9.4 (br 1H), 7.0–6.7 (m, 5H), 6.58 (s, 1H), 3.89, (s, 3H), 3.88 (s, 3H), 3.79 (s, 3H), 3.8–1.9 (m, 12H), 1.80 (s, 3H).

EXAMPLE 19

5,6-Dimethoxy-1-[(3,4-dimethoxyphenyl)methyl]-3-[2-[4-(2-methoxyphenyl)piperazinyl]ethyl]-2-oxoindole In dimethylformamide was suspended 38 mg of sodium hydride. To the suspension were added 285 mg of 5,6-dimethoxy-3-[2-[4-(2-methoxyphenyl)-1-piperazinyl]ethyl]-3-methylthio-1,3-dihydro-2(2H)-indolone and 140 mg of 3,4-dimethoxybenzyl chloride. A sodium hydrogencarbonate aqueous solution was added to the reaction mixture, and the mixture was extracted three times with ethyl acetate. The organic layer was washed with a saturated sodium chloride aqueous solution and dried over anhydrous sodium sulfate. The solvent was evaporated, and the residue was dissolved in ethanol. Separately, an acetone solution containing 2.0 g of Raney nickel was refluxed, and the solvent was removed by decantation. To the residue was added the above prepared ethanol solution, followed by refluxing for 15 minutes. A precipitate was removed by filtration, the solvent was evaporated, and the residue was purified by silica gel column chromatography (hexane:ethyl acetate=1:2 to 0:1) to obtain 201 mg of the title compound.

¹H-NMR (CDCl₃) δ ppm: 7.0–6.7 (m, 8H), 6.38 (s, 1H), 4.13 (d, 1H, J=6.9 Hz), 4.10 (d, 1H, J=7.3 Hz), 3.85 (s, 3H), 3.85 (s, 6H), 3.83 (s, 3H), 3.78 (s, 3H), 3.7–3.5 (m, 1H), 3.2–2.2 (m, 12H).

REFERENCE EXAMPLE 32

1-[7-(2,3-Dihydrobenzofuranyl)]piperazine

In 10 ml of acetic acid was dissolved 884.0 mg of 1-(7-benzofuranyl)piperazine, and 56.7 mg of Pearman's catalyst was added thereto. The mixture was stirred at 65° C. in a hydrogen stream for 4 hours. After completion of the reaction, the catalyst was removed by filtration using Celite. The solvent was evaporated, and the residue was subjected to silica gel column chromatography. From the fraction eluted with 10 vol % chloroform-methanol was obtained 729.4 mg of a crude 2,3-dihydrobenzofuran compound, which was used in the subsequent reaction without further purification.

EXAMPLE 20

3-[2-[4-[7-(2,3-Dihydrobenzofuranyl)]-1-piperazinyl]ethyl]-5,6-dimethoxy-1-(3,4-dimethoxybenzyl)-1H-indazole In 15 ml of anhydrous dichloromethane was dissolved 1.28 g of 5,6-dimethoxy-1-(3,4-dimethoxybenzyl)-1H-indazolylacetic acid. To the solution were added successively 868.6 mg of triphenylphosphine, 729.4 mg of 2,2-dipyridyl disulfide, and 729.4 mg of 1-[7-(2,3-dihydrobenzofuranyl)]piperazine, followed by stirring at room temperature for 10 minutes. After completion of the reaction, water was added thereto, and the mixture was extracted with dichloromethane. The extract was dried over anhydrous sodium sulfate, the solvent was evaporated, and the residue was subjected to silica gel column chromatography (ethyl acetate) to yield 1.16 g of an amide compound as a colorless oily substance. The oily product was dissolved in 20 ml of anhydrous tetrahydrofuran, and 8.1 ml of a 1.0M solution of a borane-tetrahydrofuran complex was added thereto, followed by refluxing for 1 hour. After completion of the reaction, 10 ml of a 10% hydrochloric acid was added to the reaction mixture, followed by further refluxing for 1 hour. After cooling, sodium hydrogencarbonate powder was added thereto for neutralization, and the mixture was extracted with chloroform. The extract was dried over anhydrous sodium sulfate, the solvent was evaporated, and the residue was purified by silica gel column chromatography (ethyl acetate) to yield 729.3 mg of the title compound as a colorless oily substance.

IR (KBr) cm⁻¹: 1514, 1486, 1260, 1028; ¹H-NMR (CDCl₃) δ ppm: 3.70–3.77 (4H, m), 3.79, 3.83, 3.88, 3.94 (each 3H, s), 5.43 (2H, s), 6.62–7.61 (8H, m); Elementary analysis for C₃₂H₃₈N₄O₅·½H₂O: Calcd. (%): C 67.70; H 6.92; N 9.86; Found (%): C 67.62; H 6.59; N 9.24.

REFERENCE EXAMPLE 33

1-[(2-Methoxycarbonyl-4,5-dimethoxy)phenyl]ethyl-4-(2-methoxyphenyl)piperazine

To a tetrahydrofuran solution of 3.8 g of 1-[(2-bromo-4,5-dimethoxy)phenyl]ethyl-4-(2-methoxyphenyl)piperazine was added 6.4 ml of a 15% hexane solution of n-butyl lithium at −78° C. After stirring for a while, 0.5 g of solid carbon dioxide was added thereto. The solvent was removed by evaporation. Methanol was added to the residue, and then about 1 ml of concentrated hydrochloric acid was added, followed by heating under reflux overnight. The reaction mixture was carefully neutralized with a sodium hydrogencarbonate aqueous solution, and ethyl acetate was added thereto. The organic layer was separated. The aqueous layer was made acidic, extracted with methylene chloride, and again subjected to esterification. The resulting organic layer was evaporated, and the residue was crystallized from ethanol to yield 530 mg of the title compound.

Melting point: 118° C.; ¹H-NMR (CDCl₃, 400 MHz) δ ppm: 7.52 (s, 1H), 7.05–6.75 (m, 5H), 3.93 (s, 3H), 3.91 (s, 3H), 3.89 (s, 3H), 3.88 (s, 3H), 3.4–2.6 (m, 12H).

EXAMPLE 21

1-[2-[4,5-Dimethoxy-2-(2-pyridyl)acetyl]phenyl]ethyl-4-(2-methoxyphenyl)piperazine Dihydrochloride Dihydrate To a tetrahydrofuran solution of 158 mg of diisopropylamine were successively added 1.0 ml of a 15% hexane solution of n-butyl lithium and 145 mg of 2-picoline at −78° C., followed by stirring for a while. To the solution was added 650 mg of 1-[(2-methoxycarbonyl-4,5-dimethoxy)phenyl]ethyl-4-(2-methoxyphenyl)piperazine. The temperature was gradually elevated to room temperature, at which the mixture was stirred for 20 minutes. A saturated ammonium chloride aqueous solution was added to the reaction mixture, and the reaction mixture was extracted three times with ethyl acetate. The organic layer was washed with a saturated sodium chloride aqueous solution, dried over sodium sulfate, and the solvent was evaporated. The residue was purified by silica gel column chromatography (ethyl acetate:ethanol=10:1) to yield 360 mg of the title compound.

Melting point: 179°–181° C. (once melted and then re-solidified); IR (cm⁻¹): 2500, 1682, 1520, 1504, 1344, 1272, 1246, 1124; ¹H-NMR (an equivalent mixture of keto form:enol form=2:1) δ ppm: 8.56 (d, J=4.9 Hz, ⅔H), 8.28 (d, J=4.5 Hz, ⅓H), 7.7–7.15 (m, 3H), 7.05–6.75 (m, 6H), 5.62 (s, ⅓H), 4.42 (s, ⅔H), 3.92 (s, ⅔*3H), 3.91 (s, ⅓*3H), 3.90 (s, ⅔*3H), 3.99 (s, ⅓*3H), 3.87 (s, ⅔*3H, 3.85 (⅓*3H), 3.3–2.6 (m, 12H).

REFERENCE EXAMPLE 34

Ethyl 5,6-Dimethoxy-1-(1-trityl-4-imidazolyl)methyl-1H-indazole-3-carboxylate

In 5000 ml of dimethyl sulfoxide was suspended 250.2 g of ethyl 5,6-dimethoxyindazole-3-carboxylate, and 40.2 g of lithium methoxide was added to the suspension, followed by stirring at room temperature for 1 hour. A solution of 447.8 g of 4-chloromethyl-1-tritylimidazole in 2000 ml of dimethyl sulfoxide was added dropwise thereto at room temperature over 10 minutes. After stirring at room temperature for 2 hours, 4.2 g of lithium methoxide and 44.8 g of 4-chloromethyl-1-tritylimidazole were further added thereto, followed by stirring at room temperature for 1 hour. The reaction mixture was poured into 30000 ml of ice-water while stirring. A precipitated crystal was collected, washed with three 2000 ml portions of water, and dried. The solid was dissolved in 10000 ml of chloroform, and the solution was dried over sodium sulfate, filtered, and the solvent was evaporated. The residue was purified by silica gel column chromatography (chloroform:ethanol=50:1) and recrystallized from chloroform/isopropyl alcohol to yield 222.0 g of the title compound as a colorless prism crystal.

Melting point: 184°–186° C.; IR (KBr) cm⁻¹: 1704, 1496, 1268, 1146, 1132, 1092, 748, 700; ¹H-NMR (CDCl₃) δ ppm:

1.21 (6H, d, J=5.9 Hz, Me of iso-PrOH), 1.46 (3H, t, J=7.3 Hz), 3.93 (3H, s), 3.97 (3H, s), 4.01 (1H, m, CH of iso-PrOH), 4.49 (2H, q, J=7.3 Hz), 5.61 (2H, s), 6.79 (1H, s), 7.03 (5H, m), 7.13 (1H, s), 7.28 (10H, m), 7.47 (1H, s), 7.51 (1H, s); Elementary analysis for $C_{35}H_{32}N_4O_4 \cdot C_3H_8O$: Calcd. (%): C 72.13; H 6.37; N 8.85; Found (%): C 71.53; H 6.37; N 8.70.

REFERENCE EXAMPLE 35

5,6-Dimethoxy-1-(1-trityl-4-imidazolyl)methyl-1H-indazole-3-methanol

In 1300 ml of tetrahydrofuran was suspended 222.0 g of ethyl 5,6-dimethoxy-1-(1-trityl-4-imidazolyl)methyl)-1H-indazole-3-carboxylate, having been ground to powder in a mortar, at room temperature, and the suspension was cooled with ice-water. To the suspension was added about 250.0 ml of a 3.4M toluene solution of sodium bismethoxyethoxy-aluminum hydride over 15 minutes, followed by stirring under ice-cooling for 30 minutes. A supersaturated sodium sulfate aqueous solution was added to the reaction mixture. After stirring for 1 hour, sodium sulfate was added thereto, followed by filtration. The sodium sulfate on the filter was washed with five 500 ml portions of hot chloroform. The filtrate and the washing were combined and the solvent was evaporated to yield 220.1 g of a colorless solid. Recrystallization of the solid from chloroform gave 181.0 g of the title compound as a colorless prism crystal.

Melting point: 115°–120° C. (with decomposition); IR (KBr) cm$^{-1}$: 3216, 3172, 3008, 2936, 1510, 1488, 1472, 1444, 1302, 1260, 1172, 1156, 1128, 1102, 1036, 1014, 836, 764, 702, 678, 666, 636; $^1$H-NMR (CDCl$_3$) δ ppm: 3.91 (3H, s), 3.92 (3H, s), 4.92 (2H, s), 5.44 (2H, s), 6.76 (1H, s), 6.95 (1H, s), 7.05 (5H, m), 7.26 (1H, s, CHCl$_3$), 7.28 (1H, s), 7.31 (10H, m), 7.46 (1H, s); Elementary analysis for $C_{33}H_{30}N_4O_3 \cdot CHCl_3$: Calcd. (%): C 62.83; H 4.81; N 8.62; Found (%): C 62.50; H 4.63; N 8.42.

REFERENCE EXAMPLE 36

3-Chloromethyl-5,6-dimethoxy-1-(1-trityl-4-imidazolyl)methyl-1H-indazole

In 1700 ml of dichloromethane was suspended 180.0 g of 5,6-dimethoxy-1-(1-trityl-4-imidazolyl)methyl-1H-indazole- 3-methanol, having been ground to powder in a mortar, at room temperature, followed by stirring while cooling with ice. To the reaction mixture was added dropwise 48.6 ml of thionyl chloride over 5 minutes. One minute later, the spot of the starting material on a thin layer chromatogram (chloroform:ethanol=30:1) disappeared. The reaction mixture was poured into 2000 ml of a saturated sodium hydrogencarbonate aqueous solution and extracted with 5000 ml of chloroform. The extract was dried over sodium sulfate, filtered, and the solvent was evaporated to yield 165.1 g of a colorless solid. This solid was used in the subsequent reaction without further purification.

$^1$H-NMR (CDCl$_3$) δ ppm: 3.95 (3H, s), 4.09 (3H, s), 4.83 (2H, s), 5.67 (2H, s), 7.02 (8H, m), 7.37 (10H, m), 7.88 (1H, br).

REFERENCE EXAMPLE 37

5,6-Dimethoxy-1-(1-trityl-4-imidazolyl)methyl-1H-indazole-3-acetonitrile

In 1200 ml of dimethyl sulfoxide was suspended 165.0 g of 3-chloromethyl-5,6-dimethoxy-1-(1-trityl-4-imidazolyl) methyl-1H-indazole, followed by stirring at room temperature. To the suspension was added 43.6 g of potassium cyanide, having been ground to powder in a mortar, and the mixture was stirred at 70° C. for 1 hour. The reaction mixture was cooled to room temperature and poured into 15000 ml of water with vigorous stirring, followed by stirring for 1 hour. A precipitated solid was collected, washed with three 1000 ml portions of water, and dissolved in 5000 ml of chloroform. The solution was dried over sodium sulfate, filtered, and the solvent was evaporated. Silica gel column chromatography (ethyl acetate) of the residue yielded 108.7 g of a pale brown solid, which was used in the next reaction as such.

$^1$H-NMR (CDCl$_3$) δ ppm: 3.92 (3H, s), 3.94 (3H, s), 3.97 (2H, s), 5.42 (2H, s), 6.79 (1H, s), 7.00 (1H, s), 7.02 (1H, s), 7.06 (5H, m), 7.30 (10H, m), 7.46 (1H, s).

REFERENCE EXAMPLE 38

5,6-Dimethoxy-1-(1-trityl-4-imidazolyl)methyl-1H-indazole-3-acetic Acid

In 1000 ml of ethanol was suspended 107.0 g of 5,6-dimethoxy-1-(1-trityl-4-imidazolyl)methyl-1H-indazole-3-acetonitrile at room temperature, and a 10N sodium hydroxide aqueous solution, prepared from 40.0 g of sodium hydroxide and 100 ml of water, was added thereto, followed by refluxing for 6 hours. The reaction mixture was cooled to room temperature and poured into 5000 ml of water. On adjusting to pH 3 to 4 with 10% hydrochloric acid, a colorless solid precipitated, which was collected by filtration, washed with three 500 ml portions of water, and dissolved in 5000 ml of chloroform. The solution was dried over sodium sulfate, filtered, and the solvent was evaporated to yield 134.0 g of the title compound, which was used in the next reaction as such.

$^1$H-NMR (CDCl$_3$) δ ppm: 3.84 (3H, s), 3.87 (3H, s), 3.89 (2H, s), 5.43 (2H, s), 6.76 (1H, s), 6.88 (1H, s), 6.93 (1H, s), 7.03 (5H, m), 7.28 (10H, m), 7.48 (1H, s).

EXAMPLE 22

4-(3-Chloro-2-methylphenyl)-1-((5,6-dimethoxy-1-(1-trityl-4-imidazolyl)methyl-1H-indazol-3-yl)acetyl)piperazine In 1000 ml of dichloromethane was suspended 134.0 g of 5,6-dimethoxy-1-(1-trityl-4-imidazolyl)methyl-1H-indazole-3-acetic acid. To the suspension were added 63.5 g of 2,2-dipyridyl disulfide and 75.6 g of triphenylphosphine, followed by stirring at room temperature, whereupon the suspension turned uniformly transparent. A solution of 60.7 g of 4-(3-chloro-2-methylphenyl)piperazine in 200 ml of dichloromethane was added thereto dropwise over a period of 5 minutes, and the mixture was stirred at room temperature for 5 hours. The solvent was removed under reduced pressure, and to the residue was added hot ethyl acetate, followed by stirring. A precipitated solid was collected by filtration, washed with two 500 ml portions of ethyl acetate, and dried to yield 140.4 g of a colorless solid. The solid was purified by silica gel column chromatography (chloroform:ethanol=30:1) to give 134.9 g of a colorless solid. Recrystallization from ethanol gave 120.0 g of a colorless prism crystal.

Melting point: 103°–105° C.; IR (KBr) cm$^{-1}$: 1646, 1628, 1508, 1466, 1450, 1430, 1260, 750, 702; $^1$H-NMR (CDCl$_3$) δ ppm: 1.23 (1.2H, t, J=6.8 Hz, Me of EtOH), 2.28 (3H, s), 2.55 (2H, m), 2.73 (2H, m), 3.67 (4H, m), 3.71 (0.8H, q, J=6.8 Hz, CH$_2$ of EtOH), 3.90 (3H, s), 3.93 (3H, s), 4.03 (2H, s), 5.43 (2H, s), 6.68 (1H, s), 6.72 (1H, d, J=8.3 Hz), 6.90 (1H, s), 7.03 (7H, m), 7.14 (1H, s), 7.27 (10H, m), 7.41 (1H, s); Elementary analysis for C$_{45}$H$_{43}$N$_6$O$_3$Cl.0.4EtOH.H$_2$O: Calcd. (%): C 70.10; H 5.70; N 10.70; Cl 4.72; Found (%): C 70.02; H 5.78; N 10.60; Cl 5.11.

EXAMPLE 23

3-(2-(4-(3-Chloro-2-methylphenyl)-1-piperazinyl) ethyl)-5,6-dimethoxy-1-(4-imidazolylmethyl)-1H-indazole In 1000 ml of tetrahydrofuran was suspended 120.0 g of 4-(3-chloro-2-methylphenyl)-1-(5,6-dimethoxy-1-(1-trityl-4-imidazolyl)methyl)indazol-3-yl)acetyl)piperazine- To the suspension was added 800 ml of a 1.0M borane-tetrahydrofuran complex, followed by refluxing for 90 minutes. The reaction mixture was cooled to room temperature, and 30 ml of water was added thereto to decompose the excess reagent. Tetrahydrofuran was removed under reduced pressure, and 150 ml of concentrated hydrochloric acid, 200 ml of water, and 40 ml of ethanol were added to the residue, followed by stirring at 50° C. for 1 hour. The aqueous layer was cooled to room temperature, made alkaline with potassium carbonate, and extracted with 3000 ml of chloroform. The organic layer was dried over sodium sulfate, filtered, and the solvent was evaporated. The residue was purified by silica gel column chromatography (chloroform:ethanol= 40:1) to yield a colorless solid, which was then recrystallized from isopropyl alcohol/isopropyl ether to give 71.0 g of the title compound as a colorless prism crystal.

Melting point: 143°–144.5° C.; IR (KBr) cm$^{-1}$: 1510, 1464, 1432, 1272, 1238, 1206, 1006; $^1$H-NMR (CDCl$_3$) δ ppm: 2.34 (3H, s), 2.78 (4H, m), 2.90 (2H, m), 2.97 (4H, m), 3.17 (2H, m), 3.90 (3H, s), 3.91 (3H, s), 5.45 (2H, s), 6.83 (1H, s), 6.84 (1H, s), 6.92 (1H, m), 7.00 (1H, s), 7.09 (2H, m), 7.52 (1H, s); Elementary analysis for C$_{26}$H$_{31}$N$_6$O$_2$Cl: Calcd. (%): C 63.09; H 6.31; N 16.98; Cl 7.16; Found (%): C 62.93; H 6.30; N 16.88; Cl 7.16.

REFERENCE EXAMPLE 39

1-Benzyloxycarbonyl-4-(3-(2-ethoxycarbonyl)ethyl) carbonylamino-2-methylphenyl)piperazine In 50 ml of methylene chloride were dissolved 5.15 g of 4-(3-amino-2-methylphenyl)-1-benzyloxycarbonylpiperazine and 3.08 g of ethylsuccinyl chloride, and 5.17 g of potassium carbonate was added thereto, followed by heating under reflux for 2 hours. The reaction mixture was cooled to room temperature, and methylene chloride was added thereto. The mixture was washed with water, dried over sodium sulfate, filtered, and the solvent was evaporated. The residue was purified by silica gel column chromatography (ethyl acetate:hexane= 1:2) to yield 5.32 g of the title compound.

$^1$H-NMR (CDCl$_3$) δ ppm: 1.27 (3H, t, J=6.8 Hz), 2.23 (3H, s), 2.71 (2H, m), 2.75 (2H, m), 2.83 (4H, m), 3.66 (4H, m), 4.14 (2H, q, J=6.8 Hz), 5.17 (2H, s), 6.84 (1H, d, J=7.8 Hz), 7.16 (1H, t, J=8.3 Hz), 7.37 (5H, m), 7.53 (1H, d, J=7.8 Hz)

EXAMPLE 24

5,6-Dimethoxy-1-(3,4-dimethoxybenzyl)-3-(2-(4-(2-ethyl-3-(1-succinimidyl)phenyl-1-piperazinyl)ethyl)-1H-indazole In 50 ml of methanol was dissolved 1.50 g of 1-benzyloxycarbonyl-4-(3-(2-ethoxycarbonylethyl) carbonylamino-2-methylphenyl)piperazine, and 1.0 g of 10% palladium-on-carbon was added thereto, followed by stirring at room temperature in a hydrogen atmosphere for 2 hours. The reaction mixture was filtered and the solvent was evaporated to yield 0.99 g of 3-(2-ethoxycarbonylethyl) carbonylamino-2-methylphenylpiperazine, which was used in the next reaction without purification.

In 30 ml of methylene chloride were dissolved 800 mg of 5,6-dimethoxy-1-(3,4-dimethoxybenzyl)-1H-indazole-3-ethanol and 270 mg of mesyl chloride. To the solution was added 1.0 ml of triethylamine while stirring under cooling with ice for 30 minutes. Methylene chloride was added to the reaction mixture, and the reaction mixture was washed with water, dried over sodium sulfate, filtered, and the solvent was evaporated. The residue was dissolved in 30 ml of dimethylformamide, and 990 mg of the above-prepared 3-(2-ethoxycarbonylethyl)carbonylamino-2-methylphenylpiperazine and 3.0 g of potassium carbonate were added to the solution. The mixture was stirred at 60° C. for 2 hours. Dimethylformamide was removed under reduced pressure, and the residue was extracted with ethyl acetate. The extract was washed with water, dried over sodium sulfate, filtered, and the solvent was evaporated. The residue was purified by silica gel column chromatography (ethyl acetate), and the resulting solid was recrystallized from isopropyl alcohol to yield 520 mg of 5,6-dimethoxy-1-(3,4-dimethoxybenzyl)-3-(2-(4-(2-methyl-3-(1-succinimidyl)phenyl)-1-piperazinyl)ethyl)-1H-indazole hemihydrate.

Melting point: 99.5°–103.5° C.; Mass Spectrum (FAB): M$^+$+1: 628; IR (KBr) cm$^{-1}$: 1780; $^1$H-NMR (CDCl$_3$) δ ppm: 2.08 (3H, s), 2.76 (4H, m), 2.93 (6H, m), 3.00 (4H, m), 3.19 (2H, m), 3.79 (3H, s), 3.83 (3H, s), 3.87 (3H, s), 3.93 (3H, s), 5.43 (2H, s), 6.62 (1H. 6.77 (4H, m), 7.03 (1H, s), 7.14 (1H, m), 7.27 (1H, m); Elementary analysis for C$_{35}$H$_{45}$N$_5$O$_6$.½H$_2$O: Calcd. (%): C 66.02; H 6.65; N 10.09; Found (%): C 65.98; H 6.95; N 10.08.

REFERENCE EXAMPLE 40

4,4-Dimethyl-2-(2,4,5-trimethoxyphenyl)-2-oxazoline

To 30 g of trimethoxybenzoic acid was added 30 ml of thionyl chloride, and the solution was heated under reflux for 12 hours. Thionyl chloride was removed under reduced pressure. The residue was added to 50 ml of a methylene chloride solution containing 25 g of 2-amino-2-methyl-1-propanol while cooling with ice, followed by stirring overnight. A precipitate was removed by filtration, and the solvent was removed under reduced pressure to yield an oily amide compound. To the residual amide compound was added dropwise 10 ml of thionyl chloride, followed by stirring, and ethyl ether was added thereto. A precipitate was collected by filtration, neutralized with a sodium hydroxide aqueous solution, and extracted with methylene chloride. The solvent was evaporated, and the residual crystal was washed with hexane to yield 22.4 g of the title compound.

Melting point: 84°–86° C.; $^1$H-NMR (CDCl$_3$) δ ppm: 7.30 (s, 1H), 7.26 (s, 1H), 6.53 (s, 1H), 4.11 (s, 2H), 3.92 (s, 3H), 3.90 (s, 3H), 3.87 (s, 3H), 1.42 (s, 6H).

REFERENCE EXAMPLE 41

2-[4,5-Dimethoxy-2-(3,4-dimethoxyphenyl)]4,4-dimethyl-2-oxazoline

Dimethoxyphenylmagnesium bromide prepared from bromoveratrol was slowly added to a tetrahydrofuran solution of 2.65 g of 4,4-dimethyl-2-(2,4,5-trimethoxyphenyl)-2-oxazoline, followed by stirring overnight. An ammonium chloride aqueous solution was added thereto, and the mixture was extracted with methylene chloride. The extract was purified by silica gel column chromatography (hexane:ethyl acetate=2:3-ethyl acetate). Recrystallization from hexane yielded 1.9 g of the title compound.

Melting point: 109°–110° C.; $^1$H-NMR (CDCl$_3$) δ ppm: 7.27 (s, 1H), 6.9–6.8 (m, 4H), 3.97 (s, 3H), 3.92 (s, 6H), 3.89 (s, 3H), 3.80 (s, 2H), 1.31 (s, 6H).

REFERENCE EXAMPLE 42

4,5-Dimethoxy-2-(3,4-dimethoxyphenyl)benzoic Acid

A solution of 2.6 g of 2-[4,5-dimethoxy-2-(3,4-dimethoxyphenyl)]-4,4-dimethyl-2-oxazoline in methyl iodide was stirred overnight to give 3.0 g of a precipitate. A 20% sodium hydroxide aqueous solution was added to the precipitate, followed by heating under reflux overnight. The reaction mixture was neutralized with 5N hydrochloric acid and extracted with methylene chloride. The solvent was evaporated, and the resulting crystal was washed with ethanol to yield 1.51 g of the title compound.

IR (cm$^{-1}$): 1692, 1508, 1256, 1176, 1026; $^1$H-NMR (CDCl$_3$) δ ppm: 9.7 (br, 1H), 7.52 (s, 1H), 6.9–6.8 (m, 4H), 3.94 (s, 3H), 3.91 (s, 6H), 3.85 (s, 3H).

REFERENCE EXAMPLE 43

4-Chloromethyl-1,2-dimethoxy-5-(3,4-dimethoxyphenyl)benzene

A tetrahydrofuran suspension of 1.5 g of lithium aluminum hydride was refluxed, and 2.43 g of 4,5-dimethoxy-2-(3,4-dimethoxyphenyl)benzoic acid was added thereto. After allowing to cool, a supersaturated sodium sulfate aqueous solution was slowly added thereto. The precipitate was removed by filtration. The solvent was evaporated, and the residue was dissolved in methylene chloride. Concentrated hydrochloric acid was added to the solution, and the mixture was stirred for 2 hours, followed by extraction. Purification by silica gel column chromatography (hexane:ethyl acetate=5:1 to 1:1) of the extract yielded 820 mg of the title compound.

$^1$H-NMR (CDCl$_3$) δ ppm: 7.1–6.9 (m, 4H), 6.78 (s, 1H), 4.52 (s, 2H), 3.95 (s, 3H), 3.93 (s, 3H), 3.92 (s, 3H), 3.89 (s, 3H).

REFERENCE EXAMPLE 44

[[4,5-Dimethoxy-2-(3,4-dimethoxyphenyl)]phenyl] acetic Acid

A dimethylformamide solution containing 1.4 g of 4-chloromethyl-1,2-dimethoxy-5-(3,4-dimethoxyphenyl)benzene and 565 mg of potassium cyanide was stirred at 50° C. for one day. The solvent was removed under reduced pressure, and ethyl acetate was added to the residue. The solution was washed successively with water and a saturated sodium chloride aqueous solution. The solvent was evaporated, and to the residue were added 40 ml of a 20% sodium hydroxide aqueous solution and 15 ml of ethanol, followed by heating under reflux overnight. After cooling, water was added, and the reaction mixture was washed with ethyl ether. The aqueous layer was rendered acidic with hydrochloric acid and extracted with methylene chloride. The solvent was removed under reduced pressure to yield 1.16 g of the title compound as an oily substance.

$^1$H-NMR (CDCl$_3$) δ ppm: 6.9–6.8 (m, 4H), 6.8 (s, 1H), 3.91 (s, 6H), 3.87 (s, 3H), 3.85 (s, 3H), 3.57 (s, 2H).

EXAMPLE 25

1-[2-[4,5-Dimethoxy-2-(3,4-dimethoxyphenyl)] phenyl]acetyl-4-(2-methoxyphenyl)piperazine One drop of dimethylformamide was added to a thionyl chloride solution of 517 mg of [[4,5-dimethoxy-2-(3,4-dimethoxy-2-(3,4-dimethoxyphenyl)]phenyl]acetic acid. Thionyl chloride was removed by azeotropic evaporation with benzene. To a methylene chloride solution of the residue was added 2-methoxyphenylpiperazine. After stirring for a while, the organic layer was extracted and purified by silica gel column chromatography (hexane:ethyl acetate=1:1-ethyl acetate) to yield 599 mg of the title compound.

$^1$H-NMR (CDCl$_3$) δ ppm: 7.0–6.7 (m, 9H), 3.91 (s, 6H), 3.87 (s, 6H), 3.85 (s, 3H), 3.9–3.6 (m, 2H), 3.4–3.2 (m, 2H), 3.0–2.8 (m, 2H), 2.8–2.6 (m, 2H).

EXAMPLE 26

1-[2-[[4,5-Dimethoxy-2-(3,4-dimethoxyphenyl)] phenyl]ethyl]-4-(2-methoxyphenyl)piperazine To a tetrahydrofuran suspension of 150 mg of lithium aluminum hydride was added 593 mg of 1-[2-[[4,5-dimethoxy-2-(3,4-dimethoxyphenyl)]phenyl]acetyl]-4-(2-methoxyphenyl)piperazine while refluxing. After allowing to cool, a supersaturated sodium sulfate aqueous solution was added to the reaction mixture, followed by extracting with ethyl acetate. The solvent was evaporated, and the residue was crystallized from isopropyl alcohol to yield 415 mg of the title compound.

Melting point: 111°–113° C.; IR (cm$^{-1}$): 1504, 1464, 1252, 1174, 1340, 1026; $^1$H-NMR (CDCl$_3$) δ ppm: 8.0–7.7 (m, 9H), 3.92 (br s, 9H), 3.84 (s, 6H), 3.2–2.9 (br, 4H), 2.9–2.4 (m, 8H).

EXAMPLE 27

1-(3-Chloro-2-methylphenyl)-4-[2-[[4,5-dimethoxy-2-(3,4-dimethoxyphenyl)]phenyl]acetyl]-piperazine The title compound was synthesized in a yield of 748 mg in the same manner as described above, except for using 654 mg of [[4,5-dimethoxy-2-(3,4-dimethoxyphenyl)]phenyl] acetic acid, 2.0 ml of thionyl chloride, and 500 mg of (3-chloro-2-methylphenyl)piperazine.

$^1$H-NMR (CDCl$_3$) δ ppm: 7.1–7.0 (m, 2H), 6.9–6.7 (m, 6H), 3.92 (s, 6H), 3.87 (s, 6H), 3.63 (s, 2H), 3.8–3.6 (m, 2H), 3.4–3.2 (m, 2H), 2.8–2.6 (s, 2H), 2.6–2.4 (m, 2H), 2.32 (s, 3H).

EXAMPLE 28

1-(3-Chloro-2-methylphenyl)-4-[2-[[4,5-dimethoxy-2-(3,4-dimethoxyphenyl)]phenyl]ethyl]-piperazine The title compound was synthesized in a yield of 540 mg in the same manner as described above, except for using 740 mg of 1-(3-chloro-2-methylphenyl)-4-[2-[[4,5-dimethoxy-2-(3,4-dimethoxyphenyl)]phenyl]acetyl]-piperazine and 170 mg of lithium aluminum hydride.

Melting point: 137°–139° C.; IR (cm$^{-1}$): 1504, 1464, 1250, 1136, 1008; $^1$H-NMR (CDCl$_3$) δ ppm: 8.2–7.7 (m, 8H), 3.93 (s, 9H), 3.87 (s, 3H), 3.2–2.5 (m, 12H), 2.30 (s, 3H).

EXAMPLES 29 TO 99

Compounds having the formula shown below, in which the symbols, $R^1$, $R^2$, K, G, Z, and Q are defined in Table 3 below, were synthesized in the same manner as in the foregoing Examples. Compounds wherein K is "C" are indole compounds, and those wherein K is "N" is indazole compounds. In these compounds, G is a 3,4-dimethoxybenzyl group unless otherwise shown in the Table. In those compounds wherein $R^1$ and $R^2$ both represent a methoxy group, the methoxy group is at the 5- and 6-positions except where noted.

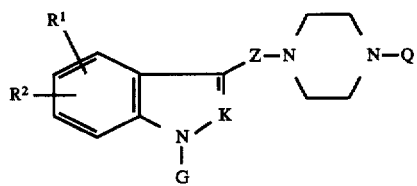

TABLE 3

| Example No. (salt or adduct) | $R^1$, $R^2$ | K | G | Z | Q | Melting Point (°C.) |
|---|---|---|---|---|---|---|
| 29 (HCl) | —OMe, —OMe | N | ![3,4-dimethoxybenzyl] | —(CH$_2$)$_2$— | ![benzofuran] | 127–129 |
| 30 (HCl) | —OMe, —OMe | N | | —(CH$_2$)$_2$— | ![2,3-dimethylphenyl] | 206–208 |
| 31 (HCl.H$_2$O) | —OMe, —OMe | N | | —(CH$_2$)$_2$— | ![pyrazine] | 129–131 |
| 32 (HCl.H$_2$O) | —OMe, —OMe | N | | —(CH$_2$)$_2$— | ![benzodioxole] | 128–132 |
| 33 (HCl) | —OMe, —OMe | N | | —(CH$_2$)$_2$— | ![bis(4-fluorophenyl)methyl] | 146–150 |
| 34 (HCl) | —OMe, —OMe | N | | —(CH$_2$)$_2$— | ![cyclohexyl] | 259–265 |
| 35 (HCl) | —OMe, —OMe | N | | —(CH$_2$)$_2$— | ![furan] | 149–153 |

TABLE 3-continued
| Example No. (salt or adduct) | R¹, R² | K G | Z | Q | Melting Point (°C.) |
|---|---|---|---|---|---|
| 36 (2HCl.H₂O) | —OMe, —OMe | N | —(CH₂)₂— | 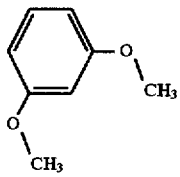 | 127–131 |
| 37 (HCl.H₂O) | —OMe, —OMe | N | —(CH₂)₂— | 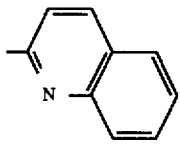 | 197–202 |
| 38 (HCl.H₂O) | —OMe, —OMe | N | —(CH₂)₂— | 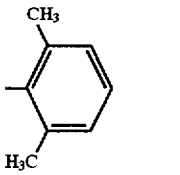 | 161–172 |
| 39 (HCl.H₂O) | —OMe, —OMe | N | —(CH₂)₂— | 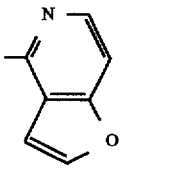 | 129–135 |
| 40 (HCl.H₂O) | —OMe, —OMe | N | —(CH₂)₂— | 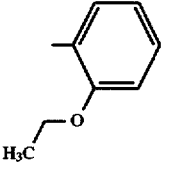 | 161–166 |
| 41 (HCl) | —OMe, —OMe | N | —(CH₂)₂— | 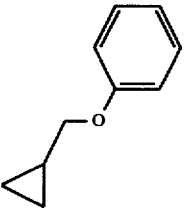 | 74–77 |
| 42 (2HCl.2H₂O) | —OMe, —OMe | N | —(CH₂)₂— | 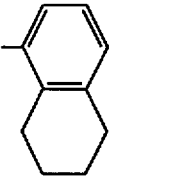 | 205–206 |
| 43 (2HCl.2H₂O) | —OMe, —OMe | N | —(CH₂)₂— | 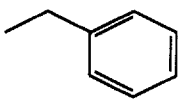 | 193–197 |
| 44 (2HCl.H₂O) | —OMe, —OMe | N | —(CH₂)₂— | 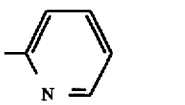 | 142–149 |

TABLE 3-continued

| Example No. (salt or adduct) | R¹, R² | K | G | Z | Q | Melting Point (°C.) |
|---|---|---|---|---|---|---|
| 45 (2HCl) | —OMe, —OMe | N | | —(CH$_2$)$_2$— | 2-F, 3-CH$_3$ phenyl (with CH$_3$) | 182–189 |
| 46 (HCl.H$_2$O) | —OMe, —OMe | N | | —(CH$_2$)$_2$— | dimethyl phenyl ethyl ester | 110–120 |
| 47 (HCl) | —OMe, —OMe | N | | —(CH$_2$)$_2$— | methylpyridine with two pyrrolidinyl groups | 180–185 |
| 48 (2HCl.1/2H$_2$O) | —OMe, —OMe | N | | —(CH$_2$)$_2$— | phenyl | 195–202 |
| 49 (2HCl.3/2H$_2$O) | —OMe, —OMe | N | | —(CH$_2$)$_2$— | isoquinolinyl | 183–185 |
| 50 (HCl.3/2H$_2$O) | —OMe, —OMe | N | | —(CH$_2$)$_2$— | 3-(N,N-diethylamino)phenyl | 119–131 |
| 51 (2HCl) | —OMe, —OMe | N | | —(CH$_2$)$_2$— | 3-F phenyl | 173–178 |
| 52 (2HCl.1/2H$_2$O) | —OMe, —OMe | N | | —(CH$_2$)$_2$— | 3-Cl phenyl | 107–111 |

TABLE 3-continued

| Example No. (salt or adduct) | R¹, R² | K | G | Z | Q | Melting Point (°C.) |
|---|---|---|---|---|---|---|
| 53 | —OMe, —OMe | N | | —(CH$_2$)$_2$— | 3-cyanophenyl | 103–104 |
| 54 | —OMe, —OMe | N | | —(CH$_2$)$_2$— | 2-methyl-3-(N-methylcarbamoyl)phenyl | 106–108 |
| 55 (2HCl) | —OMe, —OMe | N | | —(CH$_2$)$_2$— | 5-(trifluoromethyl)pyridin-2-yl | 224–229 |
| 56 (2HCl) | —OMe, —OMe | N | | —(CH$_2$)$_2$— | 4-(trifluoromethyl)pyridin-2-yl | 120–122 |
| 57 (2HCl) | —OMe, —OMe | N | | —(CH$_2$)$_2$— | 6-(trifluoromethyl)pyridin-2-yl | 187–191 |
| 58 (HCl.H$_2$O) | —OMe, —OMe | N | | —(CH$_2$)$_2$— | 3-chloro-2-methoxyphenyl | 204–207 |
| 59 (HCl.H$_2$O) | —OMe, —OMe | N | | —(CH$_2$)$_2$— | 4-chloro-2-methoxyphenyl | 194–195 |
| 60 (HCl.H$_2$O) | —OMe, —OMe | N | | —(CH$_2$)$_2$— | 4-methoxy-2-(trifluoromethyl)phenyl | 208.5–210 |

TABLE 3-continued
| Example No. (salt or adduct) | R¹, R² | K | G | Z | Q | Melting Point (°C.) |
|---|---|---|---|---|---|---|
| 61 | —OMe, —OMe | N | 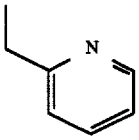 | —(CH$_2$)$_2$— | 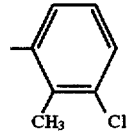 | 111–112 |
| 62 | —OMe, —OMe | N | | —(CH$_2$)$_2$— | 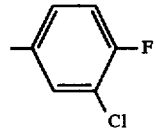 | 146–147.5 |
| 63 | —OMe, —OMe | N | | —(CH$_2$)$_2$— | 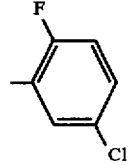 | 113.5–115 |
| 64 | —OMe, —OMe | N | | —(CH$_2$)$_2$— | 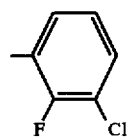 | 108–109 |
| 65 | —OMe, —OMe | N | | —(CH$_2$)$_2$— | 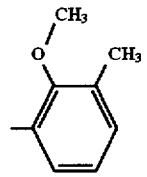 | 129–131 |
| 66 | —OMe, —OMe | N | 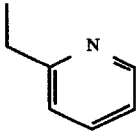 | —(CH$_2$)$_2$— | 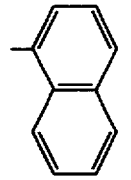 | 148–149 |
| 67 | —OMe, —OMe | N | 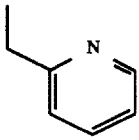 | —(CH$_2$)$_2$— | 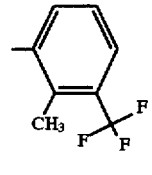 | 128–129 |
| 68 (HCl) | —OMe, —OMe | N | | —(CH$_2$)$_2$— | 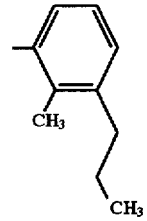 | 97–102 |

TABLE 3-continued

| Example No. (salt or adduct) | R¹, R² | K | G | Z | Q | Melting Point (°C.) |
|---|---|---|---|---|---|---|
| 69 (HCl.H₂O) | —OMe, —OMe | N | | —(CH₂)₂— | (2,2-dimethyl-benzofuran-7-yl with methyl) | 110–114 |
| 70 (HCl) | —OMe, —OMe | N | | —(CH₂)₂— | (2,3,3-trimethyl-2,3-dihydrobenzofuran-7-yl with methyl) | 109–115 |
| 71 (HCl) | —OMe, —OMe | N | | —(CH₂)₂— | (4-chloro-3-methylpyridinyl) | 198–202 |
| 72 (2HCl) | —OMe, —OMe | N | | —(CH₂)₂— | (3-methoxypyridinyl) | 133–138 |
| 73 | —OMe, —OMe | N | (4-propyl-1,3-benzodioxol) | —(CH₂)₂— | (2,3-dimethyl-chlorophenyl) | 137–137.5 |
| 74 | —OMe, —OMe | N | (4-ethyl-1,3-benzodioxol) | —(CH₂)₂— | (2,3-dimethyl-chlorophenyl) | 131.5–132.5 |
| 75 | —OMe, —OMe | N | | —(CH₂)₂— | (pyridinyl) | 175–180 |
| 76 | —OMe, —OMe | N | | —(CH₂)₂— | (2-chloro-3-methylpyridinyl) | 142–143 |
| 77 (2HCl) | —OMe, —OMe | N | | —(CH₂)₂— | (pyridinyl) | 162–168 |

TABLE 3-continued
| Example No. (salt or adduct) | $R^1, R^2$ | K | G | Z | Q | Melting Point (°C.) |
|---|---|---|---|---|---|---|
| 78 | —OMe, —OMe | N | | —(CH$_2$)$_2$— | 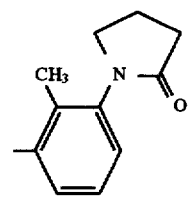 | 130–131 |
| 79 (HCl) | —OMe, —OMe | N | 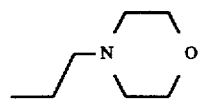 | —(CH$_2$)$_2$— | 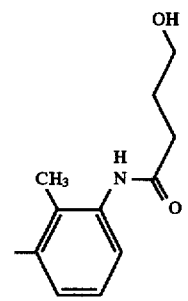 | 245–248 |
| 80 | —OMe, —OMe | N | | —(CH$_2$)$_2$— | 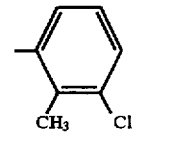 | 132–137 |
| 81 | —OMe, —OMe | N | H | —(CH$_2$)$_2$— | 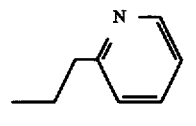 | 175–176 |
| 82 | —OMe, —OMe | N | 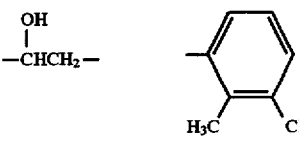 | —(CH$_2$)$_2$— | 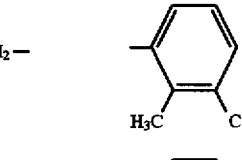 | 78–79 |
| 83 (HCl.H$_2$O) | —OMe, —OMe | N | | OH<br>|<br>—CHCH$_2$— | | 176–180 |
| 84 | —OMe, —OMe | N | | O<br>||<br>—CCH$_2$— | 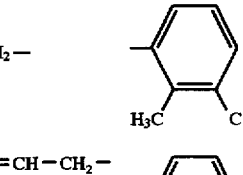 | 115.5–116.5 |
| 85 | —OMe, —OMe | N | | OAc<br>|<br>—CCH$_2$— | | 156–157 |
| 86 | —OMe, —OMe | N | | —CH=CH—CH$_2$— | 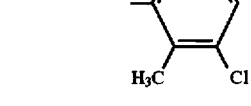 | 131–133 |

TABLE 3-continued
| Example No. (salt or adduct) | R¹, R² | K | G | Z | Q | Melting Point (°C.) |
|---|---|---|---|---|---|---|
| 87 (HCl.H₂O) | —OMe, —OMe | N | | —(CH₂)₂— | 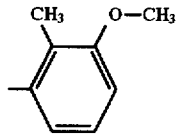 | 125–128 |
| 88 (2HCl) | —OMe, —OMe | N | | —(CH₂)₂— | 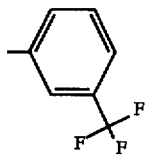 | 111–116 |
| 89 (2HCl.H₂O) | —OMe, —OMe | N | | —(CH₂)₂— | 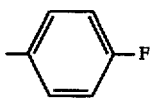 | 208–212 |
| 90 (2HCl.4H₂O) | —OMe, —OMe | N | | —(CH₂)₂— | 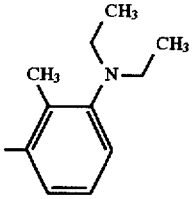 | 109–115 |
| 91 | —OMe, —OMe | N | H | —(CH₂)₂— | 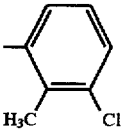 | 175–176 |
| 92 | —OMe, —OMe | C | H | —(CH₂)₂— | 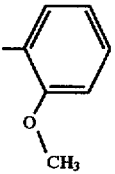 | 110–111 |
| 93 (HCl) | —OMe, —OMe | C | 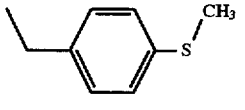 | —(CH₂)₂— | 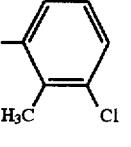 | 210–214 |
| 94 (3HCl) | —OMe, —OMe | C | 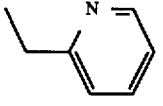 | —(CH₂)₂— | 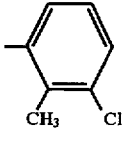 | 155–160 |
| 95 (HCl) | —OMe, —OMe | C | 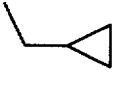 | —(CH₂)₂— | 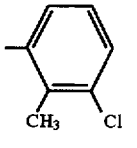 | 212–214 |
| 96 (HCl) | —OMe, —OMe | C | 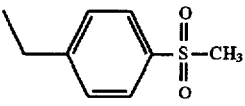 | —(CH₂)₂— | 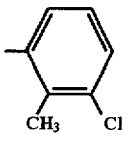 | 218–221 |

TABLE 3-continued

| Example No. (salt or adduct) | R¹, R² | K | G | Z | Q | Melting Point (°C.) |
|---|---|---|---|---|---|---|
| 97 (3HCl) | —OMe, —OMe | C | 4-F-C₆H₄-C(O)- | —(CH₂)₂— | 2-CH₃-3-Cl-C₆H₃- | 238–240 |
| 98 (C₄H₄O₄.1/2H₂O) | —OMe, —OMe | C | 3,4-(OCH₃)₂-phenyl-ethyl | —CH₂— | 2-OCH₃-C₆H₄- | 133–134 |
| 99 (2HCl.3/2H₂O) | —OMe, —OMe | N | 3,4-(OCH₃)₂-phenyl-ethyl | —(CH₂)₂— | 2,3-(OCH₂CH₂O)-C₆H₃- | 110–118 |

EXAMPLES 100 TO 118

Compounds having the formula shown below, in which the symbols, R¹, R², G, Z, and Q are defined in Table 4 below, were synthesized in the same manner as in the foregoing Examples. In those compounds wherein R¹ and R² both represent a methoxy group, the methoxy group is at the 5- and 6-positions except where noted.

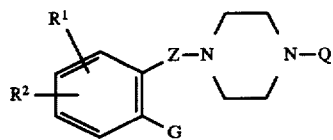

TABLE 4

| Example No. (salt or adduct) | R¹, R² | G | Z | Q | Melting Point (°C.) |
|---|---|---|---|---|---|
| 100 | —OMe, —OMe | H | —(CH₂)₂— | 2-OCH₃-C₆H₄- | 85–86 |
| 101 (HCl) | —OMe, —OMe | pyrrol-1-yl | —(CH₂)₂— | H₃C—O-C₆H₄- | 241–242 |
| 102 (2HCl.H₂O) | —OMe, —OMe | —C≡C—C₆H₅ | —(CH₂)₂— | 2-OCH₃-C₆H₄- | 204–209 |

TABLE 4-continued
| Example No. (salt or adduct) | R¹, R² | G | Z | Q | Melting Point (°C.) |
|---|---|---|---|---|---|
| 103 (2HCl.EtOH) | —OMe, —OMe | 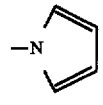 | —(CH$_2$)$_2$— | 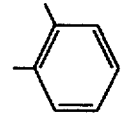 | 218–220 |
| 104 | —OMe, —OMe | 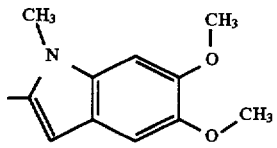 | —(CH$_2$)$_2$— | 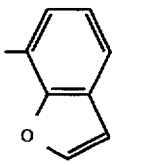 | 189–191 |
| 105 (2HCl.H$_2$O) | —OMe, —OMe | 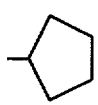 | —(CH$_2$)$_2$— | 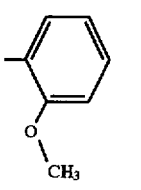 | 222–225 |
| 106 | —OMe, —OMe | 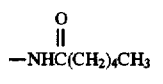 | —(CH$_2$)$_2$— | 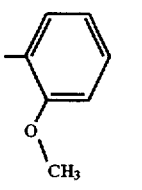 | 80–82 |
| 107 (2HCl.1/2H$_2$O) | —OMe, —OMe | 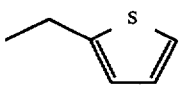 | —(CH$_2$)$_2$— | 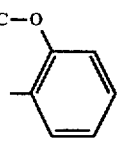 | 184.5–186.5 |
| 108 | —OMe, —OMe | 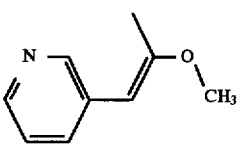 | —(CH$_2$)$_2$— | 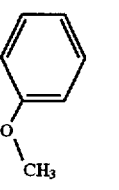 | 128–130 |
| 109 (HCl) | —OMe, —OMe | 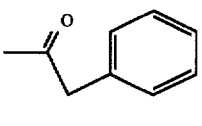 | —(CH$_2$)$_2$— | 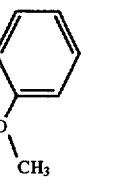 | 165–168 |
| 110 | —OMe, —OMe | 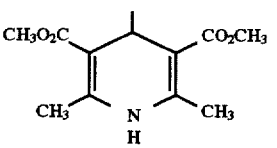 | —(CH$_2$)$_2$— | 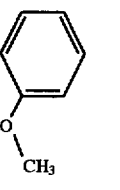 | 98–100 |
| 111 (HCl) | —OMe, —OMe | 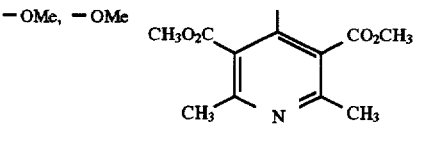 | —(CH$_2$)$_2$— | 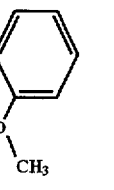 | 216–218 |

TABLE 4-continued

| Example No. (salt or adduct) | $R^1$, $R^2$ | G | Z | Q | Melting Point (°C.) |
|---|---|---|---|---|---|
| 112 (HCl) | —OMe, —OMe | [structure: C(=O)CH2-phenyl-4-F] | —(CH$_2$)$_2$— | [2-methoxyphenyl] | 140–142 |
| 113 (HCl) | —OMe, —OMe | [structure: C(=O)CH2-phenyl-3,4,5-tri-OCH3] | —(CH$_2$)$_2$— | [2-methoxyphenyl] | 175–176 |
| 114 (HCl) | —OMe, —OMe | [structure: C(=O)CH2-phenyl-3,4,5-tri-OCH3] | —(CH$_2$)$_2$— | [2-methyl-3-chlorophenyl] | 186–187 |
| 115 (HCl) | —OMe, —OMe | [structure: C(=N-OH)CH2-phenyl-3,4,5-tri-OCH3] | —(CH$_2$)$_2$— | [2-methyl-3-chlorophenyl] | 230–231 |
| 116 (2HCl) | —OMe, —OMe | [structure: C(=O)CH2-pyridyl] | —(CH$_2$)$_2$— | [2-methyl-3-chlorophenyl] | 229–233 |
| 117 | —OMe, —OMe | [structure: indole-like with OH, 4,5-dimethoxy] | —(CH$_2$)$_2$— | [2-methoxyphenyl] | 111–113 |
| 118 | —OMe, —OMe | [structure: N-CH3 pyrrole] | —(CH$_2$)$_2$— | [2-methoxyphenyl] | 92–93 |

EXAMPLE 119

3-[2-[4-(3-Chloro-2-methylphenyl)-1-piperazinyl]ethyl]-5,6-dimethoxy-1-(4-imidazolylmethyl)-1H-indazole-2HCl.3.5H$_2$O A mixture of 4.95 g of 3-[2-[4-(3-chloro-2-methylphenyl)-1-piperazinyl]ethyl]-5,6-dimethoxy-1-(4-imidazolylmethyl)-1H-indazole and 20 ml of 1N hydrochloric acid was stirred and to the mixture was added water till the overall volume reached to 49.5 ml. The suspension was refluxed with stirring till the mixture turned to a clear solution. After cooling to, room temperature, the solution was stirred at that temperature for overnight. A precipitated crystal was collected by filtration. The crystal was dried under atmospheric pressure for two days to yield 5.5 g of the titled compound as a colorless prism.

Melting point: 166°–167° C.; IR (KBr, cm$^{-1}$): 3400, 2850, 1625, 1505, 1460, 1425, 1245, 1150, 1010, 840; $^1$H-NMR (d$_6$-DMSO) δ ppm: 2.39 (3H, s), 3.30–3.80 (20H, m), 5.74 (2H, s), 7.15 (1H, dd), 7.28 (1H, s), 7.30 (1H, dd), 7.43 (1H, s), 7.52 (1H, s), 7.69 (1H, s), 9.13 (1H, s), 11.80 (1H, bs), 14.80 (1H, bs); Elementary analysis for $C_{26}H_{31}N_6O_2Cl.2HCl.3.5H_2O$: Calcd. (%): C 49.41; H 6.54; N 13.30; Cl 16.83; Found (%): C 49.15; H 6.44; N 13.29; Cl 16.99.

REFERENCE EXAMPLE 45

5,6-Dimethoxy-1-[4-(1-tritylimidazolyl)methyl]indazole-3-propionic Acid

To an ice-cooled solution of diethyl malonate (2.25 g) in tetrahydrofuran (50 ml), was added sodium hydride (0.56 g) and the mixture was stirred for 15 minutes. To the mixture was added dropwise a solution of 3-chloromethyl-5,6-dimethoxy-1-[4-(1-tritylimidazolyl)methyl]indazole (7.70 g) in tetrahydrofuran (50 ml). After the mixture was stirred for 1 hour, the mixture was diluted with ethyl acetate. The mixture was washed with water and dried over anhydrous sodium sulfate.

The solvent was evaporated and a residue (5.5 g, diester derivative, $^1$H-NMR (400 MHz, ppm, CDCl$_3$) δ: 1.14 (6H, t, J=6.8 Hz), 3.46 (2H, t, J=7.8 Hz), 3.87 (3H, s), 3.90 (1H, t, J=7.8 Hz), 3.92 (3H, s), 4.09 (4H, q, J=6.8 Hz), 5.38 (2H, s), 6.64 (1H, s), 6.83 (1H, s), 6.97 (1H, s), 7.06 (6H, m), 7.29 (9H, m), 7.36 (1H, s)) was dissolved in a mixture of water and ethanol (1:1, v/v). To the solution was added potassium hydroxide (1.32 g), and the mixture was heated under reflux for 1 hour. The mixture was cooled to room temperature and adjusted to pH 2.5 with 1N hydrochloric acid. A precipitated solid was collected and dried (dicarboxylic acid derivative, 4.40 g, $^1$H-NMR (400 MHz, ppm, CDCl$_3$) δ: 3.54 (2H, t, J=5.9 Hz), 3.65 (1H, t, J=5.4 Hz), 3.68 (3H, s), 3.90 (3H, s), 5.09 (2H, s), 6.30 (1H, s), 6.43 (1H, s), 6.98 (7H, m), 7.30 (9H, m), 7.74 (1H, s)), then heated at 120° C. for 30 minutes to yield 4.00 g of the titled compound.

$^1$H-NMR (CDCl$_3$, 400 MHz) δ ppm: 2.81 (2H, t, J=7.3 Hz), 3.17 (2H, t, J=7.3 Hz), 3.85 (3H, s), 3.89 (3H, s), 5.32 (2H, s), 6.67 (1H, s), 6.75 (1H, s), 6.93 (1H, s), 7.05 (6H, m), 7.29 (9H, m), 7.74 (1H, s).

REFERENCE EXAMPLE 46

4-(3-Chloro-2-methylphenyl)-1-[[5,6-dimethoxy-1-[4-(1-tritylimidazolyl)methyl-1H-indazol-3-yl]propyl]piperazine To a mixture of 5,6-dimethoxy-1-[4-(1-tritylimidazolyl)methylindazole-3-propionic acid (3.6 g) in dichloromethane (30 ml) were added 2,2'-dipyridyl disulfide (1.66 g) and triphenylphosphine (1.98 g). Then a solution of 4-(3-chloro-2-methylphenyl)piperazine (1.60 g) in dichloromethane (30 ml) was added to the mixture in 1 minute. The mixture was stirred for additional 1 hour, and then diluted with dichloromethane. The mixture was washed with water, dried over anhydrous sodium sulfate, and the solvent was removed under reduced pressure. A residue was chromatographed on silica gel using ethyl acetate as an eluant to yield 4.3 g of the titled compound.

$^1$H-NMR (CDCl$_3$, 400 MHz) δ ppm: 2.32 (3H, s), 2.57 (2H, m), 2.72 (2H, m), 2.83 (2H, t, J=7.8 Hz), 3.25 (2H, t, J=7.8 Hz), 3.49 (2H, m), 3.74 (2H, m), 3.87 (3H, s), 3.92 (3H, s), 5.40 (2H, s), 6.69 (1H, s), 6.77 (1H, d, J=7.8 Hz), 6.84 (1H, s), 7.01 (1H, s), 7.05 (6H, m), 7.12 (2H, m), 7.29 (9H, m), 7.35 (1H, m).

EXAMPLE 120

3-[3-[4-(3-Chloro-2-methylphenyl)-1-piperazinyl]propyl]-5,6-dimethoxy-1-(4-imidazolylmethyl)-1H-indazole To a solution of 4-(3.chloro-2-methylphenyl)-1-[[5,6-dimethoxy-1-[4-(1-tritylimidazolyl)methyl]-1H-indazol-3-yl]propyl]piperazine (4.3 g) in tetrahydrofuran (100 ml), was added 1.0M solution of borane-tetrahydrofuran complex (56 ml), and the mixture was refluxed under an argon gas atmosphere for 90 minutes. The mixture was cooled to room temperature and water was added to the mixture. Tetrahydrofuran was removed under reduced pressure, and to the mixture were added concd. hydrochloric acid (10 ml), water (10 ml) and ethanol (20 ml). The mixture was stirred at 50° C. for 1 hour, then cooled to the room temperature. The mixture was adjusted to alkaline, then extracted with chloroform. The extract was dried over anhydrous sodium sulfate, filtered, and the solvent was evaporated. A residue was chromatographed on silica gel with a mixture of chloroform and ethanol (40:1, v/v) as an eluant.

A crude product was collected and recrystallized from a mixture of isopropanol and isopropyl ether to yield 2.8 g of the title compound as a colorless prism.

Melting point: 85°–89° C.; $^1$H-NMR (CDCl$_3$, 400 MHz) δ ppm: 2.03 (2H, m), 2.32 (3H, s), 2.53 (2H, t, J=7.8 Hz), 2.63 (4H, m), 2.91 (6H, m), 3.91 (3H, s), 3.92 (3H, s), 5.45 (2H, s), 6.85 (1H, s), 6.92 (1H, m), 6.96 (1H, s), 7.08 (2H, m), 7.54 (1H, d, J=1.0 Hz); Elementary analysis for C$_{27}$H$_{33}$N$_6$O$_2$Cl: Calcd. (%): C 61.53; H 6.69; N 15.94; Cl 6.73; Found (%): C 61.44; H 6.98; N 15.66; Cl 6.59.

EXAMPLE 121

3-[2-[4-(3-Chloro-2-methylphenyl)-1-piperazinyl]ethyl]-5,6-dimethoxy-1-(4-morpholinosulfonamidebenzyl)-1H-indazole To a mixture of 3-[2-[1-[4-(3-chloro-2-methylphenyl)piperazinyl]]ethyl]-1H-indazole (700 mg) in dimethylsulfoxide (10 ml), lithium methoxide (140 mg) was added and the mixture was stirred at room temperature for 15 minutes. Then a solution of 4-morpholinosulfonamidebenzyl bromide (1570 mg, 68% purity, containing 32% of 4-morphlinosulfonamidebenzylalcohol) in dimethylsulfoxide (10 ml) was added to the solution in 1 minute. The mixture was stirred at 50° C. for 1 hour. The mixture was poured into water, and a solid precipitated was collected and washed with water, then dried. The solid was dissolved in chloroform and the solution was dried over anhydrous sodium sulfate. The solvent was evaporated and a residue was chromatographed on silica gel using a mixture of chloroform and ethanol (100:1, v/v) to yield 0.84 g of the titled compound as a white solid.

IR (KBr, cm$^{-1}$): 2952, 2824, 1590, 1512, 1466, 1434, 1352, 1262, 1166, 1114, 1094, 1004, 944, 730; $^1$H-NMR (CDCl$_3$, 400 MHz) δ ppm: 2.35 (3H, s), 2.77 (4H, m), 2.97 (10H, m), 3.21 (2H, m), 3.73 (4H, m), 3.90 (3H, s), 3.95 (3H, s), 5.58 (2H, s), 6.60 (1H, s), 6.95 (1H, m), 7.09 (3H, m), 7.24 (2H, m), 7.67 (2H, m).

EXAMPLE 122

3-[2-[4-(3-Chloro-2-methylphenyl)-1-piperazinyl]ethyl]-5,6-dimethoxy-1-(4-pyridylmethyl)-1H-indazole To a mixture of 3-[2-[1-[4-(3-chloro-2-methylphenyl)piperazinyl]]ethyl]-1H-indazole (1 g) in dimethylsulfoxide (10 ml), was added lithium methoxide (200 mg), and the mixture was stirred at 50° C. for 15 minutes. Then, to the solution was added 4-chloromethylpyridine hydrochloride (433 mg), and the mixture was stirred at 50° C. for 1 hour. The mixture was poured into water, and a solid precipitated was collected, washed with water and dried. The solid was dissolved in chloroform and the solution was dried over anhydrous sodium sulfate.

The solvent was evaporated and a residue was chromatographed on silica gel using a mixture of chloroform and ethanol (15:1, v/v) to yield 235 mg of the titled compound as a colorless needle.

Melting point: 117°–118.5° C.; IR (KBr, cm$^{-1}$): 2820, 1512, 1464, 1432, 1416, 1270, 1238, 1212, 1162, 1132, 1038, 1006; $^1$H-NMR (CDCl$_3$, 400 MHz) δ ppm: 2.35 (3H, s), 2.76–2.91 (4H, m), 2.93–2.97 (6H, m), 3.17–3.21 (2H, m), 3.87 (3H, s), 3.94 (3H, s), 5.50 (2H, s), 6.56 (1H, s), 6.94–6.97 (3H, m), 7.07–7.10 (3H, m), 8.52 (2H, d, J=4.40 Hz); Elementary analysis for C$_{28}$H$_{32}$N$_5$O$_2$Cl: Calcd. (%): C 66.46; H 6.37; N 13.84; Cl 7.01; Found (%): C 66.43; H 6.42; N 13.74; Cl 7.26.

EXAMPLE 123

3-[2-[4-(3-Chloro-2-methylphenyl)-1-piperazinyl]ethyl]-1-(4-imidazolylmethyl)-5,6-methylenedioxy-1H-indazole 1.0M solution of borane-tetrahydrofuran complex (10 ml) was added to 4-(3-chloro-2-methylphenyl)-1-[[5,6-dimethoxy-1-[4-(1-tritylimidazolyl)methyl]-1H-indazole-3-yl]ethyl]piperazine (1.91 g) in tetrahydrofuran (10 ml) and refluxed under an argon atmosphere for 90 minutes. The reaction mixture was cooled to room temperature and then added water for the break of excess reagents. After evaporation of tetrahydrofuran, conc. hydrochloric acid (1.0 ml), water (1.0 ml) and ethanol (2.0 ml) were added to this mixture, then stirred at 50° C. for 1 hour. The reaction mixture was cooled to room temperature and adjusted to alkaline, then extracted with chloroform. Organic layer was dried over anhydrous sodium sulfate and was filtered and the solvent was evaporated. The residue was chromatographed on silica gel with a mixture of chloroform and ethanol (25:1) and recrystallized with isopropyl alcohol-isopropyl ether to yield 820 mg of 3-[2-[4-(3-chloro-2-methylphenyl)-1-piperazinyl]ethyl]-1-(4-imidazolylmethyl)-5,6-methylenedioxy-1H-indazole as colorless crystals.

Melting point: 176°–177° C.; IR (KBr, cm$^{-1}$): 2944, 2900, 2832, 1462, 1374, 1274, 1244, 1004, 938, 838; $^1$H-NMR (CDCl$_3$, 400 MHz) δ ppm: 2.34 (3H, s), 2.73 (4H, m), 2.82–2.86 (2H, m), 2.93–2.95 (4H, m), 3.08–3.12 (2H, m), 5.40 (2H, s), 5.97 (2H, s), 6.79–6.96 (2H, m), 6.94 (1H, s), 7.06–7.10 (1H, m), 7.09 (1H, s), 7.54 (1H, s), 9.62 (1H, s).

While the invention has been described in detail and with reference to specific examples thereof, it will be apparent to one skilled in the art that various changes and modifications can be made therein without departing from the spirit and scope thereof.

What is claimed is:

1. A compound represented by formula (I):

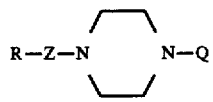

wherein Q is a phenyl group substituted with one or more substituents selected from the group consisting of:
an alkyl group having from 1 to 6 carbon atoms,
an alkoxyl group having from 1 to 6 carbon atoms,
a trifluoromethyl group,
a 2,2,2-trifluoroethyl group,
a trifluoromethoxyl group,
a 2,2,2-trifluoroethoxyl group,
an alkylthio group having from 1 to 6 carbon atoms,
an alkylsulfinyl group having from 1 to 6 carbon atoms,
an alkylsulfonyl group having from 1 to 6 carbon atoms,
an alkanoyl group composed of an alkyl group having from 1 to 6 carbon atoms and a carbonyl group,
an alkanoyloxy group having from 2 to 7 carbon atoms,
an alkanoylamino group having from 2 to 7 carbon atoms,
an amino group,
a monoalkylamino group having from 1 to 6 carbon atoms in the alkyl group thereof,
a dialkylamino group having from 1 to 6 carbon atoms in each alkyl group thereof,
a hydroxyl group,
a halogen atom,
a perfluoroalkyl group having from 2 to 6 carbon atoms,
a cyano group,
a nitro group,
a carboxyl group,
an alkoxycarbonyl group composed of an alkoxyl group having from 1 to 6 carbon atoms and a carbonyl group,
a tetrazolyl group,
a sulfamoyl group,
a methylenedioxy group,
an ethylenedioxy group,
a morpholinosulfonyl group,
a piperazinosulfonyl group,
a 4-alkylpiperazinosulfonyl group having from 1 to 6 carbon atoms,
a 4-dialkylaminopiperidino group having from 1 to 6 carbon atoms in each alkyl group thereof,
a 4-monoalkylaminopiperidino group having from 1 to 6 carbon atoms in the alkyl group thereof, and
a 4-aminopiperidino group, R is

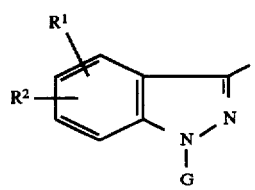

or

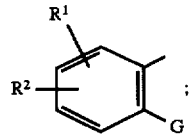

wherein G is:
an alkyl group having from 1 to 6 carbon atoms,
a substituted or unsubstituted phenyl group,
a benzoyl group with the phenyl group thereof substituted or unsubstituted,
a benzylcarbonyl group with the phenyl group thereof substituted or unsubstituted,
a benzoylmethyl group with the phenyl group thereof substituted or unsubstituted,
an α-hydroxybenzyl group with the phenyl group thereof substituted or unsubstituted, a substituted or unsubstituted 5-membered aromatic heterocyclic group containing a nitrogen atom, an oxygen atom or a sulfur atom as a hetero atom, wherein when a nitrogen atom is present as the hetero atom, this has a hydrogen atom or an alkyl group having from 1 to 6 carbon atoms, or is the site of bonding to the bicyclic nitrogen-containing heterocyclic group or the phenyl group, a substituted or unsubstituted 5-membered aromatic heterocyclic group containing one nitrogen atom and, a nitrogen atom, an oxygen atom or a sulfur atom as the second hetero atom, wherein when a nitrogen atom is present as the second hetero atom, this has a hydrogen atom or an alkyl group having from 1 to 6 carbon atoms, or is the site of bonding to the bicyclic nitrogen-containing heterocyclic group or the phenyl group, a substituted or unsubstituted 5-membered aromatic heterocyclic group containing two nitrogen atoms and, a nitrogen atom, an oxygen atom or a sulfur atom as the third hetero atom, wherein when a nitrogen atom is present as the third hetero atom, this has a hydrogen atom or an alkyl group having from 1 to 6 carbon atoms, or is the site of bonding to the bicyclic nitrogen-containing heterocyclic group or the phenyl group, a substituted or unsubstituted 6-membered aromatic heterocyclic group containing one or two nitrogen atoms, a heterocyclic group substituted-alkyl group composed of a substituted or unsubstituted 5-membered aromatic heterocyclic group containing a nitrogen atom, an oxygen atom or a sulfur atom as a hetero atom, wherein when a nitrogen atom is present as the hetero atom, this has a hydrogen atom or an alkyl group having from 1 to 6 carbon atoms, and an alkylene group of from 1 to 3 carbon atoms, a heterocyclic group substituted-alkyl group composed of a substituted or unsubstituted 5-membered aromatic heterocyclic group containing one nitrogen atom and, a nitrogen atom, an oxygen atom or a sulfur atom as the second hetero atom, wherein when a nitrogen atom is present as the second hetero atom, this has a hydrogen atom or an alkyl group having from 1 to 6 carbon atoms or is the site of bonding to the alkylene group, and an alkylene group of from 1 to 3 carbon atoms, a heterocyclic group substituted-alkyl group composed of a substituted or unsubstituted 5-membered aromatic heterocyclic group containing two nitrogen atoms and, a nitrogen atom, an oxygen atom or a sulfur atom as the third hetero atom, wherein when a nitrogen atom is present as the third hetero atom, this has a hydrogen atom or an alkyl group having from 1 to 6 carbon atoms or is the site of bonding to the alkylene group, and an alkylene group of from 1 to 3 carbon atoms, a heterocyclic group substituted-alkyl group composed of a substituted or unsubstituted 6-membered aromatic heterocyclic group containing one or two nitrogen atoms and an alkylene group of from 1 to 3 carbon atoms, a phenylhydroxyalkyl group composed of an alkylene group having one hydroxyl group and 2 to 3 carbon atoms, and a substituted or unsubstituted phenyl group, a 2-phenylethenyl group wherein the phenyl group may be substituted, a tetrazolyl group, a morpholino group, an alkanoylamino group having from 2 to 7 carbon atoms, a tetrazolylalkyl group composed of a tetrazolyl group and an alkylene group having from 1 to 3 carbon atoms wherein the alkylene group is bonded to the carbon atom or nitrogen atom of the tetrazolyl group, a morpholinoalkyl group composed of a morpholino group and an alkylene group having from 1 to 3 carbon atoms, a 4-alkoxycarbonylcyclohexyl group having from 1 to 6 carbon atoms in the alkoxyl group thereof, an alkoxycarbonyl group having from 1 to 6 carbon atoms in the alkoxyl group thereof, an alkoxycarbonylalkyl group composed of an alkoxyl group having from 1 to 6 carbon atoms and an alkylene group having from 1 to 3 carbon atoms, a 1-alkylindol-2-yl group having from 1 to 6 carbon atoms in the alkyl group thereof wherein the indole group may further be substituted, a substituted or unsubstituted pyrrolidon-1-yl group, a 2-guanidinothiazolyl group, a (2-guanidinothiazolyl) alkyl group composed of a 2-guanidinothiazolyl group and an alkylene group having from 1 to 3 carbon atoms, a substituted or unsubstituted 1,4-dihydropyridyl group, a (4-alkylpiperazino)alkyl group composed of a 4-alkylpiperazine having an alkyl group of from 1 to 6 carbon atoms and an alkylene group of from 1 to 6 carbon atoms, a [4-(morpholinosulfonyl)phenyl]alkyl group composed of a 4-(morpholinosulfonyl)phenyl group and an alkylene group of from 1 to 6 carbon atoms, a [4-(piperazinosulfonyl)phenyl]alkyl group composed of a 4-(piperazinosulfonyl)phenyl group and an alkylene group of from 1 to 6 carbon atoms, a [4-(4-alkylpiperazinosulfonyl)phenyl]alkyl group composed of a 4-(4-alkylpiperazinosulfonyl)phenyl group wherein the alkyl group on the piperazino group is from 1 to 6 carbon atoms, and an alkylene group of from 1 to 6 carbon atoms, an alkoxycarbonylalkyl group composed of an alkoxyl group of from 1 to 6 carbon atoms and a carbonyl group, and an alkylene group of from 1 to 6 carbon atoms, a carboxyalkyl group composed of a carboxyl group and an alkylene group of from 1 to 6 carbon atoms, a [4-(4-dialkylaminopiperidino)phenyl]alkyl group composed of a phenyl group having a 4-dialkylaminopiperidino group at the 4-position, wherein each alkyl group of the dialkylamino group has from 1 to 6 carbon atoms independently, and an alkylene group of from 1 to 6 carbon atoms, a [4-(4-monoalkylaminopiperidino)phenyl]alkyl group composed of a phenyl group having a 4-monoalkylaminopiperidino group at the 4-position, wherein the alkyl group of the monoalkylamino group has from 1 to 6 carbon atoms, and an alkylene group of from 1 to 6 carbon atoms, a [4-(4-aminopiperidino)phenyl]alkyl group composed of a phenyl group having a 4-aminopiperidino group at the 4-position and an alkylene group of from 1 to 6 carbon atoms, a (4-dialkylaminopiperidino)alkyl group composed of a 4-dialkylaminopiperidino group, wherein each alkyl group of the dialkylamino group has from 1 to 6 carbon atoms independently, and an alkylene group of from 1 to 6 carbon atoms, a (4-alkylaminopiperidino)alkyl group composed of a 4-alkylaminopiperidino group, wherein the alkyl group of the alkylamino group has from 1 to 6 carbon atoms, and an alkylene group of from 1 to 6 carbon atoms, a (4-aminopiperidino)alkyl group composed of a 4-aminopiperidino group and an alkylene group of from 1 to 6 carbon atoms, a phenylalkyl group composed of a substituted or unsubstituted phenyl group and an alkylene group of from 1 to 6 carbon atoms or a hydrogen atom, wherein in case G has a substituent(s), the substituent(s) is:

an alkyl group having from 1 to 6 carbon atoms, an alkoxyl group having from 1 to 6 carbon atoms, a trifluoromethyl group, a 2,2,2-trifluoroethyl group, a trifluoromethoxyl group, a 2,2,2-trifluoroethoxyl group, an alkylthio group having from 1 to 6 carbon atoms, an alkylsulfinyl group having from 1 to 6 carbon atoms, an alkylsulfonyl group having from 1 to 6 carbon atoms, an alkanoyl group composed of an alkyl group having from 1 to 6 carbon atoms and a carbonyl group, an alkanoyloxy group having from 2 to 7 carbon atoms, an alkanoylamino group having from 2 to 7 carbon atoms, an amino group, a monoalkylamino group having from 1 to 6 carbon atoms in the alkyl group thereof, a dialkylamino group having from 1 to 6 carbon atoms in each alkyl group thereof, a hydroxyl group, a halogen atom, a perfluoroalkyl group having from 2 to 6 carbon atoms, a cyano group, a nitro group, a carboxyl group, an alkoxycarbonyl group composed of an alkoxyl group having from 1 to 6 carbon atoms and a carbonyl group, a tetrazolyl group, a sulfamoyl group, a methylenedioxy group, an ethylenedioxy group, a morpholinosulfonyl group, a piperazinosulfonyl group, a 4-alkylpiperazinosulfonyl group having from 1 to 6 carbon atoms, a 4-dialkylaminopiperidino group having from 1 to 6 carbon atoms in each alkyl group thereof, a 4-monoalkylaminopiperidino group having from 1 to 6 carbon atoms in the alkyl group thereof, or a 4-aminopiperidino group;

$R^1$ and $R^2$ independently is:

an alkyl group having from 1 to 6 carbon atoms, an alkoxyl group having from 1 to 6 carbon atoms, a trifluoromethyl group, a 2,2,2-trifluoroethyl group, a trifluoromethoxyl group, a 2,2,2-trifluoroethoxyl group, an alkylthio group having from 1 to 6 carbon atoms, an alkylsulfinyl group having from 1 to 6 carbon atoms, an alkylsulfonyl group having from 1 to 6 carbon atoms, an alkanoyl group composed of an alkyl group having from 1 to 6 carbon atoms and a carbonyl group, an alkanoyloxy group having from 2 to 7 carbon atoms, an alkanoylamino group having from 2 to 7 carbon atoms, an amino group, a monoalkylamino group having from 1 to 6 carbon atoms in the alkyl group thereof, a dialkylamino group having from 1 to 6 carbon atoms in each alkyl group thereof, a hydroxyl group, a halogen atom, a perfluoroalkyl group having from 2 to 6 carbon atoms, a cyano group, a nitro group, a carboxyl group, an alkoxycarbonyl group composed of an alkoxyl group having from 1 to 6 carbon atoms and a carbonyl group, a tetrazolyl group, a sulfamoyl group, a methylenedioxy group, an ethylenedioxy group, a morpholinosulfonyl group, a piperazinosulfonyl group, a 4-alkylpiperazinosulfonyl group having from 1 to 6 carbon atoms, a 4-dialkylaminopiperidino group having from 1 to 6 carbon atoms in each alkyl group thereof, a 4-monoalkylaminopiperidino group having from 1 to 6 carbon atoms in the alkyl group thereof, or a 4-aminopiperidino group;

and Z is:

an alkylene group having from 1 to 3 carbon atoms, an alkenylene group having from 2 to 4 carbon atoms, an alkylene group having one hydroxyl group and from 1 to 3 carbon atoms, a carbonyl group, an alkylene group containing a carbonyl group at one end or on the middle of the carbon chain thereof, and an oxalyl group, or a pharmaceutically acceptable salt thereof.

2. A compound as claimed in claim 1, wherein R is:

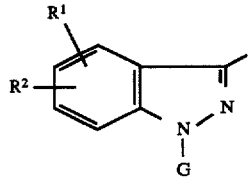

and $R^1$, $R^2$ and G are as defined in claim 1.

3. A compound as claimed in claim 1, wherein R is:

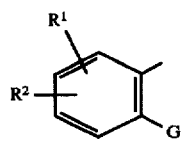

and $R^1$, $R^2$ and G are as defined in claim 1.

4. A compound as claimed in claim 1, 2, or 3, wherein Q is a phenyl group having at least one substituent at the meta-position of the connecting position of the phenyl group to the piperazine group.

5. A compound as claimed in claim 4, wherein the meta-substituent of the phenyl group is a halogen atom.

6. A compound as claimed in claim 5, wherein Q is a 2-methyl-3-chlorophenyl group.

7. A compound as claimed in claim 1, 2, 3, 4, 5, or 6, wherein Z is an alkylene group having 2 or 3 carbon atoms.

8. A compound as claimed in claim 7, wherein Z is an alkylene group having 2 carbon atoms.

9. A compound as claimed in claim 1, 2, 5, 6, 7, or 8, wherein the R is a 5,6-dimethoxy-1H-indazole group.

10. A compound as claimed in claim 1, 2, 4, 5, 6, 7, or 8, wherein the R is a 5,6-methylenedioxy-1H-indazole group.

11. A compound as claimed in claim 9 or 10, wherein the substituent G is a 3,4-dimethoxybenzyl group, 4-imidazolylmethyl group, a 2-pyridylmethyl group, 3-pyridylmethyl group or a 4-pyridylmethyl group.

12. A compound as claimed in claim 1, 3, 4, 5, 6, 7, or 8, wherein R is a 2-substituted-4,5-dimethoxyphenyl group.

13. A compound a claimed in claim 1, 3, 4, 5, 6, 7, or 8, wherein R is a 2-substituted-4,5-methylenedioxyphenyl group.

14. A compound as claimed in claim 10, wherein the substituent G or R is a member selected from the group consisting of a 3,4-dimethoxybenzyl group, a 4-imidazolylmethyl group, a 2-pyridylmethyl group, a 3-pyridylmethyl group and a 4-pyridylmethyl group.

* * * * *